(12) United States Patent
White et al.

(10) Patent No.: US 6,613,890 B2
(45) Date of Patent: *Sep. 2, 2003

(54) PROTEASE INHIBITOR PEPTIDES

(75) Inventors: R. Tyler White, Fremont, CA (US); Deborah Damm, Redwood City, CA (US); David D. Lesikar, Palo Alto, CA (US); Kathleen McFadden, Mountain View, CA (US); Brett L. Garrick, Palo Alto, CA (US)

(73) Assignee: Scios, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/234,873

(22) Filed: Jan. 21, 1999

(65) Prior Publication Data

US 2003/0017546 A1 Jan. 23, 2003

Related U.S. Application Data

(60) Continuation of application No. 08/829,876, filed on Apr. 2, 1997, now Pat. No. 5,962,266, which is a division of application No. 08/436,555, filed on May 8, 1995, now abandoned.

(51) Int. Cl.$^7$ ........................ C07H 21/04; A61K 38/55; C07K 14/81
(52) U.S. Cl. ...................... 536/23.1; 530/324; 536/23.5
(58) Field of Search ........................... 455/252.3, 320.1, 455/69.2; 536/23.5, 23.1; 530/324

(56) References Cited

U.S. PATENT DOCUMENTS

| | | | |
|---|---|---|---|
| 5,187,153 A | 2/1993 | Cordell et al. | 514/12 |
| 5,223,409 A | 6/1993 | Ladner et al. | 435/69.7 |
| 5,223,482 A | 6/1993 | Schilling, Jr. et al. | 514/12 |
| 5,373,090 A | 12/1994 | Norris et al. | 530/324 |
| 5,403,484 A | 4/1995 | Ladner et al. | 435/235.1 |
| 5,436,153 A | 7/1995 | Sprecher et al. | 435/240.2 |
| 5,795,865 A | 8/1998 | Markland et al. | 514/12 |
| 5,795,954 A | 8/1998 | Lazarus et al. | 530/324 |
| 5,834,244 A | 11/1998 | Dennis et al. | 435/69.2 |

FOREIGN PATENT DOCUMENTS

| | | |
|---|---|---|
| EP | 90 10 6529.2 | 10/1990 |
| WO | WO 92/15605 | 9/1992 |
| WO | WO 93/09233 | 5/1993 |

OTHER PUBLICATIONS

Dennis, M. et al., "Kunitz Domain Inhibitors of Tissue Factor–Factor Vlla", *J. of Biol. Chem.*, vol. 269, No. 35, Sep. 2, pp. 22129–22136, 1994.

Colman, R., "Factor XII Activation and Inhibition In Inflammation", *Proteases, Protease Inhibitors and Protease–Derived Peptides*, pp. 125–143, 1993.

Scott, C. et al., "Kinetics of Inhibition of Human Plasma Kallikrein by a Site–Specific Modified Inhibitor Arg$^{15}$–Aprotin: Evaluation Using a Microplate System & Comparison with Other Proteases", *Blood*, vol. 69, No. 5 (May), 1987: pp. 1431–1436.

Patson, P. et al., "Reactivity of $\alpha_1$–Antitrypsin Mutants against Proteolytic Enzymes of the Kallikrein–Kinin, Complement, and Fibrinolytic Systems", *J. of Biol. Chem.*, vol. 265, No. 18, pp. 10786–10791, Jun. 25, 1990.

Wen, L. et al., "Chemical Synthesis, Molecular Cloning, Overexpression, and Site–Directed Mutagenesis of the Gene Coding for Pumpkin (Curcubita maxima) Trypsin Inhibitor CMTI–V", *Protein Expression and Purification 4*, pp. 215–222 (1993).

Pedersen, L. et al., "The Corn Inhibitor of Blood Coagulation Factor Xlla, Crystallization and Preliminary Crystallographic Analysis", *J. Mol. Biol.* (1994) 236, pp. 385–387.

Ponte, P. et al., "A New A4 Amyloid mRNA contains a domain homologous to serine proteinase inhibitors", *Nature*, vol. 331, pp. 525–527, Feb. 11, 1988.

Tanzi, R. et al., "Protease Inhibitor Domain Encoded by an Amyloid Protein Precursor mRNA associated with Alzheimer's Disease", *Nature*, vol. 331, pp. 528–530, Feb. 11, 1988.

Johnstone, E. et al., "Alzheimer's Disease Amyloid Peptide is Encoded by Two Exons and Shows Similarity to Soybean Trypsin Inhibitor", *Biochem. & Biophys. Res. Comm.*, vol. 163, No. 3, pp. 1248–1255, Sep. 29, 1989.

Oltserdorf, T. et al., "The secreted form of the Alzheimer's amyloid precursor protein with the Kunitz domain is protease nexin–II", *Nature*, vol. 341, pp. 144–147, Sep. 14, 1989.

Sinha, Sukanto et al., "The Protease Inhibitory Properties of the Alzheimer's $\beta$–Amyloid Precursor Protein", *J. of Biol. Chem.*, vol. 265, No. 16, pp 8983–8985, Jun. 5, 1990.

Perona, J. et al., "Crystal Structures of Rat Anionic Trypsin Complexed with the Protein Inhibitors APPI and BPTI", *J. Mol. Biol.* 230, pp. 919–933 (1993).

Wenzel, H. et al., "Semisynthetic Conversion of the Bovine Trypsin Inhibitor (Kunitz) into an Efficient Leukocyte–Elastase Inhibitor by Specific Valine for Lysine Substitution in the Reactive Site", *Chem. of Peptides and Proteins*, vol. 3, pp. 105–117, (1986).

Norris, K. et al., "Aprotinin and Aprotinin Analogues Expressed in Yeast", Walter de Gruyter & Co., pp. 37–42, May 1990.

*Primary Examiner*—Elizabeth Slobodyansky
(74) *Attorney, Agent, or Firm*—Foley & Lardner

(57) ABSTRACT

Analogues of the Kunitz Protease Inhibitor (KPI) domain of amyloid precursor protein bind to and inhibit activity of serine proteases, including kallikrein, plasmin and coagulation factors such as factors VIIa, IXa, Xa, XIa, and XIIa. Pharmaceutical compositions containing the KPI analogues, along with methods for using such compositions, are useful for ameliorating and treating clinical conditions associated with increased serine protease activity, such as blood loss related to cardiopulmonary bypass surgery. Nucleic acid sequences encoding these analogues and systems for expression of the peptides of the invention are provided.

10 Claims, 54 Drawing Sheets

FIG. 2

NdeI

TATG AAA CAA AGC ACT ATT GCA CTG CTC TTA CCG TTA CTG TTT ACC CCT GTG ACA AAA
AC TTT GTT TCG TGA TAA CGT GAC GAG AAT GGC AAT GAC AAA TGG GGA CAC TGT TTT
▶Met Lys Gln Ser Thr Ile Ala Leu Leu Pro Leu Leu Phe Thr Pro Val Thr Lys

KpnI    AgeI

GCC GAG GTG TGC TCT GAA CAA GCT GAG ACC GGT CCG TGC CGT GCA ATG ATC TCC CGC TGG
CGG CTC CAC ACG AGA CTT GTT CGA CTC TGG CCA GGC ACG GCA CGT TAC TAG AGG GCG ACC
▶Ala Glu Val Cys Ser Glu Gln Ala Glu Thr Gly Pro Cys Arg Ala Met Ile Ser Arg Trp

AatII

TAC TTT GAC GTC ACT GAA GGT AAG TGC GCT CCA TTC TTT TAC GGC TGC GGC GGC AAC
ATG AAA CTG CAG TGA CTT CCA TTC ACG CGA GGT AAG AAA ATG CCG ACG CCG CCG TTG
▶Tyr Phe Asp Val Thr Glu Gly Lys Cys Ala Pro Phe Phe Tyr Gly Gly Cys Gly Gly Asn

BamHI    HindIII

CGT AAC AAC TTT GAC ACT GAA GAG TAC TGC ATG GCA GTG TGC GGA TCC GCT ATT TA
GCA TTG TTG AAA CTG TGA CTT CTC ATG ACG TAC CGT CAC ACG CCT AGG CGA TAA ATT CGA
▶Arg Asn Asn Phe Asp Thr Glu Glu Tyr Cys Met Ala Val Cys Gly Ser Ala Ile

FIG. 4

XbaI | KPI (1-57) → | | | | | | | | | | | RsrII |
AgeI

```
     CTA GAT AAA AGA  GAG GTG TGC TCT GAA CAA GCT GAG ACC GGT GAG CCG TGC CGT
     TA  TTT TCT      CTC CAC ACG AGA CTT GTT CGA CTC TGG CCA CTC GGC ACG GCA
   ▶ Leu Asp Lys Arg  Glu Val Cys Ser Glu Gln Ala Glu Thr Gly Pro Cys Arg
```

```
     GCA ATG ATC TCC CGC TGG TAC TTT GAC GTC ACT GAA GGT AAG TGC GCT CCA
     CGT TAC TAG AGG GCG ACC ATG AAA CTG CAG TGA CTT CCA TTC ACG CGA GGT
   ▶ Ala Met Ile Ser Arg Trp Tyr Phe Asp Val Thr Glu Gly Lys Cys Ala Pro
```

AatII

```
     TTC TTT TAC GGC GGT TGC GGC AAC CGT AAC TTT GAC ACT GAA GAG
     AAG AAA ATG CCG CCA ACG CCG TTG GCA TTG AAA CTG TGA CTT CTC
   ▶ Phe Phe Tyr Gly Gly Cys Gly Asn Arg Asn Phe Asp Thr Glu Glu
```

BamHI            HindIII

```
     TAC TGC ATG GCA GTG TGC GGA TCC GCT ATT TA
     ATG ACG TAC CGT CAC ACG CCT AGG CGA TAA ATT CGA
   ▶ Tyr Cys Met Ala Val Cys Gly Ser Ala Ile
```

FIG. 5

XbaI  KPI (-4-57) →

```
CTA GAT AAA AGA GAG GTT GTT AGA GAG GTG TGC TCT GAA CAA GCT GAG ACC GGT
 TA TTT TCT CTC CAA CAA TCT CTC CAC ACG AGA CTT CGA CTC TGG CCA
Leu Asp Lys Arg Glu Val Val Arg Glu Val Cys Ser Glu Gln Ala Glu Thr Gly
```
                                                                    RsrII
                                                                    AgeI

```
CCG TGC CGT GCA ATG ATC TCC CGC TGG TAC TTT GAC GTC ACT GAA GGT AAG TGC
GGC ACG GCA CGT TAC TAG AGG GCG ACC ATG AAA CTG CAG TGA CTT CCA TTC ACG
Pro Cys Arg Ala Met Ile Ser Arg Trp Tyr Phe Asp Val Thr Glu Gly Lys Cys
```
                                        AatII

```
GCT CCA TTC TTT TAC GGC TGC GGT GGT CCG AAC CGT AAC AAC TTT GAC ACT GAA
CGA GGT AAG AAA ATG CCG ACG CCA CCA GGC TTG GCA TTG TTG AAA CTG TGA CTT
Ala Pro Phe Phe Tyr Gly Cys Gly Gly Pro Asn Arg Asn Asn Phe Asp Thr Glu
```
                                BamHI           HindIII

```
GAG TAC TGC ATG GCA GTG TGC GGA TCC GCT ATT TA
CTC ATG ACG TAC CGT CAC ACG CCT AGG CGA TAA ATT CGA
Glu Tyr Cys Met Ala Val Cys Gly Ser Ala Ile
```

FIG. 7

α-factor →

```
ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys
```

Xbal          KPI(-4-57)
```
GAA GAA GGG GTA TCT CTA GAT AAA AGA GAG GTT GTT AGA GAG GTG TGC TCT GAA CAA
CTT CTT CCC CAT AGA GAT CTA TTT TCT CTC CAA CAA TCT CTC CAC ACG AGA CTT GTT
▶Glu Glu Gly Val Ser Leu Asp Lys Arg Glu Val Val Arg Glu Val Cys Ser Glu Gln
```

Rsrll
        Agel                                              Aatll
```
GCT GAG ACC GGT CCG TGC CGT GCA ATG ATC TCC CGC TGG TAC TTT GAC GTC ACT GAA
CGA CTC TGG CCA GGC ACG GCA CGT TAC TAG AGG GCG ACC ATG AAA CTG CAG TGA CTT
▶Ala Glu Thr Gly Pro Cys Arg Ala Met Ile Ser Arg Trp Tyr Phe Asp Val Thr Glu GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp
```

BamHl        HindIII
```
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile
```

FIG. 8

KPI(-4-57)

Glu - Val - Val - Arg - Glu - Val - Cys - Ser - Glu - Gln - Ala
-4    -3    -2    -1     1     2     3     4     5     6     7

Glu - Thr - Gly - Pro - Cys - Arg - Ala - Met - Ile - Ser - Arg
 8     9    10    11    12    13    14    15    16    17    18

Trp - Tyr - Phe - Asp - Val - Thr - Glu - Gly - Lys - Cys - Ala
 19    20    21    22    23    24    25    26    27    28    29

Pro - Phe - Phe - Tyr - Gly - Gly - Cys - Gly - Gly - Asn - Arg
 30    31    32    33    34    35    36    37    38    39    40

Asn - Asn - Phe - Asp - Thr - Glu - Glu - Tyr - Cys - Met - Ala
 41    42    43    44    45    46    47    48    49    50    51

Val - Cys - Gly - Ser - Ala - Ile
 52    53    54    55    56    57 pTW6165

FIG. 10

α-factor

ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys

XbaI     KPI(-4-57; M15A, S17W)
GAA GAA GGG GTA TCT CTA GAT AAA AGA GAG GTT GTT AGA GAG GTG TGC TCT GAA CAA
CTT CTT CCC CAT AGA GAT CTA TTT TCT CTC CAA CAA TCT CTC CAC ACG AGA CTT GTT
▶Glu Glu Gly Val Ser Leu Asp Lys Arg Glu Val Val Arg Glu Val Cys Ser Glu Gln

RsrII
    AgeI                                                         AatII
GCT GAG ACC GGT CCG TGC CGT GCA GCT ATC TGG CGC TGG TAC TTT GAC GTC ACT GAA
CGA CTC TGG CCA GGC ACG GCA CGT CGA TAG ACC GCG ACC ATG AAA CTG CAG TGA CTT
▶Ala Glu Thr Gly Pro Cys Arg Ala Ala Ile Trp Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp

BamHI         HindIII
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile

FIG. 11

812
GTCCGTGCCGTGCAGCTATCTGGCGCTGGTACTTTGACGT
GCACGGCACGTCGATAGACCGCGACCATGAAAC
813 pTW6165 KPI(-4-57; M15A, S17F)

814
GTCCGTGCCGTGCAGCTATCTACCGCTGGTACTTTGACGT
GCACGGCACGTCGATAGATGGCGACCATGAAAC
815 pTW6166 KPI(-4-57; M15A, S17Y)

867
GTCCGTGCCGTGCATTGATCTTCCGCTGGTACTTTGACGT
GCACGGCACGTAACTAGAAGGCGACCATGAAAC
868 pTW6175 KPI(-4-57; M15L, S17F)

1493
GTCCGTGCCGTGCATTGATCTACCGCTGGTACTTTGACGT
GCACGGCACGTAACTAGATGGCGACCATGAAAC
1494 pBG028 KPI(-4-57; M15L, S17Y)

925
GTCCGTGCCGTGCAATGCACTTCCGCTGGTACTTTGACGT
GCACGGCACGTTACGTGAAGGCGACCATGAAAC
926 pTW6183 KPI(-4-57; I16H, S17F)

927
GTCCGTGCCGTGCAATGCACTACCGCTGGTACTTTGACGT
GCACGGCACGTTACGTGATGGCGACCATGAAAC
928 pTW6184 KPI(-4-57; I16H, S17Y)

929
GTCCGTGCCGTGCAATGCACTGGCGCTGGTACTTTGACGT
GCACGGCACGTTACGTGACCGCGACCATGAAAC
930 pTW6185 KPI(-4-57; I16H, S17W)

863
GTCCGTGCCGTGCAGCTCACTCCCGCTGGTACTTTGACGT
GCACGGCACGTCGAGTGAGGGCGACCATGAAAC
864 pTW6173 KPI(-4-57; M15A, I16H)

865
GTCCGTGCCGTGCATTGCACTCCCGCTGGTACTTTGACGT
GCACGGCACGTAACGTGAGGGCGACCATGAAAC
866 pTW6174 KPI(-4-57; M15L, I16H)

pTW6166

FIG. 12

α-factor
→

```
ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys
```

Xbal       KPI(-4-57; M15A, S17Y)

```
GAA GAA GGG GTA TCT CTA GAT AAA AGA│GAG GTT GTT AGA GAG GTG TGC TCT GAA CAA
CTT CTT CCC CAT AGA GAT CTA TTT TCT│CTC CAA CAA TCT CTC CAC ACG AGA CTT GTT
▶Glu Glu Gly Val Ser Leu Asp Lys Arg│Glu Val Val Arg Glu Val Cys Ser Glu Gln
```

Rsrll
Agel                                                                        Aatll

```
GCT GAG ACC GGT CCG TGC CGT GCA GCT ATC TAC CGC TGG TAC TTT GAC GTC ACT GAA
CGA CTC TGG CCA GGC ACG GCA CGT CGA TAG ATG GCG ACC ATG AAA CTG CAG TGA CTT
▶Ala Glu Thr Gly Pro Cys Arg Ala Ala Ile Tyr Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp
```

BamHI          HindIII

```
ACT GAA GAG TAC TGC ATG GCA GTG TGC GGA TCC GCT ATT AAG CTT
TGA CTT CTC ATG ACG TAC CGT CAC ACG CCT AGG CGA TAA TTC GAA
▶Thr Glu Glu Tyr Cys Met Ala Val Cys Gly Ser Ala Ile
```

FIG. 13

α-factor

→

ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys

Xbal          KPI(-4-57; M15L, S17F)

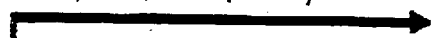

GAA GAA GGG GTA TCT CTA GAT AAA AGA GAG GTT GTT AGA GAG GTG TGC TCT GAA CAA
CTT CTT CCC CAT AGA GAT CTA TTT TCT CTC CAA CAA TCT CTC CAC ACG AGA CTT GTT
▶Glu Glu Gly Val Ser Leu Asp Lys Arg Glu Val Val Arg Glu Val Cys Ser Glu Gln

Rsrll

Agel                                                              Aatll
GCT GAG ACC GGT CCG TGC CGT GCA TTG ATC TTC CGC TGG TAC TTT GAC GTC ACT GAA
CGA CTC TGG CCA GGC ACG GCA CGT AAC TAG AAG GCG ACC ATG AAA CTG CAG TGA CTT
▶Ala Glu Thr Gly Pro Cys Arg Ala Leu Ile Phe Arg Trp Tyr Phe Asp Val Thr Glu GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp BamHI        HindIII
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile

FIG. 14 pBG028

α-factor
→

```
ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys
```

Xbal         KPI(-4-57; M15L, S17Y)
→

```
GAA GAA GGG GTA TCT CTA GAT AAA AGA|GAG GTT GTT AGA GAG GTG TGC TCT GAA CAA
CTT CTT CCC CAT AGA GAT CTA TTT TCT|CTC CAA CAA TCT CTC CAC ACG AGA CTT GTT
▶Glu Glu Gly Val Ser Leu Asp Lys Arg|Glu Val Val Arg Glu Val Cys Ser Glu Gln
```

RsrII
      AgeI                                                        AatII

```
GCT GAG ACC GGT CCG TGC CGT GCA TTG ATC TAC CGC TGG TAC TTT GAC GTC ACT GAA
CGA CTC TGG CCA GGC ACG GCA CGT AAC TAG ATG GCG ACC ATG AAA CTG CAG TGA CTT
▶Ala Glu Thr Gly Pro Cys Arg Ala Leu Ile Tyr Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp
```

BamHI         HindIII

```
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile
``` pTW6183

FIG. 15

α-factor
→

```
ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys
```

Xbal      KPI(-4-57; I16H, S17F)
→

```
GAA GAA GGG GTA TCT CTA GAT AAA AGA|GAG GTT GTT AGA GAG GTG TGC TCT GAA CAA
CTT CTT CCC CAT AGA GAT CTA TTT TCT|CTC CAA CAA TCT CTC CAC ACG AGA CTT GTT
▶Glu Glu Gly Val Ser Leu Asp Lys Arg|Glu Val Val Arg Glu Val Cys Ser Glu Gln
```

RsrII
Agel                               AatII

```
GCT GAG ACC GGT CCG TGC CGT GCA ATG CAC TTC CGC TGG TAC TTT GAC GTC ACT GAA
CGA CTC TGG CCA GGC ACG GCA CGT TAC GTG AAG GCG ACC ATG AAA CTG CAG TGA CTT
▶Ala Glu Thr Gly Pro Cys Arg Ala Met His Phe Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp
```

BamHI      HindIII

```
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile
``` pTW6184

FIG. 16

α-factor

→

ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▸Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▸Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▸Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▸Ser Thr Asn Asn Gly Leu Leu Phe Ile Asn Thr Thr Ile Ala Ser Ile Ala Ala Lys

Xbal               KPI(-4-57; I16H, S17Y)

GAA GAA GGG GTA TCT CTA GAT AAA AGA | GAG GTT GTT AGA GAG GTG TGC TCT GAA CAA
CTT CTT CCC CAT AGA GAT CTA TTT TCT | CTC CAA CAA TCT CTC CAC ACG AGA CTT GTT
▸Glu Glu Gly Val Ser Leu Asp Lys Arg | Glu Val Val Arg Glu Val Cys Ser Glu Gln

RsrII
             AgeI                                                      AatII

GCT GAG ACC GGT CCG TGC CGT GCA ATG <u>CAC</u> <u>TAC</u> CGC TGG TAC TTT GAC GTC ACT GAA
CGA CTC TGG CCA GGC ACG GCA CGT TAC <u>GTG</u> <u>ATG</u> GCG ACC ATG AAA CTG CAG TGA CTT
▸Ala Glu Thr Gly Pro Cys Arg Ala Met His Tyr Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▸Gly Lys Cys Ala Pro Phe Phe Tyr Gly Gly Cys Gly Gly Asn Arg Asn Asn Phe Asp

BamHI         HindIII

ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▸Thr Glu Glu Tyr Cys Met Ala Val Cys Gly Ser Ala Ile pTW6185

FIG. 17

α-factor →

```
ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys
```

Xbal      KPI(-4-57; 116H, S17W) →

```
GAA GAA GGG GTA TCT CTA GAT AAA AGA|GAG GTT GTT AGA GAG GTG TGC TCT GAA CAA
CTT CTT CCC CAT AGA GAT CTA TTT TCT|CTC CAA CAA TCT CTC CAC ACG AGA CTT GTT
▶Glu Glu Gly Val Ser Leu Asp Lys Arg|Glu Val Val Arg Glu Val Cys Ser Glu Gln
```

RsrII
Agel                                                        AatII

```
GCT GAG ACC GGT CCG TGC CGT GCA ATG CAC TGG CGC TGG TAC TTT GAC GTC ACT GAA
CGA CTC TGG CCA GGC ACG GCA CGT TAC GTG ACC GCG ACC ATG AAA CTG CAG TGA CTT
▶Ala Glu Thr Gly Pro Cys Arg Ala Met His Trp Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp
```

BamHI          HindIII

```
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile
```

FIG. 18 pTW6173

α-factor
→

```
ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys
```

Xbal            KPI(-4-57; M15A, I16H)

```
GAA GAA GGG GTA TCT CTA GAT AAA AGA|GAG GTT GTT AGA GAG GTG TGC TCT GAA CAA
CTT CTT CCC CAT AGA GAT CTA TTT TCT|CTC CAA CAA TCT CTC CAC ACG AGA CTT GTT
▶Glu Glu Gly Val Ser Leu Asp Lys Arg|Glu Val Val Arg Glu Val Cys Ser Glu Gln
```

RsrII
AgeI                                                        AatII

```
GCT GAG ACC GGT CCG TGC CGT GCA GCT CAC TCC CGC TGG TAC TTT GAC GTC ACT GAA
CGA CTC TGG CCA GGC ACG GCA CGT CGA GTG AGG GCG ACC ATG AAA CTG CAG TGA CTT
▶Ala Glu Thr Gly Pro Cys Arg Ala Ala His Ser Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp
```

BamHI          HindIII

```
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile
``` pTW6174

FIG. 19

α-factor
→

ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys

Xbal          KPI(-4-57; M15L, I16H)
                                  →

GAA GAA GGG GTA TCT CTA GAT AAA AGA|GAG GTT GTT AGA GAG GTG TGC TCT GAA CAA
CTT CTT CCC CAT AGA GAT CTA TTT TCT|CTC CAA CAA TCT CTC CAC ACG AGA CTT GTT
▶Glu Glu Gly Val Ser Leu Asp Lys Arg|Glu Val Val Arg Glu Val Cys Ser Glu Gln

Rsrll
      Agel                                                      Aatll
GCT GAG ACC GGT CCG TGC CGT GCA TTG CAC TCC CGC TGG TAC TTT GAC GTC ACT GAA
CGA CTC TGG CCA GGC ACG GCA CGT AAC GTG AGG GCG ACC ATG AAA CTG CAG TGA CTT
▶Ala Glu Thr Gly Pro Cys Arg Ala Leu His Ser Arg Trp Tyr Phe Asp Val Thr Glu GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp BamHI         HindIII
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile

FIG. 20

KPI(-4-57; M15A, S17W)    TW6165

Glu - Val - Val - Arg - Glu - Val - Cys - Ser - Glu - Gln - Ala
-4    -3    -2    -1     1     2     3     4     5     6     7

Glu - Thr - Gly - Pro - Cys - Arg - Ala - Ala - Ile - Trp - Arg
 8     9    10    11    12    13    14    15    16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 21

KPI(-4-57; M15A, S17Y)   TW6166

| | | | | | | | |
|---|---|---|---|---|---|---|---|
| Glu<br>-4 | Val<br>-3 | Val<br>-2 | Arg<br>-1 | Glu<br>1 | Val<br>2 | Cys<br>3 | Ser<br>4 | Glu<br>5 | Gln<br>6 | Ala<br>7 |

Glu - Thr - Gly - Pro - Cys - Arg - Ala - <u>Ala</u> - Ile - <u>Tyr</u> - Arg
 8      9    10    11    12    13    14    15     16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 22

KPI(-4-57; M15L, S17F)  TW6175

Glu - Val - Val - Arg - Glu - Val - Cys - Ser - Glu - Gln - Ala
-4    -3    -2    -1     1     2     3     4     5     6     7

Glu - Thr - Gly - Pro - Cys - Arg - Ala - Leu - Ile - Phe - Arg
 8     9    10    11    12    13    14    15    16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 23

KPI(-4-57; M15L, S17Y)    BG028

Glu - Val - Val - Arg - Glu - Val - Cys - Ser - Glu - Gln - Ala
-4    -3    -2    -1     1     2     3     4     5     6     7

Glu - Thr - Gly - Pro - Cys - Arg - Ala - Leu - Ile - Tyr - Arg
 8     9    10    11    12    13    14    15    16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 24

KPI(-4-57; I16H, S17F)    TW6183

| Glu | - | Val | - | Val | - | Arg | - | Glu | - | Val | - | Cys | - | Ser | - | Glu | - | Gln | - | Ala |
|-----|---|-----|---|-----|---|-----|---|-----|---|-----|---|-----|---|-----|---|-----|---|-----|---|-----|
| -4  |   | -3  |   | -2  |   | -1  |   | 1   |   | 2   |   | 3   |   | 4   |   | 5   |   | 6   |   | 7   |

Glu - Thr - Gly - Pro - Cys - Arg - Ala - Met - His - Phe - Arg
 8     9    10    11    12    13    14    15    16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 25

KPI(-4-57; I16H, S17Y)    TW6184

Glu - Val - Val - Arg - Glu - Val - Cys - Ser - Glu - Gln - Ala
-4    -3    -2    -1     1     2     3     4     5     6     7

Glu - Thr - Gly - Pro - Cys - Arg - Ala - Met - <u>His</u> - <u>Tyr</u> - Arg
 8     9    10    11    12    13    14    15    16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 26

KPI(-4-57; I16H, S17W)    TW6185

Glu - Val - Val - Arg - Glu - Val - Cys - Ser - Glu - Gln - Ala
-4    -3    -2    -1    1     2     3     4     5     6     7

Glu - Thr - Gly - Pro - Cys - Arg - Ala - Met - <u>His</u> - <u>Trp</u> - Arg
8     9     10    11    12    13    14    15    16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 27

KPI(-4-57; M15A, S17F)     DD185

Glu - Val - Val - Arg - Glu - Val - Cys - Ser - Glu - Gln - Ala
-4    -3    -2    -1     1     2     3     4     5     6     7

Glu - Thr - Gly - Pro - Cys - Arg - Ala - Ala - Ile - <u>Phe</u> - Arg
 8     9    10    11    12    13    14    <u>15</u>    16    17    18

Trp - Tyr - Phe - Asp - Val - Thr - Glu - Gly - Lys - Cys - Ala
19    20    21    22    23    24    25    26    27    28    29

Pro - Phe - Phe - Tyr - Gly - Gly - Cys - Gly - Gly - Asn - Arg
30    31    32    33    34    35    36    37    38    39    40

Asn - Asn - Phe - Asp - Thr - Glu - Glu - Tyr - Cys - Met - Ala
41    42    43    44    45    46    47    48    49    50    51

Val - Cys - Gly - Ser - Ala - Ile
52    53    54    55    56    57

FIG. 28

KPI(-4-57; M15A, I16H) TW6173

| Glu -4 | Val -3 | Val -2 | Arg -1 | Glu 1 | Val 2 | Cys 3 | Ser 4 | Glu 5 | Gln 6 | Ala 7 |
|---|---|---|---|---|---|---|---|---|---|---|
| Glu 8 | Thr 9 | Gly 10 | Pro 11 | Cys 12 | Arg 13 | Ala 14 | Ala 15 | His 16 | Ser 17 | 18 |
| Trp 19 | Tyr 20 | Phe 21 | Asp 22 | Val 23 | Thr 24 | Glu 25 | Gly 26 | Lys 27 | Cys 28 | Ala 29 |
| Pro 30 | Phe 31 | Phe 32 | Tyr 33 | Gly 34 | Gly 35 | Cys 36 | Gly 37 | Gly 38 | Asn 39 | Arg 40 |
| Asn 41 | Asn 42 | Phe 43 | Asp 44 | Thr 45 | Glu 46 | Glu 47 | Tyr 48 | Cys 49 | Met 50 | Ala 51 |
| Val 52 | Cys 53 | Gly 54 | Ser 55 | Ala 56 | Ile 57 | | | | | |

FIG. 29

KPI(-4-57; M15L, I16H)  TW6174

Glu - Val - Val - Arg - Glu - Val - Cys - Ser - Glu - Gln - Ala
-4    -3    -2    -1     1     2     3     4     5     6     7

Glu - Thr - Gly - Pro - Cys - Arg - Ala - Leu - His - Ser - Arg
 8     9    10    11    12    13    14    15    16    17    18

Trp - Tyr - Phe - Asp - Val - Thr - Glu - Gly - Lys - Cys - Ala
 19    20    21    22    23    24    25    26    27    28    29

Pro - Phe - Phe - Tyr - Gly - Gly - Cys - Gly - Gly - Asn - Arg
 30    31    32    33    34    35    36    37    38    39    40

Asn - Asn - Phe - Asp - Thr - Glu - Glu - Tyr - Cys - Met - Ala
 41    42    43    44    45    46    47    48    49    50    51

Val - Cys - Gly - Ser - Ala - Ile
 52    53    54    55    56    57

FIG. 38 phoA signal →

```
GTG AAA CAA AGC ACT ATT GCA CTG GCA CTC TTA CCG TTA CTG TTT ACC CCG GTG ACC AAA
Val Lys Gln Ser Thr Ile Ala Leu Ala Leu Leu Pro Leu Leu Phe Thr Pro Val Thr Lys
```

KPI (1-55) →     AgeI     BstEII

```
GCC GAG GTG TGC TCT GAA CAA GCT GAG ACC GGT CCG TGC CGT GCA ATG ATC TCC CGC TGG
Ala Glu Val Cys Ser Glu Gln Ala Glu Thr Gly Pro Cys Arg Ala Met Ile Ser Arg Trp
```

AatII

```
TAC TTT GAC GTC ACT GAA GGT AAG TGC GCT CCA TTC TTT TAC GGC GGT TGC GGC GGC AAC
Tyr Phe Asp Val Thr Glu Gly Lys Cys Ala Pro Phe Phe Tyr Gly Gly Cys Gly Gly Asn
```

BamHI   gIII →

```
CGT AAC AAC TTT GAC ACT GAA GAG TAC TGC ATG GCA GTG TGC GGA TCC GGT GGT GGC TCT
Arg Asn Asn Phe Asp Thr Glu Glu Tyr Cys Met Ala Val Cys Gly Ser Gly Gly Gly Ser
```

```
GGT TCC GGT GAT TTT GAT TAT GAA AAG ATG GCA AAC GCT AAT AAG GGG GCT ATG ACC GAA
Gly Ser Gly Asp Phe Asp Tyr Glu Lys Met Ala Asn Ala Asn Lys Gly Ala Met Thr Glu
```

```
AAT GCC GAT GAA AAC GCG CTA CAG TCT GAC GCT AAA GGC AAA CTT GAT TCT GTC GCT ACT
Asn Ala Asp Glu Asn Ala Leu Gln Ser Asp Ala Lys Gly Lys Leu Asp Ser Val Ala Thr
```

```
GAT TAC GGT GCT GCT ATC GAT GGT TTC ATT GGT GAC GTT TCC GGC CTT GCT AAT GGT AAT
Asp Tyr Gly Ala Ala Ile Asp Gly Phe Ile Gly Asp Val Ser Gly Leu Ala Asn Gly Asn
```

```
GGT GCT ACT GGT GAT TTT GCT GGC TCT AAT TCC CAA ATG GCT CAA GTC GGT GAC GGT GAT
Gly Ala Thr Gly Asp Phe Ala Gly Ser Asn Ser Gln Met Ala Gln Val Gly Asp Gly Asp
```

```
AAT TCA CCT TTA ATG AAT AAT TTC CGT CAA TAT TTA CCT TCC CTC CCT CAA TCG GTT GAA
Asn Ser Pro Leu Met Asn Asn Phe Arg Gln Tyr Leu Pro Ser Leu Pro Gln Ser Val Glu
```

```
TGT CGC CCT TTT GTC TTT GGC GCT GGT AAA CCA TAC GAA TTT TCT ATT GAT TGT GAC AAA
Cys Arg Pro Phe Val Phe Gly Ala Gly Lys Pro Tyr Glu Phe Ser Ile Asp Cys Asp Lys
```

```
ATA AAC TTA TTC CGT GGT GTC TTT GCG TTT CTT TTA TAT GTT GCC ACC TTT ATG TAT GTA
Ile Asn Leu Phe Arg Gly Val Phe Ala Phe Leu Leu Tyr Val Ala Thr Phe Met Tyr Val
```

```
TTT TCT ACG TTT GCT AAC ATA CTG CGT AAT AAG GAG TCT TAA TA
Phe Ser Thr Phe Ala Asn Ile Leu Arg Asn Lys Glu Ser ...
```

FIG. 41 phoA signal →

BstEII

GTG AAA CAA AGC ACT ATT GCA CTG GCA CTC TTA CCG TTA CTG TTT ACC CCG GTG ACC AAA
▸Val Lys Gln Ser Thr Ile Ala Leu Ala Leu Leu Pro Leu Leu Phe Thr Pro Val Thr Lys

KPI (1-55; 16-19) → AgeI          16-19

GCC|GAG GTG TGC TCT GAA CAA GCT GAG ACC GGT CCG TGC CGT NNS NNS NNS NNS TGG TAC
▸Ala|Glu Val Cys Ser Glu Gln Ala Glu Thr Gly Pro Cys Arg --- --- --- --- Trp Tyr

AatII

TTT GAC GTC ACT GAA GGT AAG TGC GCT CCA TTC TTT TAC GGC GGT TGC GGC GGC AAC CGT
▸Phe Asp Val Thr Glu Gly Lys Cys Ala Pro Phe Phe Tyr Gly Gly Cys Gly Gly Asn Arg

BamHI      gIII →

AAC AAC TTT GAC ACT GAA GAG TAC TGC ATG GCA GTG TGC GGA TCC|GGT GGT GGC TCT GGT
▸Asn Asn Phe Asp Thr Glu Glu Tyr Cys Met Ala Val Cys Gly Ser|Gly Gly Gly Ser Gly

TCC GGT GAT TTT GAT TAT GAA AAG ATG GCA AAC GCT AAT AAG GGG GCT ATG ACC GAA AAT
▸Ser Gly Asp Phe Asp Tyr Glu Lys Met Ala Asn Ala Asn Lys Gly Ala Met Thr Glu Asn

GCC GAT GAA AAC GCG CTA CAG TCT GAC GCT AAA GGC AAA CTT GAT TCT GTC GCT ACT GAT
▸Ala Asp Glu Asn Ala Leu Gln Ser Asp Ala Lys Gly Lys Leu Asp Ser Val Ala Thr Asp

TAC GGT GCT GCT ATC GAT GGT TTC ATT GGT GAC GTT TCC GGC CTT GCT AAT GGT AAT GGT
▸Tyr Gly Ala Ala Ile Asp Gly Phe Ile Gly Asp Val Ser Gly Leu Ala Asn Gly Asn Gly gIII

GCT ACT GGT GAT TTT GCT GGC TCT AAT TCC CAA ATG GCT CAA GTC GGT GAC GGT GAT AAT
▸Ala Thr Gly Asp Phe Ala Gly Ser Asn Ser Gln Met Ala Gln Val Gly Asp Gly Asp Asn

TCA CCT TTA ATG AAT AAT TTC CGT CAA TAT TTA CCT TCC CTC CCT CAA TCG GTT GAA TGT
▸Ser Pro Leu Met Asn Asn Phe Arg Gln Tyr Leu Pro Ser Leu Pro Gln Ser Val Glu Cys

CGC CCT TTT GTC TTT GGC GCT GGT AAA CCA TAC GAA TTT TCT ATT GAT TGT GAC AAA ATA
▸Arg Pro Phe Val Phe Gly Ala Gly Lys Pro Tyr Glu Phe Ser Ile Asp Cys Asp Lys Ile

AAC TTA TTC CGT GGT GTC TTT GCG TTT CTT TTA TAT GTT GCC ACC TTT ATG TAT GTA TTT
▸Asn Leu Phe Arg Gly Val Phe Ala Phe Leu Leu Tyr Val Ala Thr Phe Met Tyr Val Phe

TCT ACG TTT GCT AAC ATA CTG CGT AAT AAG GAG TCT TAA TA
▸Ser Thr Phe Ala Asn Ile Leu Arg Asn Lys Glu Ser •••

FIG. 42 phoA signal →

BstEII

GTG AAA CAA AGC ACT ATT GCA CTG GCA CTC TTA CCG TTA CTG TTT ACC CCG GTG ACC AAA
▸Val Lys Gln Ser Thr Ile Ala Leu Ala Leu Leu Pro Leu Leu Phe Thr Pro Val Thr Lys

KPI (1-55; M15A, S17F) → AgeI

GCC|GAG GTG TGC TCT GAA CAA GCT GAG ACC GGT CCG TGC CGT GCA GCT ATC TTC CGC TGG
▸Ala|Glu Val Cys Ser Glu Gln Ala Glu Thr Gly Pro Cys Arg Ala Ala Ile Phe Arg Trp

AatII

TAC TTT GAC GTC ACT GAA GGT AAG TGC GCT CCA TTC TTT TAC GGC GGT TGC GGC GGC AAC
▸Tyr Phe Asp Val Thr Glu Gly Lys Cys Ala Pro Phe Phe Tyr Gly Gly Cys Gly Gly Asn

BamHI  gIII →

CGT AAC AAC TTT GAC ACT GAA GAG TAC TGC ATG GCA GTG TGC GGA TCC|GGT GGT GGC TCT
▸Arg Asn Asn Phe Asp Thr Glu Glu Tyr Cys Met Ala Val Cys Gly Ser|Gly Gly Gly Ser

GGT TCC GGT GAT TTT GAT TAT GAA AAG ATG GCA AAC GCT AAT AAG GGG GCT ATG ACC GAA
▸Gly Ser Gly Asp Phe Asp Tyr Glu Lys Met Ala Asn Ala Asn Lys Gly Ala Met Thr Glu

AAT GCC GAT GAA AAC GCG CTA CAG TCT GAC GCT AAA GGC AAA CTT GAT TCT GTC GCT ACT
▸Asn Ala Asp Glu Asn Ala Leu Gln Ser Asp Ala Lys Gly Lys Leu Asp Ser Val Ala Thr

GAT TAC GGT GCT GCT ATC GAT GGT TTC ATT GGT GAC GTT TCC GGC CTT GCT AAT GGT AAT
▸Asp Tyr Gly Ala Ala Ile Asp Gly Phe Ile Gly Asp Val Ser Gly Leu Ala Asn Gly Asn

GGT GCT ACT GGT GAT TTT GCT GGC TCT AAT TCC CAA ATG GCT CAA GTC GGT GAC GGT GAT
▸Gly Ala Thr Gly Asp Phe Ala Gly Ser Asn Ser Gln Met Ala Gln Val Gly Asp Gly Asp

AAT TCA CCT TTA ATG AAT AAT TTC CGT CAA TAT TTA CCT TCC CTC CCT CAA TCG GTT GAA
▸Asn Ser Pro Leu Met Asn Asn Phe Arg Gln Tyr Leu Pro Ser Leu Pro Gln Ser Val Glu

TGT CGC CCT TTT GTC TTT GGC GCT GGT AAA CCA TAC GAA TTT TCT ATT GAT TGT GAC AAA
▸Cys Arg Pro Phe Val Phe Gly Ala Gly Lys Pro Tyr Glu Phe Ser Ile Asp Cys Asp Lys

ATA AAC TTA TTC CGT GGT GTC TTT GCG TTT CTT TTA TAT GTT GCC ACC TTT ATG TAT GTA
▸Ile Asn Leu Phe Arg Gly Val Phe Ala Phe Leu Leu Tyr Val Ala Thr Phe Met Tyr Val

TTT TCT ACG TTT GCT AAC ATA CTG CGT AAT AAG GAG TCT TAA TA
▸Phe Ser Thr Phe Ala Asn Ile Leu Arg Asn Lys Glu Ser pDD185

FIG. 44

α-factor →

```
ATG AGA TTT CCT TCA ATT TTT ACT GCA GTT TTA TTC GCA GCA TCC TCC GCA TTA GCT
TAC TCT AAA GGA AGT TAA AAA TGA CGT CAA AAT AAG CGT CGT AGG AGG CGT AAT CGA
▶Met Arg Phe Pro Ser Ile Phe Thr Ala Val Leu Phe Ala Ala Ser Ser Ala Leu Ala

GCT CCA GTC AAC ACT ACA ACA GAA GAT GAA ACG GCA CAA ATT CCG GCT GAA GCT GTC
CGA GGT CAG TTG TGA TGT TGT CTT CTA CTT TGC CGT GTT TAA GGC CGA CTT CGA CAG
▶Ala Pro Val Asn Thr Thr Thr Glu Asp Glu Thr Ala Gln Ile Pro Ala Glu Ala Val

ATC GGT TAC TTA GAT TTA GAA GGG GAT TTC GAT GTT GCT GTT TTG CCA TTT TCC AAC
TAG CCA ATG AAT CTA AAT CTT CCC CTA AAG CTA CAA CGA CAA AAC GGT AAA AGG TTG
▶Ile Gly Tyr Leu Asp Leu Glu Gly Asp Phe Asp Val Ala Val Leu Pro Phe Ser Asn

AGC ACA AAT AAC GGG TTA TTG TTT ATA AAT ACT ACT ATT GCC AGC ATT GCT GCT AAA
TCG TGT TTA TTG CCC AAT AAC AAA TAT TTA TGA TGA TAA CGG TCG TAA CGA CGA TTT
▶Ser Thr Asn Asn Gly Leu Leu Phe Ile Asn Thr Thr Ile Ala Ser Ile Ala Ala Lys
```

Xbal          KPI(-4-57; M15A, S17F) →

```
GAA GAA GGG GTA TCT CTA GAT AAA AGA|GAG GTT GTT AGA GAG GTG TGC TCT GAA CAA
CTT CTT CCC CAT AGA GAT CTA TTT TCT|CTC CAA CAA TCT CTC CAC ACG AGA CTT GTT
▶Glu Glu Gly Val Ser Leu Asp Lys Arg|Glu Val Val Arg Glu Val Cys Ser Glu Gln
```

RsrII

AgeI                                                 AatII

```
GCT GAG ACC GGT CCG TGC CGT GCA GCT ATC TTC CGC TGG TAC TTT GAC GTC ACT GAA
CGA CTC TGG CCA GGC ACG GCA CGT CGA TAG AAG GCG ACC ATG AAA CTG CAG TGA CTT
▶Ala Glu Thr Gly Pro Cys Arg Ala Ala Ile Phe Arg Trp Tyr Phe Asp Val Thr Glu

GGT AAG TGC GCT CCA TTC TTT TAC GGC GGT TGC GGC GGC AAC CGT AAC AAC TTT GAC
CCA TTC ACG CGA GGT AAG AAA ATG CCG CCA ACG CCG CCG TTG GCA TTG TTG AAA CTG
▶Gly Lys Cys Ala Pro Phe Phe Tyr Gly Gly Cys Gly Gly Asn Arg Asn Asn Phe Asp
```

BamHI       HindIII

```
ACT GAA GAG TAC TGC ATG GCA GTG TGC GGA TCC GCT ATT TAA GCT T
TGA CTT CTC ATG ACG TAC CGT CAC ACG CCT AGG CGA TAA ATT CGA A
▶Thr Glu Glu Tyr Cys Met Ala Val Cys Gly Ser Ala Ile
```

FIG. 45

Plasma kallikrein inhibition by KPI (-4-57) variants

| Variant | | Substitution 15 | 16 | 17 | $K_i(nM)$ |
|---|---|---|---|---|---|
| TW113 | KPI (-4-57) | | | | 45.00 |
| DD185 | KPI (-4-57; M15A, S17F) | A | | F | 0.39 |
| TW6165 | KPI (-4-57; M15A, S17W) | A | | W | 0.65 |
| TW6166 | KPI (-4-57; M15A, S17Y) | A | | Y | 0.40 |
| TW6175 | KPI (-4-57; M15L, S17F) | L | | F | 0.50 |
| BG028 | KPI (-4-57; M15L, S17Y) | L | | Y | 1.10 |
| TW6183 | KPI (-4-57; I16H, S17F) | | H | F | 1.20 |
| TW6184 | KPI (-4-57; I16H, S17Y) | | H | Y | 0.91 |
| TW6185 | KPI (-4-57; I16H, S17W) | | H | W | 1.30 |
| TW6173 | KPI (-4-57; M15A, I16H) | A | H | | 1.00 |
| TW6174 | KPI (-4-57; M15L, I16H) | L | H | | 0.90 |

FIG. 46A

| Variant | Sequence | Inhibition Ki (nM) | | | |
|---|---|---|---|---|---|
| | | Kallikrein | Plasmin | XIIa | Xa |
| Aprotinin | RPDFCLEPPYTGPCKARIIRYFYNAKAGLCQTFVYGGCRAKRNNFKSAEDCMRTCGGA | 20.00 | 0.23 | 5000.0 | |
| Aprotinin R15, S42 | DFCLEPPYTGPCRARIIRYFYNAKAGLCQTFVYGGCRAKSNNFKSAEDCMRTCGGA | 0.91 | 0.17 | 3983.0 | |
| KPI(-4-57) | EVVREVCSEQAETGPCRAMISRWYFDVTEGKCAPFFYGGCGGNRNNFDTEEYCMAVCGSAI | 45.00 | 34.00 | 3718.0 | 161.0 |
| TW6167 | EVVREVCSEQAEPGPCRAMISRWYFDVTEGKCAPFFYGGCGGNRNNFDTEEYCMAVCGSAI | 61.00 | | 3641.0 | 288.0 |
| BG031 | EVVREVCSEQAEVGPCRARISRWYFDVTEGKCAPFFYGGCGGNRNNFDTEEYCMAVCGSAI | 34.00 | | 498.0 | |
| BG032 | EVVREVCSEQAESGPCRAAISRWYFDVTEGKCAPFFYGGCGGNRNNFDTEEYCMAVCGSAI | 49.00 | | 731.0 | |
| TW101 | EVCSEQAETGPCKAMISRWYFDVTEGKCAPFFYGGCGGNRNNFDTEEYCMAVCGSAI | 2000.00 | 11.50 | | |
| TW6208 | EVCSEQAETGPCRGMISRWYFDVTEGKCAPFFYGGCGGNRNNFDTEEYCMAVCGSAI | | | 369.0 | |
| TW106 | EVVREVCSEQAETGPCRARISRWYFDVTEGKCAPFFYGGCGGNRNNFDTEEYCMAVCGSAI | 560.00 | 3.70 | | |
| DD108 | EVVREVCSEQAETGPCRAAISRWYFDVTEGKCAPFFYGGCGGNRNNFDTEEYCMAVCGSAI | 1.70 | 11.20 | 1600.0 | 123.0 |
| DD109 | EVVREVCSEQAETGPCRAIISRWYFDVTEGKCAPFFYGGCGGNRNNFDTEEYCMAVCGSAI | 9.50 | | 1681.0 | 421.0 |
| DD110 | EVVREVCSEQAETGPCRALISRWYFDVTEGKCAPFFYGGCGGNRNNFDTEEYCMAVCGSAI | 2.10 | | 624.0 | 55.0 |
| DD111 | EVVREVCSEQAETGPCRASISRWYFDVTEGKCAPFFYGGCGGNRNNFDTEEYCMAVCGSAI | 5.60 | | | |
| DD112 | EVVREVCSEQAETGPCRAVISRWYFDVTEGKCAPFFYGGCGGNRNNFDTEEYCMAVCGSAI | 6.80 | | 998.0 | |
| TW6179 | EVVREVCSEQAETGPCRAGISRWYFDVTEGKCAPFFYGGCGGNRNNFDTEEYCMAVCGSAI | 78.00 | | 368.0 | |
| TW6163 | EVVREVCSEQAETGPCRAMHSRWYFDVTEGKCAPFFYGGCGGNRNNFDTEEYCMAVCGSAI | 4.70 | 103.58 | 4532.0 | 457.0 |
| TW6172 | EVVREVCSEQAETGPCRAMASRWYFDVTEGKCAPFFYGGCGGNRNNFDTEEYCMAVCGSAI | 315.00 | | | 1463.0 |
| TW6180 | EVVREVCSEQAETGPCRAMFSRWYFDVTEGKCAPFFYGGCGGNRNNFDTEEYCMAVCGSAI | 70.00 | | 885.0 | 39.0 |
| TW6181 | EVVREVCSEQAETGPCRAMKSRWYFDVTEGKCAPFFYGGCGGNRNNFDTEEYCMAVCGSAI | 150.00 | | 1514.0 | |
| BG001 | EVVREVCSEQAETGPCRAMLSRWYFDVTEGKCAPFFYGGCGGNRNNFDTEEYCMAVCGSAI | 38.00 | 10.00 | 489.0 | 204.0 |
| TW116 | EVCSEQAETGPCRAMIIRWYFDVTEGKCAPFFYGGCGGNRNNFDTEEYCMAVCGSAI | 145.00 | 89.00 | | 806.0 |
| DD102 | EVVREVCSEQAETGPCRAMIPRWYFDVTEGKCAPFFYGGCGGNRNNFDTEEYCMAVCGSAI | 16.00 | | 315.0 | |
| DD103 | EVVREVCSEQAETGPCRAMIFRWYFDVTEGKCAPFFYGGCGGNRNNFDTEEYCMAVCGSAI | 17.00 | | 2128.0 | 110.0 |

FIG. 46B

| | | | | |
|---|---|---|---|---|
| DD104 | EVVREVCSEQAETGPCRAMIYRWYFDVTEGKCAPFFYGGCGGNRNNFDTEEYCMAVCGSAI | 15.00 | 237.0 | 345.0 |
| DD105 | EVVREVCSEQAETGPCRAMIWRWYFDVTEGKCAPFFYGGCGGNRNNFDTEEYCMAVCGSAI | 18.00 | 198.0 | 320.0 |
| TW6168 | EVVREVCSEQAETGPCRAMILRWYFDVTEGKCAPFFYGGCGGNRNNFDTEEYCMAVCGSAI | 25.80 | 3521.0 | 395.0 |
| TW6182 | EVVREVCSEQAETGPCRAMIHRWYFDVTEGKCAPFFYGGCGGNRNNFDTEEYCMAVCGSAI | 36.00 | 752.0 | |
| TW6194 | EVVREVCSEQAETGPCRAMIERWYFDVTEGKCAPFFYGGCGGNRNNFDTEEYCMAVCGSAI | 70.83 | | |
| TW6210 | EVVREVCSEQAETGPCRAMIQRWYFDVTEGKCAPFFYGGCGGNRNNFDTEEYCMAVCGSAI | 54.00 | 277.0 | |
| CL006 | EVVREVCSEQAETGPCRAMISAWYFDVTEGKCAPFFYGGCGGNRNNFDTEEYCMAVCGSAI | 110.20 | 89600.0 | 133.0 |
| BG012 | EVVREVCSEQAETGPCRAMISTWYFDVTEGKCAPFFYGGCGGNRNNFDTEEYCMAVCGSAI | | 40.0 | 116.0 |
| TW6209 | EVVREVCSEQAETGPCRAMISHWYFDVTEGKCAPFFYGGCGGNRNNFDTEEYCMAVCGSAI | 81.00 | 45.90 | 184.0 | 613.0 |
| TW6211 | EVVREVCSEQAETGPCRAMISKWYFDVTEGKCAPFFYGGCGGNRNNFDTEEYCMAVCGSAI | 184.00 | | 402.0 | |
| DD128 | EVVREVCSEQAETGPCRAMISLWYFDVTEGKCAPFFYGGCGGNRNNFDTEEYCMAVCGSAI | 44.00 | | 37.0 |
| TW6142 | EVVREVCSEQAETGPCRAMISRWYFDVTEGKCAPFFYGGCGGNRNNFDTEEYCMAVCGSAI | 18.00 | 18.00 | 7972.0 | 225.0 |
| AL301 | EVVREVCSEQAETGPCRAMISRWYFDVTEGKCAPFFYGGCGGNRNNFDTEEYCMAVCGSAI | 216.00 | 1557.0 | |
| AL302 | EVVREVCSEQAETGPCRAMISRWYFDVTEGKCAPFFYGGCGGNRNNFDTEEYCMAVCGSAI | 39.00 | | 316.0 |
| TW6147 | EVVREVCSEQAETGPCRAMISRWYFDVTEGKCAPFFYGGCAGNRNNFDTEEYCMAVCGSAI | 35.00 | 1090.0 | 179.0 |
| TW6138 | EVVREVCSEQAETGPCRAMISRWYFDVTEGKCAPFFYGGCKGNRNNFDTEEYCMAVCGSAI | 18.00 | 921.0 | 309.0 |
| TW6154 | EVVREVCSEQAETGPCRAMISRWYFDVTEGKCAPFFYGGCLGNRNNFDTEEYCMAVCGSAI | 11.00 | 915.0 | 39.0 |
| TW6155 | EVVREVCSEQAETGPCRAMISRWYFDVTEGKCAPFFYGGCMGNRNNFDTEEYCMAVCGSAI | 11.00 | | 27.0 |
| TW6140 | EVVREVCSEQAETGPCRAMISRWYFDVTEGKCAPFFYGGCNGNRNNFDTEEYCMAVCGSAI | 35.00 | 475.0 | |
| TW6156 | EVVREVCSEQAETGPCRAMISRWYFDVTEGKCAPFLYGGCGGNRNNFDTEEYCMAVCGSAI | | | |
| TW6141 | EVVREVCSEQAETGPCRAMISRWYFDVTEGKCAPFGYGGCQGNRNNFDTEEYCMAVCGSAI | 42.00 | | |
| TW118 | EVVREVCSEQAETGPCRAMISRWYFDVTEGKCAPFFYGGCRGNRNNFDTEEYCMAVCGSAI | 6.00 | 24.00 | 13009.0 | 68.0 |
| DD100 | EVVREVCSEQAETGPCRAMISRWYFDVTEGKCAPFFYGGCCGNRNNFDTEEYCMAVCGSAI | 15.00 | | |
| TW6157 | EVVREVCSEQAETGPCRAMISRWYFDVTEGKCAPFFYGGCSGNRNNFDTEEYCMAVCGSAI | 40.00 | 511.0 | 168.0 |
| TW6158 | EVVREVCSEQAETGPCRAMISRWYFDVTEGKCAPFFYGGCTGNRNNFDTEEYCMAVCGSAI | 29.00 | | |
| TW6159 | EVVREVCSEQAETGPCRAMISRWYFDVTEGKCAPFFYGGCVGNRNNFDTEEYCMAVCGSAI | 17.00 | | 64.0 |

FIG. 46C

| ID | Sequence | | | | |
|---|---|---|---|---|---|
| TW6161 | EVVREVCSEQAETGPCRAMISRWYFDVTEGKCAPFFYGGCYGNRNNFDTEEYCMAVCGSAI | 7.50 | 18.00 | 1507.0 | 8.7 |
| DD101 | EVVREVCSEQAETGPCRAMISRWYFDVTEGKCAPFFYGGCEGNRNNFDTEEYCMAVCGSAI | 64.00 | | 924.0 | 954.0 |
| TW6151 | EVVREVCSEQAETGPCRAMISRWYFDVTEGKCAPFFYGGCHGNRNNFDTEEYCMAVCGSAI | 163.00 | 22.80 | 1162.0 | 78.0 |
| TW6139 | EVVRREVCSEQAETGPCRAMISRWYFDVTEGKCAPFFYGGCIGNRNNFDTEEYCMAVCGSAI | 19.00 | 21.30 | 152.0 | 36.0 |
| TW6153 | EVVRREVCSEQAETGPCRAMISRWYFDVTEGKCAPFFYGCCIGNRNNFDTEEYCMAVCGSAI | 11.20 | 27.00 | 65.0 | |
| TW122 | EVCSEQAETGPCRAMISRWYFDVTEGKCAPFFYGGCANRNNFDTEEYCMAVCGSAI | 32.00 | | 444.0 | 581.0 |
| TW6178 | EVVREVCSEQAETGPCRAMISRWYFDVTEGKCAPFFYGGCGRNRNNFDTEEYCMAVCGSAI | 16.00 | | | |
| TW6148 | EVVREVCSEQAETGPCRAMISRWYFDVTEGKCAPFFYGGCGARNNFDTEEYCMAVCGSAI | 40.00 | 48.00 | | |
| TW124 | EVCSEQAETGPCRAMISRWYFDVTEGKCAPFFYGGCGGNSNNFDTEEYCMAVCGSAI | 64.00 | | | |
| TW6149 | EVVREVCSEQAETGPCRAAHSRWYFDVTEGKCAPFFYGGCGGNANNFDTEEYCMAVCGSAI | 54.00 | | | |
| TW6173 | EVVREVCSEQAETGPCRALHSRWYFDVTEGKCAPFFYGGCGGNRNNFDTEEYCMAVCGSAI | 1.00 | 7.24 | 1432.0 | 60.0 |
| TW6174 | EVVREVCSEQAETGPCRALLSRWYFDVTEGKCAPFFYGGCGGNRNNFDTEEYCMAVCGSAI | 0.90 | 6.89 | 2796.0 | 6.0 |
| BG002 | EVVREVCSEQAETGPCRALIPRWYFDVTEGKCAPFFYGGCGGNRNNFDTEEYCMAVCGSAI | 0.98 | 19.00 | 403.0 | |
| DD129 | EVVREVCSEQAETGPCRALFSRWYFDVTEGKCAPFFYGGCGGNRNNFDTEEYCMAVCGSAI | 3.60 | | 1864.0 | |
| DD185 | EVVREVCSEQAETGPCRAAIFRWYFDVTEGKCAPFFYGGCGGNRNNFDTEEYCMAVCGSAI | 0.39 | 8.71 | 150.0 | 196.0 |
| TW6165 | EVVREVCSEQAETGPCRAAIWRWYFDVTEGKCAPFFYGGCGGNRNNFDTEEYCMAVCGSAI | 0.65 | 16.40 | 206.0 | |
| TW6166 | EVVREVCSEQAETGPCRAAIYRWYFDVTEGKCAPFFYGGCGGNRNNFDTEEYCMAVCGSAI | 0.4 | 10.10 | 73.0 | 111.0 |
| BG028 | EVVREVCSEQAETGPCRALIYRWYFDVTEGKCAPFFYGGCGGNRNNFDTEEYCMAVCGSAI | 1.10 | 12.10 | 93.8 | |
| TW6169 | EVVREVCSEQAETGPCRALIIRWYFDVTEGKCAPFFYGGCGGNRNNFDTEEYCMAVCGSAI | 1.20 | | 619.0 | 74.0 |
| DD113 | EVVREVCSEQAETGPCRALIPRWYFDVTEGKCAPFFYGGCGGNRNNFDTEEYCMAVCGSAI | 0.85 | 12.80 | 293.0 | 56.0 |
| TW6175 | EVVREVCSEQAETGPCRALIPRWYFDVTEGKCAPFFYGGCGGNRNNFDTEEYCMAVCGSAI | 0.50 | 7.46 | 35.0 | |
| TW6201 | EVVREVCSEQAETGPCRAGIYRWYFDVTEGKCAPFFYGGCGGNRNNFDTEEYCMAVCGSAI | 34.60 | | 419.0 | |
| TW6202 | EVVREVCSEQAETGPCRAGIWRWYFDVTEGKCAPFFYGGCGGNRNNFDTEEYCMAVCGSAI | 128.50 | | 1237.0 | |
| TW6203 | EVVREVCSEQAETGPCRAGIPRWYFDVTEGKCAPFFYGGCGGNRNNFDTEEYCMAVCGSAI | 31.20 | | 5045.0 | |
| TW6204 | EVVREVCSEQAETGPCRAAISAWYFDVTEGKCAPFFYGGCGGNRNNFDTEEYCMAVCGSAI | | | 147.0 | 87.0 |
| TW6205 | EVVREVCSEQAETGPCRALISAWYFDVTEGKCAPFFYGGCGGNRNNFDTEEYCMAVCGSAI | | | 195.0 | 29.0 |

FIG. 46D

| | | | | | |
|---|---|---|---|---|---|
| DD114 | EVVREVCSEQAETGPCRAAAISRWYFDVTEGKCAPFFYGGCRGNRNNFDTEEYCMAVCGSAI | 0.70 | 7.77 | 224.0 | |
| TW6190 | EVVREVCSEQAETGPCRAAAISRWYFDVTEGKCAPFFYGGCYGNRNNFDTEEYCMAVCGSAI | 0.83 | 52.20 | 589.0 | 1396.0 |
| TW6183 | EVVREVCSEQAETGPCRAMHFRWYFDVTEGKCAPFFYGGCGGNRNNFDTEEYCMAVCGSAI | 1.20 | 11.68 | 12440.0 | 159.0 |
| TW6184 | EVVREVCSEQAETGPCRAMHYRWYFDVTEGKCAPFFYGGCGGNRNNFDTEEYCMAVCGSAI | 0.91 | 11.96 | 14000.0 | 214.0 |
| TW6185 | EVVREVCSEQAETGPCRAMHWRWYFDVTEGKCAPFFYGGCGGNRNNFDTEEYCMAVCGSAI | 1.30 | 18.60 | 388.0 | 473.0 |
| BG003 | EVVREVCSEQAETGPCRAMLHRWYFDVTEGKCAPFFYGGCGGNRNNFDTEEYCMAVCGSAI | 36.00 | | 467.0 | |
| TW6186 | EVVREVCSEQAETGPCRAMHSRWYFDVTEGKCAPFFYGGCYGNRNNFDTEEYCMAVCGSAI | 0.48 | 8.86 | 186.0 | 11.0 |
| TW6187 | EVVREVCSEQAETGPCRAMIFRWYFDVTEGKCAPFFYGGCYGNRNNFDTEEYCMAVCGSAI | 3.80 | 15.40 | 92.0 | 15.0 |
| TW6188 | EVVREVCSEQAETGPCRAMIYRWYFDVTEGKCAPFFYGGCYGNRNNFDTEEYCMAVCGSAI | 4.00 | | 419.0 | 24.0 |
| TW6189 | EVVREVCSEQAETGPCRAMMWRWYFDVTEGKCAPFFYGGCGGNRNNFDTEEYCMAVCGSAI | 4.00 | | | 34.0 |
| TW6170 | EVVREVCSEQAEPGPCRALILRWYFDVTEGKCAPFFYGGCGGNRNNFDTEEYCMAVCGSAI | 2.50 | | | 452.0 |
| TW6171 | EVVREVCSEQAETGPCRGYITRWYFDVTEGKCAPFFYGGCGGNRNNFDTEEYCMAVCGSAI | | | 213.0 | 299.0 |
| DD115 | EVVREVCSEQAETGPCRALHNRWYFDVTEGKCAPFFYGGCGGNRNNFDTEEYCMAVCGSAI | 0.99 | 18.00 | 550.0 | |
| DD170 | EVVREVCSEQAETGPCRAAHFRWYFDVTEGKCAPFFYGGCGGNRNNFDTEEYCMAVCGSAI | 3.50 | 118.00 | 56.0 | |
| TW6176 | EVVREVCSEQAETGPCRALHFRWYFDVTEGKCAPFFYGGCGGNRNNFDTEEYCMAVCGSAI | 7.20 | 32.70 | 245.0 | 156.0 |
| TW6177 | EVVREVCSEQAETGPCRAAFSAWYFDVTEGKCAPFFYGGCGGNRNNFDTEEYCMAVCGSAI | 0.30 | 12.10 | 80.0 | |
| BG006 | EVVREVCSEQAETGPCRAALFRWYFDVTEGKCAPFFYGGCGGNRNNFDTEEYCMAVCGSAI | 5.50 | | | 9.5 |
| DD130 | EVVREVCSEQAETGPCRALFTRWYFDVTEGKCAPFFYGGCGGNRNNFDTEEYCMAVCGSAI | 7.90 | 2.00 | 1385.0 | 3.3 |
| DD131 | EVVREVCSEQAETGPCRAFFKRWYFDVTEGKCAPFFYGGCGGNRNNFDTEEYCMAVCGSAI | 112.00 | | | 16.8 |
| DD132 | EVVREVCSEQAETGPCRAAFSAWYFDVTEGKCAPFFYGGCGGNRNNFDTEEYCMAVCGSAI | 8.30 | | | 11.0 |
| DD120 | EVVREVCSEQAETGPCRALLSAWYFDVTEGKCAPFFYGGCGGNRNNFDTEEYCMAVCGSAI | 19.00 | | | 21.0 |
| DD121 | EVVREVCSEQAETGPCRALIWHWYFDVTEGKCAPFFYGGCGGNRNNFDTEEYCMAVCGSAI | 9.20 | 18.70 | 18.0 | |
| BG014 | EVVREVCSEQAETGPCRALIFAWYFDVTEGKCAPFFYGGCGGNRNNFDTEEYCMAVCGSAI | 15.00 | | | 46.0 |
| DD122 | EVVREVCSEQAETGPCRALIYHWYFDVTEGKCAPFFYGGCGGNRNNFDTEEYCMAVCGSAI | 6.00 | 12.20 | 19.4 | |
| BG015 | EVVREVCSEQAETGPCRAIIHKWYFDVTEGKCAPFFYGGCGGNRNNFDTEEYCMAVCGSAI | 1.70 | | 106.0 | 597.0 |
| BG020 | | | | | |

FIG. 46E

| | Sequence | | | |
|---|---|---|---|---|
| BG022 | EVVREVCSEQAETGPCRAAIYHWYFDVTEGKCAPFFYGGCGGNRNNFDTEEHCMAVCGSAI | 0.64 | | 14.5 | |
| BG023 | EVVREVCSEQAETGPCRALIQHWYFDVTEGKCAPFFYGGCGGNRNNFDTEEYCMAVCGSAI | 23.00 | 7.26 | 262.0 | |
| BG024 | EVVREVCSEQAETGPCRALIYKWYFDVTEGKCAPFFYGGCGGNRNNFDTEEYCMAVCGSAI | 4.10 | 7.47 | 38.7 | |
| BG027 | EVVREVCSEQAETGPCRAAIQHWYFDVTEGKCAPFFYGGCGGNRNNFDTEEYCMAVCGSAI | 5.80 | | 144.0 | |
| DD116 | EVVREVCSEQAETGPCRAAIFRWYFDVTEGKCAPFFYGGCRGNRNNFDTEEYCMAVCGSAI | 0.14 | | 583.0 | 84.0 |
| TW6191 | EVVREVCSEQAETGPCRAAIFRWYFDVTEGKCAPFFYGGCYGNRNNFDTEEYCMAVCGSAI | 0.26 | | 664.0 | 20.0 |
| DD117 | EVVREVCSEQAETGPCRALIPRWYFDVTEGKCAPFFYGGCRGNRNNFDTEEYCMAVCGSAI | 0.11 | | 1034.0 | 99.0 |
| BG029 | EVVREVCSEQAETGPCRALIYHWYFDVTEGKCAPFFYGGCGGNRNNFDTEEYCMAVCGSAI | 3.20 | | 7.9 | |
| BG030 | EVVREVCSEQAEVGPCRALIYHWYFDVTEGKCAPFFYGGCGGNRNNFDTEEYCMAVCGSAI | 4.60 | | 26.1 | |
| BG033 | EVVREVCSEQAESGPCRAVGPCRAAIYHWYFDVTEGKCAPFFYGGCGGNRNNFDTEEHCMAVCGSAI | 0.75 | | 5.6 | |
| BG034 | EVVREVCSEQAESGPCRAAIYHWYFDVTEGKCAPFFYGGCGGNRNNFDTEEYCMAVCGSAI | 0.47 | | 18.5 | |
| BG040 | EVVREVCSEQAEIGPCRALIYHWYFDVTEGKCAPFFYGGCGGNRNNFDTEEYCMAVCGSAI | 3.40 | | 8.6 | |
| BG016 | EVVREVCSEQAETGPCRGAIQHWYFDVTEGKCAPFFYGGCGGNRNNFDTEEYCMAVCGSAI | 160.00 | | 178.0 | |
| BG017 | EVVREVCSEQAETGPCRGAIRHWYFDVTEGKCAPFFYGGCGGNRNNFDTEEYCMAVCGSAI | 180.00 | | 200.0 | |
| BG021 | EVVREVCSEQAETGPCRGSIRHWYFDVTEGKCAPFFYGGCGGNRNNFDTEEYCMAVCGSAI | 340.00 | | 224.0 | |
| BG025 | EVVREVCSEQAETGPCRGLIYHWYFDVTEGKCAPFFYGGCGGNRNNFDTEEYCMAVCGSAI | 65.00 | | 16.2 | |
| BG026 | EVVREVCSEQAETGPCRGAIYHWYFDVTEGKCAPFFYGGCGGNRNNFDTEEYCMAVCGSAI | 50.00 | | 34.9 | |
| DD118 | EVVREVCSEQAETGPCRALIHNRWYFDVTEGKCAPFFYGGCRGNRNNFDTEEYCMAVCGSAI | 0.53 | | | |
| DD134 | EVVREVCSEQAETGPCRALFKRWYFDVTEGKCAPFFYGGCCYGNRNNFDTEEYCMAVCGSAI | 1.10 | 1.05 | 15640.0 | 0.6 |
| DD135 | EVVREVCSEQAETGPCRALFKRWYFDVTEGKCAPFFYGGCCLGNRNNFDTEEYCMAVCGSAI | 1.30 | | 7473.0 | 0.9 |
| DD136 | EVVREVCSEQAETGPCRALFKRWYFDVTEGKCAPFFYGGCMGNRNNFDTEEYCMAVCGSAI | 1.10 | | | 1.8 |

| VOLUMES | |
|---|---|
| NS | 344.25 |
| KPI | 245.75 |

| | KPI | NS |
|---|---|---|
| | 298 | 366 |
| | 266 | 342 |
| | 354 | 294 |
| | 258 | 385 |
| | 168 | 288 |
| | 266 | 469 |
| | 172 | 338 |
| | 184 | 272 |
| MEAN | 245.75 | 344.25 |
| STDEV | 66.2414415 | 63.97488346 |
| TTEST | | 0.009094999 |

HEMOGLOBIN

| NS | 23.61 |
|----|-------|
| KPI | 13.59 |

| | KPI | NS |
|---|---|---|
| | 16.58 | 24.95 |
| | 15.19 | 24.87 |
| | 20.21 | 20.46 |
| | 8.99 | 27.59 |
| | 14.63 | 18.23 |
| | 15.31 | 31.59 |
| | 7.7 | 23.26 |
| | 10.14 | 17.96 |
| MEAN | 13.59375 | 23.61375 |
| STDEV | 4.261438 | 4.68761 |
| TTEST | | 0.000536 |

FIG. 49

PaO2

| | Baseline PaO2 | | End CPB | | Obs 60 min | | Obs 180 min | |
|---|---|---|---|---|---|---|---|---|
| | KPI | NS | KPI | NS | KPI | NS | KPI | NS |
| | 652.2 | 670.9 | 495.7 | 60.5 | 483.7 | 441.3 | | 391.3 |
| | 654 | 559.2 | 444.6 | 132.2 | 330.1 | 448.7 | 264.1 | 484.6 |
| | 596.2 | 622.9 | 170.2 | 93.8 | 415.4 | 85.1 | 416.5 | 81.3 |
| | 606.2 | 689.2 | 264.2 | 333.9 | 430.2 | 529.6 | 361.9 | 333.2 |
| | 633.1 | 665.1 | 567.2 | 341.7 | 613 | 568.3 | 90.8 | 546.6 |
| | 646.6 | 527 | 507.4 | 226.9 | 564.3 | 438.1 | 518.2 | 485.3 |
| | 563.2 | 461.7 | 547.1 | 89.1 | 501 | 42.6 | 494.2 | 45.6 |
| | 659.9 | 508 | 416.6 | 59.7 | 504.5 | 405.8 | 452 | 383.7 |
| MEAN | 626.425 | 588 | 426.625 | 167.225 | 480.275 | 369.938 | 371.1 | 344 |
| STDEV | 34.4692 | 85.5055 | 140.474 | 117.993 | 88.6187 | 196.523 | 150.277 | 186.22 |
| TTEST | 3 | 6 | 1 | 1 | 9 | 5 | 4 | 7 |
| | $p=$ 0.268 | | $p=$ 0.0014 | | $p=$ 0.17915 | | $p=$ 0.76 | |
| | N.S. | | | | N.S. | | N.S. | |

FIG. 50

*Summary of Data*

| | Total volume loss | Total Hgb Loss | Chest tube | Sacrifice | 0-30min | 30-60min | 60-120min | 120-180min |
|---|---|---|---|---|---|---|---|---|
| | | | | | | | Serial Chest tube Hbg | |
| KPI-1 | 298 | 16.58 | 185 | 113 | 3.7 | 4.3 | 8.6 | 6.2 |
| KPI-2 | 266 | 15.19 | 198 | 68 | 4.3 | 6.4 | 6.7 | 5.7 |
| KPI-3 | 354 | 20.21 | 142 | 212 | 4.1 | 4.4 | 7 | 7.1 |
| KPI-4 | 258 | 8.99 | 190 | 68 | 2.8 | 4 | 4.4 | 1.9 |
| KPI-5 | 168 | 14.63 | 96 | 72 | 6.3 | 6.5 | 7 | 6.7 |
| KPI-6 | 266 | 15.31 | 188 | 78 | 4.1 | 6.1 | 5.6 | 6.3 |
| KPI-7 | 172 | 7.7 | 134 | 38 | 3.1 | 4.6 | 5.4 | 4.4 |
| KPI-8 | 184 | 10.14 | 158 | 26 | 6.9 | 5.8 | 5.4 | 4.2 |
| MEAN | 245.75 | 13.59 | | | 4.41 | 5.26 | 6.26 | 5.3 |
| STDEV | 66.24 | 4.26 | | | 1.45 | 1.04 | 1.32 | 1.72 |
| NS-1A | 366 | 24.95 | 274 | 92 | 7.7 | 8.6 | 6.1 | 5.4 |
| NS-2 | 342 | 24.87 | 236 | 106 | 7.2 | 7.4 | 7.6 | 7.1 |
| NS-3 | 294 | 20.46 | 252 | 42 | 5.4 | 7.5 | 7.5 | 6.5 |
| NS-4 | 385 | 27.59 | 303 | 82 | 8.4 | 7.2 | 7.1 | 6.3 |
| NS-5 | 288 | 18.23 | 140 | 148 | 7.5 | 7.2 | 5.2 | 5.6 |
| NS-6 | 469 | 31.59 | 261 | 208 | 4 | 7 | 7.3 | 7.4 |
| NS-7 | 338 | 23.26 | 218 | 120 | 7.5 | 7.7 | 5.8 | 4.2 |
| NS-8 | 272 | 17.96 | 206 | 66 | 7.4 | 8.2 | 6 | 5.3 |
| MEAN | 344.25 | 23.61 | | | 6.89 | 7.6 | 6.58 | 6.1 |
| STDEV | 63.97 | 4.69 | | | 1.44 | 1.04 | 0.91 | 0.85 |
| | *p = 0.009 | *p = 0.0005 | | | *p = 0.004 | *p = 0.0002 | NS | NS |

PROTEASE INHIBITOR PEPTIDES

This application is a continuation of application Ser. No. 08/829,876, filed Apr. 2, 1997, now U.S. Pat. No. 5,962,266 which is a divisional of Ser. No. 08/436,555 filed May 8, 1995.

BACKGROUND OF THE INVENTION

The plasma, or serine, proteases of the blood contact system are known to be activated by interaction with negatively charged surfaces. For example, tissue injury during surgery exposes the vascular basement membrane, causing interaction of the blood with collagen, which is negatively charged at physiological Ph. This induces a cascade of proteolytic events, leading to production of plasmin, a fibrinolytic protease, and consequent blood loss.

Perioperative blood loss of this type can be particularly severe during cardiopulmonary bypass (CPB) surgery, in which the patient's blood flow is diverted to an artificial heart-lung machine. CPB is an essential component of a number of life-saving surgical procedures. For example, in the United States, it is estimated that 300,000 patients every year undergo coronary artery bypass grafts involving the use of CPB.

Although necessary and generally safe, CPB is associated with a significant rate of morbidity, some of which may be attributed to a "whole body inflammatory response" caused by activation of plasma protease systems and blood cells through interactions with the artificial surfaces of the heart-lung machine (Butler et al., *Ann. Thorac. Surg.* 55:552 (1993); Edmunds et al., *J. Card. Surg.* 8:404 (1993)). For example, during extracorporeal circulation, exposure of blood to negatively charged surfaces of the artificial bypass circuit, e.g., plastic surfaces in the heart-lung machine, results in direct activation of plasma factor XII.

Factor XII is a single-chain 80 kDa protein that circulates in plasma as an inactive zymogen. Contact with negatively charged nonendothelial surfaces, like those of the bypass circuit, causes surface-bound factor XII to be autoactivated to the active serine protease factor XIIa. See Colman, *Agents Actions Suppl.* 42:125 (1993). Surface-activated factor XIIa then processes prekallikrein (PK) to active kallikrein, which in turn cleaves more XIIa from XII in a reciprocal activation reaction that results in a rapid amplification of the contact pathway. Factor XIIa can also activate the first component of complement C1, leading to production of the anaphylatoxin C5a through the classical complement pathway.

The CPB-induced inflammatory response includes changes in capillary permeability and interstitial fluid accumulation. Cleavage of high molecular weight kininogen (HK) by activated kallikrein generates the potent vasodilator bradykinin, which is thought to be responsible for increasing vascular permeability, resulting in edema, especially in the lung. The lung is particularly susceptible to damage associated with CPB, with some patients exhibiting what has been called "pump lung syndrome" following bypass, a condition indistinguishable from adult respiratory distress. See Johnson et al., *J. Thorac. Cardiovasc. Surg.* 107:1193 (1994).

Post-CPB pulmonary injury includes tissue damage thought to be mediated by neutrophil sequestration and activation in the microvasculature of the lung. (Butler et al., supra; Johnson, et al., supra). Activated factor XII can itself stimulate neutrophil aggregation. Factor XIIa-generated kallikrein, and complement protein C5a generated by Factor XIIa activation of the complement cascade, both induce neutrophil chemotaxis, aggregation and degranulation. See Edmunds et al., supra (1993). Activated neutrophils may damage tissue through release of oxygen-derived free-radicals, proteolytic enzymes such as elastase, and metabolites of arachidonic acid. Release of neutrophil products in the lung can cause changes in vascular tone, endothelial injury and loss of vascular integrity.

Intrinsic inhibition of the contact system occurs through inhibition of activated XIIa by C1-inhibitor (C1-INH). See Colman, supra. During CPB, this natural inhibitory mechanism is overwhelmed by massive activation of plasma proteases and consumption of inhibitors. A potential therapeutic strategy for reducing post-bypass pulmonary injury mediated by neutrophil activation would, therefore, be to block the formation and activity of the neutrophil agonists kallikrein, factor XIIa, and C5a by inhibition of proteolytic activation of the contact system.

Protease inhibitor therapy which partially attenuates the contact system is currently employed clinically in CPB. Aprotinin, also known as basic pancreatic protease inhibitor (BPPI), is a small, basic, 58 amino acid polypeptide isolated from bovine lung. It is a broad spectrum serine protease inhibitor of the Kunitz type, and was first used during bypass in an attempt to reduce the inflammatory response to CPB. See Butler et al., supra. Aprotinin treatment results in a significant reduction in blood loss following bypass, but does not appear to significantly reduce neutrophil activation. Additionally, since aprotinin is of bovine origin, there is concern that repeated administration to patients could lead to the development of an immune response to aprotinin in the patients, precluding its further use.

The proteases inhibited by aprotinin during CPB appear to include plasma kallikrein and plasmin. (See, e.g., Scott, et al., *Blood* 69:1431 (1987)). Aprotinin is an inhibitor of plasmin ($K_i$ of 0.23 nM), and the observed reduction in blood loss may be due to inhibition of fibrinolysis through the blocking of plasmin action. Although aprotinin inhibits plasma kallikrein, ($K_i$ of 20 nM), it does not inhibit activated factor XII, and consequently only partially blocks the contact system during CPB.

Another attractive protease target for use of protease inhibitors, such as those of the present invention, is factor XIIa, situated at the very first step of contact activation. By inhibiting the proteolytic activity of factor XIIa, kallikrein production would be prevented, blocking amplification of the contact system, neutrophil activation and bradykinin release. Inhibition of XIIa would also prevent complement activation and production of C5a. More complete inhibition of the contact system during CPB could, therefore, be achieved through the use of a better XIIa inhibitor.

Protein inhibitors of factor XIIa are known. For example, active site mutants of $\alpha_1$-antitrypsin that inhibit factor XIIa have been shown to inhibit contact activation in human plasma. See Patston et al., *J. Biol. Chem.* 265:10786 (1990). The large size and complexity (greater than 400 amino acid residues) of these proteins present a significant challenge for recombinant protein production, since large doses will almost certainly be required during CPB. For example, although it is a potent inhibitor of both kallikrein and plasmin, nearly 1 gram of aprotinin must be infused into a patient to inhibit the massive activation of the kallikrein-kinin and fibrinolytic systems during CPB.

The use of smaller, more potent XIIa inhibitors such as the corn and pumpkin trypsin inhibitors (Wen, et al., *Protein Exp. & Purif.* 4:215 (1993); Pedersen, et al., *J. Mol. Biol.* 236:385 (1994)) could be more cost-effective than the large α₁-antitrypsins, but the infusion of high doses of these non-mammalian inhibitors could result in immunologic reactions in patients undergoing repeat bypass operations. The ideal protein XIIa inhibitor is, therefore, preferably, small, potent, and of human sequence origin.

One candidate for an inhibitor of human origin is found in circulating isoforms of the human amyloid β-protein precursor (APPI), also known as protease nexin-2. APPI contains a Kunitz serine protease inhibitor domain known as KPI (Kunitz Protease Inhibitor). See Ponte et al., *Nature*, 331:525 (1988); Tanzi et al., *Nature* 331:528 (1988); Johnstone et al., *Biochem. Biophys. Res. Commun.* 163:1248 (1989); Oltersdorf et al., *Nature* 341:144 (1989). Human KPI shares about 45% amino acid sequence identity with aprotinin. The isolated KPI domain has been prepared by recombinant expression in a variety of systems, and has been shown to be an active serine protease inhibitor. See, for example, Sinha, et al., *J. Biol. Chem.* 265:8983 (1990). The measured in vitro $K_i$ of KPI against plasma kallikrein is 45 nM, compared to 20 nM for aprotinin.

Aprotinin, KPI, and other Kunitz-type serine protease inhibitors have been engineered by site-directed mutagenesis to improve inhibitory activity or specificity. Thus, substitution of $Lys^{15}$ of aprotinin with arginine resulted in an inhibitor with a $K_i$ of 0.32 nM toward plasma kallikrein, a 100-fold improvement over natural aprotinin. See PCT application No. 89/10374. See also Norris et al., *Biol. Chem. Hoppe Seyler* 371:3742 (1990). Alternatively, substitution of position 15 of aprotinin with valine or substitution of position 13 of KPI with valine resulted in elastase inhibitors with $K_i$s in the 100 pM range, although neither native aprotinin nor native KPI significantly inhibits elastase. See Wenzel et al., in: *Chemistry of Peptides and Proteins, Vol. 3*, (Walter de Gruyter, Berlin, N.Y., 1986); Sinha et al., supra. Methods for substituting residues 13, 15, 37, and 50 of KPI are shown in general terms in European Patent Application No. 0 393 431, but no specific sequences are disclosed, and no protease inhibition data are given.

Phage display methods have been recently used for preparing and screening derivatives of Kunitz-type protease inhibitors. See PCT Application No. 92/15605, which describes specific sequences for 34 derivatives of aprotinin, some of which were reportedly active as elastase and cathepsin inhibitors. The amino acid substitutions in the derivatives were distributed throughout almost all positions of the aprotinin molecule.

Phage display methods have also been used to generate KPI variants that inhibit factor VIIa and kallikrein. See Dennis et al., *J. Biol. Chem.* 269:22129 and 269:22137 (1994). The residues that could be varied in the phage display selection process were limited to positions 9–11, 13–17, 32, 36 and 37, and several of those residues were also held constant for each selection experiment. One of those variants was said to have a $K_i$ of 1.2 nM for kallikrein, and had substitutions at positions 9 (Thr→Pro), 13 (Arg→Lys), 15 (Met→Leu), and 37 (Gly→Tyr). None of the inhibitors was tested for the ability to inhibit factor XIIa.

It is apparent, therefore, that new protease inhibitors that can bind to and inhibit the activity of serine proteases are greatly to be desired. In particular it is highly desirable to prepare peptides, based on human peptide sequences, that can inhibit selected serine proteases such as kallikrein; chymotrypsins A and B; trypsin; elastase; subtilisin; coagulants and procoagulants, particularly those in active form, including coagulation factors such as factors VIIa, IXa, Xa, XIa, and XIIa; plasmin; thrombin; proteinase-3; enterokinase; acrosin; cathepsin; urokinase; and tissue plasminogen activator. It is also highly desirable to prepare novel protease inhibitors that can ameliorate one or more of the undesirable clinical manifestations associated with enhanced serine protease activity, for example by reducing pulmonary damage or blood loss during CPB.

SUMMARY OF THE INVENTION

The present invention relates to peptides that can bind to and preferably exhibit inhibition of the activity of serine proteases. Those peptides can also provide a means of ameliorating, treating or preventing clinical conditions associated with increased activity of serine proteases. Particularly, the novel peptides of the present invention preferably exhibit a more potent and specific (i.e., greater) inhibitory effect toward serine proteases of interest in comparison to known serine protease inhibitors. Examples of such proteases include: kallikrein; chymotrypsins A and B; trypsin; elastase; subtilisin; coagulants and procoagulants, particularly those in active form, including coagulation factors such as factors VIIa, IXa, Xa, XIa, and XIIa; plasmin; thrombin; proteinase-3; enterokinase; acrosin; cathepsin; urokinase; and tissue plasminogen activator.

In achieving the inhibition of serine protease activity, the invention provides protease inhibitors that can ameliorate one or more of the undesirable clinical manifestations associated with enhanced serine protease activity, for example, by reducing pulmonary damage or blood loss during CPB.

The present invention relates to protease inhibitors comprising the following amino acid sequences (SEQ ID NO:1):

$X^1$-Val-Cys-Ser-Glu-Gln-Ala-Glu-$X^2$-Gly-$X^3$-CyS-Arg-Ala-$X^4$-$X^5$-$X^6$-$X^7$-Trp-Tyr-Phe-Asp-Val-Thr-Glu-Gly-Lys-Cys-Ala-Pro-Phe-$X^8$-Tyr-Gly-Gly-Cys-$X^9$-$X^{10}$-$X^{11}$-$X^{12}$-Asn-Asn-Phe-Asp-Thr-Glu-Glu-Tyr-Cys-Met-Ala-Val-Cys-Gly-Ser-Ala-Ile, wherein: $X^1$ is selected from (SEQ ID NO:2) Glu-Val-Val-Arg-Glu-, Asp, or Glu; $X^2$ is selected from Thr, Val, Ile and Ser; $X^3$ is selected from Pro and Ala; $X^4$ is selected from Arg, Ala, Leu, Gly, or Met; $X^5$ is selected from Ile, His, Leu, Lys, Ala, or Phe; $X^6$ is selected from Ser, Ile, Pro, Phe, Tyr, Trp, Asn, Leu, His, Lys, or Glu; $X^7$ is selected from Arg, His, or Ala; $X^8$ is selected from Phe, Val, Leu, or Gly; $X^9$ is selected from Gly, Ala, Lys, Pro, Arg, Leu, Met, or Tyr; $X^{10}$ is selected from Ala, Arg, or Gly; $X^{11}$ is selected from Lys, Ala, or Asn; and $X^{12}$ is selected from Ser, Ala, or Arg.

The invention relates more specifically to protease inhibitors comprising the following amino acid sequences (SEQ ID NO:1):

$X^1$-Val-Cys-Ser-Glu-Gln-Ala-Glu-$X^2$-Gly-$X^3$-Cys-Arg-Ala-$X^4$-$X^5$-$X^6$-$X^7$-Trp-Tyr-Phe-Asp-Val-Thr-Glu-Gly-Lys-Cys-Ala-Pro-Phe-$X^8$-Tyr-Gly-Gly-Cys-$X^9$-$X^{10}$-$X^{11}$-$X^{12}$-Asn-Asn-Phe-Asp-Thr-Glu-Glu-Tyr-Cys-Met-Ala-Val-Cys-Gly-Ser-Ala-Ile, wherein $X^1$ is selected from (SEQ ID NO:2) Glu-Val-Val-Arg-Glu-, Asp, or Glu; $X^2$ is selected from Thr, Val, Ile and Ser; $X^3$ is selected from Pro and Ala; $X^4$ is selected from Arg, Ala, Leu, Gly, or Met; $X^5$ is selected from Ile, His, Leu, Lys, Ala, or Phe; $X^6$ is selected from Ser, Ile, Pro, Phe, Tyr, Trp, Asn, Leu, His, Lys, or Glu; $X^7$ is selected from Arg, His, or Ala; $X^8$ is selected from Phe, Val, Leu, or Gly; $X^9$ is selected from Gly, Ala, Lys, Pro, Arg, Leu, Met, or Tyr; $X^{10}$ is selected from Ala, Arg, or Gly; $X^{11}$ is selected from Lys, Ala, or Asn; $X^{12}$ is selected from Ser, Ala, or Arg; provided that when $X^4$ is Arg, $X^6$ is Ile; when $X^9$ is Arg, $X^4$ is Ala or Leu; when $X^9$ is Tyr, $X^4$ is Ala or $X^5$ is His; and either $X^5$ is not Ile; or $X^6$ is not Ser; or $X^9$ is not Leu, Phe, Met, Tyr, or Asn; or $X^{10}$ is not Gly; or $X^{11}$ is not Asn; or $X^{12}$ is not Arg.

Another aspect of this invention provides protease inhibitors wherein at least two amino acid residues selected from the group consisting of $X^4$, $X^5$, $X^6$, and $X^7$ defined above differ from the residues found in the naturally occurring sequence of KPI. Another aspect of this invention provides protease inhibitors wherein $X^1$ is Asp or Glu, $X^2$ is Thr, $X^3$ is Pro, and $X^{12}$ is Ser. Yet another aspect of this invention provides protease inhibitors wherein $X^1$ is Glu, $X^2$ is Thr, $X^3$ is Pro, $X^4$ is Met, $X^5$ is Ile, $X^6$ is Ser, $X^7$ is Arg, $x^8$ is Phe, $X^9$ is Gly, $X^{10}$ is Gly, and $X^{11}$ is Asn. Another aspect of this invention provides protease inhibitors wherein $X^1$ is Asp, $X^2$ is Thr, $X^3$ is Pro, $X^4$ is Arg, $X^5$ is Ile, $X^6$ is Ile, $X^7$ is Arg, $X^8$ is Val, $X^9$ is Arg, $X^{10}$ is Ala, and $X^{11}$ is Lys. Another aspect of this invention provides protease inhibitors wherein $X^1$ is (SEQ ID NO:2) Glu-Val-Val-Arg-Glu-, $X^2$ is Thr, $X^3$ is Pro, $X^4$ is Met, $X^5$ is Ile, $X^6$ is Ser, $X^7$ is Arg, $x^8$ is Phe, $X^9$ is Gly, $X^{10}$ is Gly, $X^{11}$ is Asn, and $X^{12}$ is Ala. Another aspect of this invention provides protease inhibitors wherein $X^1$ is (SEQ ID NO:2) Glu-Val-Val-Arg-Glu-, $X^2$ is Thr, $X^3$ is Pro, $X^4$ is Met, $X^5$ is Ile, $X^6$ is Ser, $X^7$ is Arg, $x^8$ is Phe, $X^9$ is Gly, $X^{10}$ is Gly, $X^{11}$ is Ala, and $X^{12}$ is Arg. Another aspect of this invention provides protease inhibitors wherein $X^1$ is Glu, $X^2$ is Thr, $X^3$ is Pro, $X^4$ is Met, $X^5$ is Ile, $X^6$ is Ser, $X^7$ is Arg, $x^8$ is Phe, $X^9$ is Gly, $X^{10}$ is Ala, $X^{11}$ is Asn, and $X^{12}$ is Arg. Another aspect of this invention provides protease inhibitors wherein $X^1$ is (SEQ ID NO:2) Glu-Val-Val-Arg-Glu-, $X^2$ is Thr, $X^3$ is Pro, $X^4$ is Met, $X^5$ is Ile, $X^6$ is Ser, $X^7$ is Arg, $x^8$ is Phe, $X^9$ is Gly, $X^{10}$ is Arg, $X^{11}$ is Asn, and $X^{12}$ is Arg. Another aspect of this invention provides protease inhibitors wherein $X^1$ is (SEQ ID NO:2) Glu-Val-Val-Arg-Glu-, $X^2$ is Thr, $X^3$ is Pro, $X^4$ is Met, $X^5$ is Ile, $X^6$ is Ser, $X^7$ is Arg, $x^8$ is Val, Leu, or Gly, $X^9$ is Gly, $X^{10}$ is Gly, $X^{11}$ is Asn, and $X^{12}$ is Arg. Another aspect of this invention provides protease inhibitors wherein $X^1$ is (SEQ ID NO:2) Glu-Val-Val-Arg-Glu-, $X^2$ is Thr, $X^3$ is Pro, $X^4$ is Met, $X^5$ is Ile, $X^6$ is Ser, $X^7$ is Ala, $x^8$ is Phe, $X^9$ is Gly, $X^{10}$ is Gly, $X^{11}$ is Asn, and $X^{12}$ is Arg. Another aspect of this invention provides protease inhibitors wherein $X^1$ is (SEQ ID NO:2) Glu-Val-Val-Arg-Glu-, $X^2$ is Thr, Val, or Ser, $X^3$ is Pro, $X^4$ is Ala or Leu, $X^5$ is Ile, $X^6$ is Tyr, $X^7$ His, $X^8$ is Phe, $X^9$ is Gly, $X^{10}$ is Gly, $X^{11}$ is Ala, and $X^{12}$ is Arg.

Yet another aspect of this invention provides protease inhibitors wherein $X^2$ is Thr, and $X^4$ is Ala. Another aspect of this invention provides protease inhibitors wherein $X^2$ is Thr, and $X^4$ is Leu. Another aspect of this invention provides protease inhibitors wherein $X^2$ is Val, and $X^4$ is Ala. Another aspect of this invention provides protease inhibitors wherein $X^2$ is Ser, and $X^4$ is Ala. Another aspect of this invention provides protease inhibitors wherein $X^2$ is Val, and $X^4$ is Leu. Another aspect of this invention provides protease inhibitors wherein $X^2$ is Ser, and $X^4$ is Leu.

Yet another aspect of this invention provides protease inhibitors wherein $X^1$ is (SEQ ID NO:2) Glu-Val-Val-Arg-Glu-, $X^2$ is Thr, $X^3$ is Pro, $X^4$ is Leu, $X^5$ is Phe, $X^6$ is Lys, $X^7$ is Arg, $X^8$ is Phe, $X^9$ is Gly, $X^{10}$ is Gly, $X^{11}$ is Ala, and $X^{12}$ is Arg. Another aspect of this invention provides protease inhibitors wherein $X^1$ is (SEQ ID NO:2) Glu-Val-Val-Arg-Glu-, $X^2$ is Thr, $X^3$ is Pro, $X^4$ is Leu, $X^5$ is Phe, $X^6$ is Lys, $X^7$ is Arg, $X^8$ is Phe, $X^9$ is Tyr, $X^{10}$ is Gly, $X^{11}$ is Ala, and $X^{12}$ is Arg. Another aspect of this invention provides protease inhibitors wherein $X^1$ is (SEQ ID NO:2) Glu-Val-Val-Arg-Glu-, $X^2$ is Thr, $X^3$ is Pro, $X^4$ is Leu, $X^5$ is Phe, $X^6$ is Lys, $X^7$ is Arg, $X^8$ is Phe, $X^9$ is Leu, $X^{10}$ is Gly, $X^{11}$ is Ala, and $X^{12}$ is Arg.

A further aspect of this invention provides an isolated DNA molecule comprising a DNA sequence encoding a protease inhibitor of the invention. Another aspect of this invention provides an isolated DNA molecule comprising a DNA sequence encoding the protease inhibitor that further comprises an isolated DNA molecule operably linked to a regulatory sequence that controls expression of the coding sequence of the protease inhibitor in a host cell. Another aspect of this invention provides an isolated DNA molecule comprising a DNA sequence encoding the protease inhibitor operably linked to a regulatory sequence that controls expression of the coding sequence of the protease inhibitor in a host cell that further comprises a DNA sequence encoding a secretory signal peptide. That secretory signal peptide may preferably comprise the signal sequence of yeast alpha-mating factor. Another aspect of this invention provides a host cell transformed with any of the DNA molecules defined above. Such a host cell may preferably comprise *E. coli* or a yeast cell. When such a host cell is a yeast cell, the yeast cell may preferably be *Saccharomyces cerevisiae*.

Another aspect of this invention provides a method for producing a protease inhibitor of the present invention, comprising the steps of culturing a host cell as defined above and isolating and purifying said protease inhibitor.

A further aspect of this invention provides a pharmaceutical composition, comprising a protease inhibitor of the present invention together with a pharmaceutically acceptable sterile vehicle.

An additional aspect of this invention provides a method of treatment of a clinical condition associated with increased activity of one or more serine proteases, comprising administering to a patient suffering from said clinical condition an effective amount of a pharmaceutical composition comprising a protease inhibitor of the present invention together with a pharmaceutically acceptable sterile vehicle. That method of treatment may preferably be used to treat the clinical condition of blood loss during surgery.

Yet another aspect of this invention provides a method for inhibiting the activity of serine proteases of interest in a mammal comprising administering a therapeutically effective dose of a pharmaceutical composition comprising a protease inhibitor of the present invention together with a pharmaceutically acceptable sterile vehicle.

Another aspect of this invention provides a method for inhibiting the activity of serine proteases of interest in a mammal comprising administering a therapeutically effective dose of a pharmaceutical composition comprising a protease inhibitor of the present invention together with a pharmaceutically acceptable sterile vehicle, wherein said serine proteases are selected from the group consisting of: kallikrein; chymotrypsins A and B; trypsin; elastase; subtilisin; coagulants and procoagulants, particularly those in active form, including coagulation factors such as factors VIIa, IXa, Xa, XIa, and XIIa; plasmin; thrombin; proteinase-3; enterokinase; acrosin; cathepsin; urokinase; and tissue plasminogen activator.

A further aspect of this invention relates to protease inhibitors comprising the following amino acid sequences (SEQ ID NO:3):

$X^1$-Val-Cys-Ser-Glu-Gln-Ala-Glu-Thr-Gly-Pro-Cys-Arg-Ala-$X^2$-$X^3$-$X^4$-Arg-Trp-Tyr-Phe-Asp-Val-Thr-Glu-Gly-Lys-Cys-Ala-Pro-Phe-Phe-Tyr-Gly-Gly-Cys-$X^5$-Gly-Asn-Arg-Asn-Asn-Phe-Asp-Thr-Glu-Glu-Tyr-Cys-Met-Ala-Val-Cys-Gly-Ser-Ala-Ile, wherein $X^1$ is selected from (SEQ ID NO:2) Glu-Val-Val-Arg-Glu-, Asp, or Glu; $X^2$ is selected from Ala, Leu, Gly, or Met; $X^3$ is selected from Ile, His, Leu, Lys, Ala, or Phe; $X^4$ is selected from Ser, Ile, Pro, Phe, Tyr, Trp, Asn, Leu, His, Lys, or Glu; $X^5$ is selected from Gly, Ala, Lys, Pro, Arg, Leu, Met, or Tyr; provided that when $X^5$ is Arg, $X^2$ is Ala or Leu; when $X^5$ is Tyr, $X^2$ is Ala or $X^3$ is His; and either $X^3$ is not Ile; or $X^4$ is not Ser; or $X^5$ is not Leu, Phe, Met, Tyr, or Asn. Another aspect of this invention provides a protease inhibitor as defined above wherein $X^1$ is Glu, $X^2$ is Met, $X^3$ is Ile, $X^4$ is Ile, and $X^5$ is Gly.

The invention also relates more specifically to protease inhibitors comprising the following amino acid sequences (SEQ ID NO:4):

Glu-Val-Val-Arg-Glu-Val-Cys-Ser-Glu-Gln-Ala-Glu-Thr-Gly-Pro-Cys-Arg-Ala-$X^1$-$X^2$-$X^3$-Arg-Trp-Tyr-Phe-Asp-Val-Thr-Glu-Gly-Lys-Cys-Ala-Pro-Phe-Phe-Tyr-Gly-Gly-Cys-$X^4$-Gly-Asn-Arg-Asn-Asn-Phe-Asp-Thr-Glu-Glu-Tyr-Cys-Met-Ala-Val-Cys-Gly-Ser-Ala-Ile, wherein $X^1$ is selected from Ala, Leu, Gly, or Met; $X^2$ is selected from Ile, His, Leu, Lys, Ala, or Phe; $X^3$ is selected from Ser, Ile, Pro, Phe, Tyr, Trp, Asn, Leu, His, Lys, or Glu; $X^4$ is selected from Gly, Arg, Leu, Met, or Tyr; provided that when $X^1$ is Ala, $X^2$ is Ile, His, or Leu; when $X^1$ is Leu, $X^2$ is Ile or His; when $X^1$ is Leu and $X^2$ is Ile, $X^3$ is not Ser; when $X^1$ is Gly, $X^2$ is Ile; when $X^4$ is Arg, $X^1$ is Ala or Leu; when $X^4$ is Tyr, $X^1$ is Ala or $X^2$ is His; and either $X^1$ is not Met, or $X^2$ is not Ile, or $X^3$ is not Ser, or $X^4$ is not Gly.

A further aspect of this invention provides a protease inhibitor as defined above wherein $X^1$ is Met, $X^3$ is Ser, and $X^4$ is Gly. Another aspect of this invention provides a protease inhibitor wherein $X^2$ is selected from His, Ala, Phe, Lys, and Leu. Another aspect of this invention provides a protease inhibitor wherein $X^2$ is His. Another aspect of this invention provides a protease inhibitor wherein $X^2$ is Ala. Another aspect of this invention provides a protease inhibitor wherein $X^2$ is Phe. Another aspect of this invention provides a protease inhibitor wherein $X^2$ is Lys. Another aspect of this invention provides a protease inhibitor wherein $X^2$ is Leu. Another aspect of this invention provides a protease inhibitor wherein $X^1$ is Met, $X^2$ is Ile, and $X^4$ is Gly.

Yet another aspect of this invention provides a protease inhibitor wherein $X^3$ is Ile. Another aspect of this invention provides a protease inhibitor wherein $X^3$ is Pro. Another aspect of this invention provides a protease inhibitor wherein $X^3$ is Phe. Another aspect of this invention provides a protease inhibitor wherein $X^3$ is Tyr. Another aspect of this invention provides a protease inhibitor wherein $X^3$ is Trp. Another aspect of this invention provides a protease inhibitor wherein $X^3$ is Asn. Another aspect of this invention provides a protease inhibitor wherein $X^3$ is Leu.

An additional aspect of this invention provides a protease inhibitor wherein $X^3$ is Lys. Another aspect of this invention provides a protease inhibitor wherein $X^3$ is His. Another aspect of this invention provides a protease inhibitor wherein $X^3$ is Glu. Another aspect of this invention provides a protease inhibitor wherein $X^1$ is Ala. Another aspect of this invention provides a protease inhibitor wherein $X^2$ is Ile. Another aspect of this invention provides a protease inhibitor wherein $X^3$ is Phe, and $X^4$ is Gly. Another aspect of this invention provides a protease inhibitor wherein $X^3$ is Tyr, and $X^4$ is Gly. Another aspect of this invention provides a protease inhibitor wherein $X^3$ is Trp, and $X^4$ is Gly.

Yet another other aspect of this invention provides a protease inhibitor wherein $X^3$ is Ser or Phe, and $X^4$ is Arg or Tyr. Another aspect of this invention provides a protease inhibitor wherein $X^2$ is His or Leu, $X^3$ is Phe, and $X^4$ is Gly. Another aspect of this invention provides a protease inhibitor wherein $X^1$ is Leu. Another aspect of this invention provides a protease inhibitor wherein $X^2$ is His, $X^3$ is Asn or Phe, and $X^4$ is Gly. Another aspect of this invention provides a protease inhibitor wherein $X^2$ is Ile, $X^3$ is Pro, and $X^4$ is Gly. Another aspect of this invention provides a protease inhibitor wherein $X^1$ is Gly, $X^2$ is Ile, $X^3$ is Tyr, and $X^4$ is Gly. Another aspect of this invention provides a protease inhibitor wherein $X^1$ is Met, $X^2$ is His, $X^3$ is Ser, and $X^4$ is Tyr.

Additionally, another aspect of this invention relates to protease inhibitors comprising the following amino acid sequences (SEQ ID NO:5):

$X^1$-Val-Cys-Ser-Glu-Gln-Ala-Glu-$X^2$-Gly-Pro-Cys-Arg-Ala-$X^3$-$X^4$-$X^5$-$X^6$-Trp-Tyr-Phe-Asp-Val-Thr-Glu-Gly-Lys-Cys-Ala-Pro-Phe-Phe-Tyr-Gly-Gly-Cys-$X^7$-Gly-Asn-Arg-Asn-Asn-Phe-Asp-Thr-Glu-Glu-Tyr-Cys-Met-Ala-Val-Cys-Gly-Ser-Ala-Ile, wherein $X^1$ is selected from (SEQ ID NO:2) Glu-Val-Val-Arg-Glu-, Asp, or Glu; $X^2$ is selected from Thr, Val, Ile and Ser; $X^3$ is selected from Arg, Ala, Leu, Gly, or Met; $X^4$ is selected from Ile, His, Leu, Lys, Ala, or Phe; $X^5$ is selected from Ser, Ile, Pro, Phe, Tyr, Trp, Asn, Leu, His, Lys, or Glu; $X^6$ is selected from Arg, His, or Ala; and $X^7$ is selected from Gly, Ala, Lys, Pro, Arg, Leu, Met, or Tyr.

Another aspect of this invention provides a protease inhibitor as defined above wherein at least two amino acid residues selected from the group consisting of $X^3$, $X^4$, $X^5$, and $X^6$ differ from the residues found in the naturally occurring sequence of KPI. Another aspect of this invention provides a protease inhibitor wherein $X^1$ is (SEQ ID NO:2) Glu-Val-Val-Arg-Glu-, $X^2$ is Thr, Val, or Ser, $X^3$ is Ala or Leu, $X^4$ is Ile, $X^5$ is Tyr, $X^6$ is His and $X^7$ is Gly. Another aspect of this invention provides a protease inhibitor wherein $X^2$ is Thr, and $X^3$ is Ala. Another aspect of this invention provides a protease inhibitor wherein $X^2$ is Thr, and $X^3$ is Leu. Another aspect of this invention provides a protease inhibitor wherein $X^2$ is Val, and $X^3$ is Ala. Another aspect of this invention provides a protease inhibitor wherein $X^2$ is Ser, and $X^3$ is Ala. Another aspect of this invention provides a protease inhibitor wherein $X^2$ is Val, and $X^3$ is Leu. Another aspect of this invention provides a protease inhibitor wherein $X^2$ is Ser, and $X^3$ is Leu. Another aspect of this invention provides a protease inhibitor wherein $X^1$ is (SEQ ID NO:2) Glu-Val-Val-Arg-Glu-, $X^2$ is Thr, $X^3$ is Leu, $X^4$ is Phe, $X^5$ is Lys, $X^6$ is Arg and $X^7$ is Gly. Another aspect of this invention provides a protease inhibitor wherein $X^1$ is (SEQ ID NO:2) Glu-Val-Val-Arg-Glu-, $X^2$ is Thr, $X^3$ is Leu, $X^4$ is Phe, $X^5$ is Lys, $X^6$ is Arg and $X^7$ is Tyr. Another aspect of this invention provides a protease inhibitor wherein $X^1$ is (SEQ ID NO:2) Glu-Val-Val-Arg-Glu-, $X^2$ is Thr, $X^3$ is Leu, $X^4$ is Phe, $X^5$ is Lys, $X^6$ is Arg and $X^7$ is Leu.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 shows the sequence (SEQ ID NOS:74 AND 75) of the synthetic gene for KPI (1→57) fused to the bacterial phoA secretory signal sequence.

FIG. 4 (SEQ ID NOS 76 AND 77) shows the 192 bp XbaI-HindIII synthetic gene fragment encoding KPI (1→57) and four amino acids from yeast alpha-mating factor.

FIG. 5 (SEQ ID NOS 78 AND 79) shows the synthetic 201 bp XbaI-HindIII fragment encoding KPI (-4→57) in PKPI-61.

FIG. 7 (SEQ ID NOS 80 AND 81) shows plasmid PTW113, encoding the 445 bp synthetic gene for yeast alpha-factor-KPI(-4→57) fusion.

FIG. 8 shows the amino acid sequence (SEQ ID NO:79) for KPI (-4→57).

FIG. 10 (SEQ ID NOS 82 AND 83) shows plasmid, PTW6165, encoding the 445 bp synthetic gene for alpha-factor-KPI(-4→57; M15A, S17W) fusion.

FIG. 11 (SEQ ID NOS 25–42, respectfully) shows the sequences of the annealed oligonucleotide pairs used to construct plasmids PTW6165, pTW6166, pTW6175, pBG028, pTW6183, pTW6184, pTW6185, pTW6173, and pTW6174.

FIG. 12 (SEQ ID NOS 84 AND 85) shows the sequence of plasmid PTW6166 encoding the fusion of yeast alpha-factor and KPI(-4→57; M15A, S17Y).

FIG. 13 (SEQ ID NOS 86 AND 87) shows the sequence of plasmid PTW6175 encoding the fusion of yeast alpha-factor and KPI(-4→57; M15L, S17F).

FIG. 14 shows (SEQ ID NOS 88 AND 89) the sequence of plasmid PBG028 encoding the fusion of yeast alpha-factor and KPI(-4→57; M15L, S17Y).

FIG. 15 (SEQ ID NOS 90 AND 91) shows the sequence of plasmid PTW6183 encoding the fusion of yeast alpha-factor and KPI(-4→57; I16H, S17F).

FIG. 16 (SEQ ID NOS 92 AND 93) shows the sequence of plasmid PTW6184 encoding the fusion of yeast alpha-factor and KPI(-4→57; I16H, S17Y).

FIG. 17 (SEQ ID NOS 94 AND 95) shows the sequence of plasmid PTW6185 encoding the fusion of yeast alpha-factor and KPI(-4→57; I16H, S17W).

FIG. 18 (SEQ ID NOS 96 AND 97) shows the sequence of plasmid PTW6173 encoding the fusion of yeast alpha-factor and KPI(-4→57; M15A, I16H).

FIG. 19 (SEQ ID NOS 98 AND 99) shows the sequence of plasmid PTW6174 encoding the fusion of yeast alpha-factor and KPI(-4→57; M15L, I16H).

FIG. 20 shows the amino acid sequence (SEQ ID NO:83) of KPI (-4→57; M15A, S17W).

FIG. 21 shows the amino acid sequence (SEQ ID NO:85) of KPI (-4→57; M15A, S17Y).

FIG. 22 shows the amino acid sequence (SEQ ID NO:87) of KPI (-4→57; M15L, S17F).

FIG. 23 shows the amino acid sequence (SEQ ID NO:89) of KPI (-4→57; M15L, S17Y).

FIG. 24 shows the amino acid sequence (SEQ ID NO:91) of KPI (-4→57; I16H, S17F).

FIG. 25 shows the amino acid sequence (SEQ ID NO:93) of KPI (-4→57; I16H, S17Y).

FIG. 26 shows the amino acid sequence (SEQ ID NO:95) of KPI (-4→57; I16H, S17W).

FIG. 27 shows the amino acid sequence (SEQ ID NO:107) of KPI (-4→57; M15A, S17F).

FIG. 28 shows the amino acid sequence (SEQ ID NO:97) of KPI (-4→57; M15A, I16H).

FIG. 29 shows the amino acid sequence (SEQ ID NO:99) of KPI (-4→57; M15L, I16H).

FIG. 38 (SEQ ID NOS 100 AND 101) shows the coding region for the fusion of phoA-KPI (1→55)-geneIII.

FIG. 41 (SEQ ID NOS 102 AND 103) shows the expression unit encoded by the members of KPI Library 16–19.

FIG. 42 (SEQ ID NOS 104 AND 105) shows the phoA-KPI(1→55)-geneIII region encoded by the most frequently occurring randomized KPI region.

FIG. 44 (SEQ ID NOS 106 AND 107) shows the sequence of alpha-factor fused to KPI (-4→57; M15A, S17F).

FIG. 45 shows the inhibition constants ($K_i$s) determined for purified KPI variants against the selected serine proteases kallikrein, factor Xa, and factor XIIa.

FIGS. 46A–46E (SEQ ID NOS 108–228, respectfully) show the inhibition constants ($k_i$s) determined for KPI variants against kallikrein, plasmin, and factors $X_a$, $XI_a$, and $XII_a$.

FIG. 49 shows the oxygen tension in the presence and absence of KPI, before CPB, immediately after CPB, and at 60 and 180 minutes after the end of CPB.

FIG. 50 summarizes the results shown in FIGS. 47–49.

DETAILED DESCRIPTION

Figure 1:
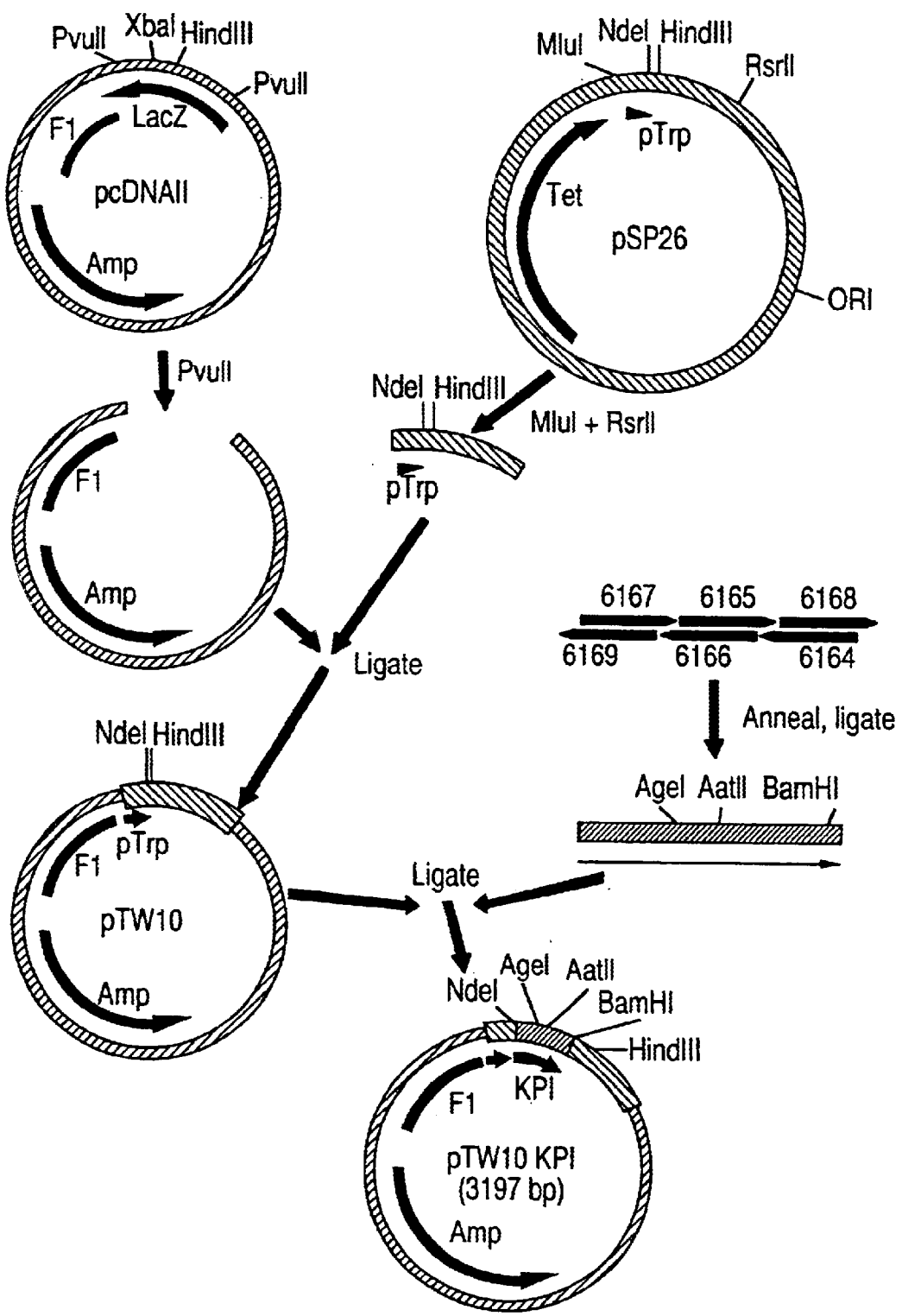
FIG. 1 shows the strategy for the construction of plasmid pTW10:KPI.

The present invention provides peptides that can bind to and preferably inhibit the activity of serine proteases. These inhibitory peptides can also provide a means of ameliorating, treating or preventing clinical conditions associated with increased activity of serine proteases. The novel peptides of the present invention preferably exhibit a more potent and specific (i.e., greater) inhibitory effect toward serine proteases of interest than known serine protease inhibitors. Examples of such proteases include: kallikrein; chymotrypsins A and B; trypsin; elastase; subtilisin; coagulants and procoagulants, particularly those in active form, including coagulation factors such as factors VIIa, IXa, Xa, XIa, and XIIa; plasmin; thrombin; proteinase-3; enterokinase; acrosin; cathepsin; urokinase; and tissue plasminogen activator.

Peptides of the present invention may be used to reduce the tissue damage caused by activation of the proteases of the contact pathway of the blood during surgical procedures such as cardiopulmonary bypass (CPB). Inhibition of contact pathway proteases reduces the "whole body inflammatory response" that can accompany contact pathway activation, and that can lead to tissue damage, and possibly death. The peptides of the present invention may also be used in conjunction with surgical procedures to reduce activated serine protease-associated perioperative and postoperative blood loss. For instance, perioperative blood loss of this type may be particularly severe during CPB surgery. Pharmaceutical compositions comprising the peptides of the present invention may be used in conjunction with surgery such as CPB; administration of such compositions may occur preoperatively, perioperatively or postoperatively. Examples of other clinical conditions associated with increased serine protease activity for which the peptides of the present invention may be used include: CPB-induced inflammatory response; post-CPB pulmonary injury; pancreatitis; allergy-induced protease release; deep vein thrombosis; thrombocytopenia; rheumatoid arthritis; adult respiratory distress syndrome; chronic inflammatory bowel disease; psoriasis; hyperfibrinolytic hemorrhage; organ preservation; wound healing; and myocardial infarction. Other examples of preferable uses of the peptides of the present invention are described in U.S. Pat. No. 5,187,153.

The invention is based upon the novel substitution of amino acid residues in the peptide corresponding to the naturally occurring KPI protease inhibitor domain of human amyloid β-amyloid precursor protein (APPI). These substitutions produce peptides that can bind to serine proteases and preferably exhibit an inhibition of the activity of serine proteases. The peptides also preferably exhibit a more potent and specific serine protease inhibition than known serine protease inhibitors. In accordance with the invention, peptides are provided that may exhibit a more potent and specific inhibition of one or more serine proteases of interest, e.g., kallikrein, plasmin and factors Xa, XIa, XIIa, and XIIa.

The present invention also includes pharmaceutical compositions comprising an effective amount of at least one of the peptides of the invention, in combination with a pharmaceutically acceptable sterile vehicle, as described in REMINGTON'S PHARMACEUTICAL SCIENCES: DRUG RECEPTORS AND RECEPTOR THEORY, (18th ed.), Mack Publishing Co., Easton, Pa. (1990).

A. Selection of Sequences of KPI Variants

The sequence of KPI is shown in Table 1. Table 2 shows a comparison of this sequence with that of aprotinin, with which it shares about 45% sequence identity. The numbering convention for KPI shown in Table 1 and used hereinafter designates the first glutamic acid residue of KPI as residue 1. This corresponds to residue number 3 using the standard numbering convention for aprotinin.

The crystal structure for KPI complexed with trypsin has been determined. See Perona et al., *J. Mol. Biol.* 230:919 (1993). The three-dimensional structure reveals two binding loops within KPI that contact the protease. The first loop extends from residue $Thr^9$ to $Ile^{16}$, and the second loop extends from residue $Phe^{32}$ to $Gly^{37}$. The two protease binding loops are joined through the disulfide bridge extending from $Cys^{12}$ to $Cys^{36}$. KPI contains two other disulfide bridges, between $Cys^3$ and $Cys^{53}$, and between $CyS^{28}$ to $Cys^{49}$.

This structure was used as a guide to inform our strategy for making the amino acid residue substitutions that will be most likely to affect the protease inhibitory properties of KPI. Our examination of the structure indicated that certain amino acid residues, including residues 9, 11, 13–18, 32, and 37–40, appear to be of particular significance in determining the protease binding properties of the KPI peptide. In a preferred embodiment of the invention two or more of those KPI peptide residues are substituted; such substitutions preferably occurring among residues 9, 11, 13–18, 32, and 37–40. In particular, we found that those substituted peptides, including peptides comprising substitutions of at least two of the four residues at positions 15–18, may exhibit more potent and specific serine protease inhibition toward selected serine proteases of interest than exhibited by the natural KPI peptide domain. Such substituted peptides may further comprise one or more additional substitutions at residues 9, 11, 13, 14, 32 and 37–40; in particular, such peptides may further comprise a substitution at positions 9 or 37. In particular, the peptides of the present invention preferably exhibit a greater potency and specificity for inhibiting one or more serine proteases of interest (e.g., kallikrein, plasmin and factors VIIa, IXa, Xa, XIa, and XIIa) than the potency and specificity exhibited by native KPI or other known serine protease inhibitors. That greater potency and specificity may be manifested by the peptides of the present invention by exhibiting binding constants for serine proteases of interest that are less than the binding constants exhibited by native KPI, or other known serine protease inhibitors, for such proteases.

By way of example, and as set forth in greater detail below, the serine protease inhibitory properties of peptides of the present invention were measured for the serine proteases of interest—kallikrein, plasmin and factors Xa, XIa, and XIIa. Methodologies for measuring the inhibitory properties of the KPI variants of the present invention are known to those skilled in the art, e.g., by determining the inhibition constants of the variants toward serine proteases of interest, as described in Example 4, infra. Such studies measure the ability of the novel peptides of the present invention to bind to one or more serine proteases of interest and to preferably exhibit a greater potency and specificity for inhibiting one or more serine protease of interest than known serine protease inhibitors such as native KPI.

The ability of the peptides of the present invention to bind one or more serine proteases of interest, particularly the ability of the peptides to exhibit such greater potency and specificity toward serine proteases of interest, manifest the clinical and therapeutic applications of such peptides. The clinical and therapeutic efficacy of the peptides of the present invention can be assayed by in vitro and in vivo methodologies known to those skilled in the art, e.g., as described in Example 5, infra.

TABLE 1

(SEQ ID NO:6):
SEQUENCE OF KPI:

```
 1                  10                  20                  30
 V R E V C S E Q A E T G P C R A M I S R W Y F D V T E G K C A P 40                  50
 F F Y G G C G G N R N N F D T E E Y C M A V C G S A I
```

TABLE 2

(SEQ ID NOS 6 AND 7):
COMPARISON OF KPI AND APROTININ SEQUENCES:

```
              1         10        20   30        40        50
KPI:    VREVCSEQAETGPCRAMISRWYFDVTEGKCAPFFYGGCGGNRNNFDTEEYCMAVCGSAI
               |  |   ||||  |  |       | |   ||||    ||||    | ||    || |
BPTI:   RPDFCLEPPYTGPCKARIIRYFYNAKAGLCQTFVYGGCRAKRNNFKSAEDCMRTCGGA
              1         10        20        30        40        50
```

B. Methods of Producing KPI Variants

The peptides of the present invention can be created by synthetic techniques or recombinant techniques which employ genomic or cDNA cloning methods.

1. Production by Chemical Synthesis

Peptides of the present invention can be routinely synthesized using solid phase or solution phase peptide synthesis. Methods of preparing relatively short peptides such as KPI by chemical synthesis are well known in the art. KPI variants could, for example be produced by solid-phase peptide synthesis techniques using commercially available equipment and reagents such as those available from Milligen (Bedford, Mass.) or Applied Biosystems-Perkin Elmer (Foster City, Calif.). Alternatively, segments of KPI variants could be prepared by solid-phase synthesis and linked together using segment condensation methods such as those described by Dawson et al., *Science* 266:776 (1994). During chemical synthesis of the KPI variants, substitution of any amino acid is achieved simply by replacement of the residue that is to be substituted with a different amino acid monomer.

2. Production by Recombinant DNA Technology

(a) Preparation of genes encoding KPI variants

In a preferred embodiment of the invention, KPI variants are produced by recombinant DNA technology. This requires the preparation of genes encoding each KPI variant that is to be made. Suitable genes can be constructed by oligonucleotide synthesis using commercially available equipment, such as that provided by Milligen and Applied Biosystems, supra. The genes can be prepared by synthesizing the entire coding and non-coding strands, followed by annealing the two strands. Alternatively, the genes can be prepared by ligation of smaller synthetic oligonucleotides by methods well known in the art. Genes encoding KPI variants are produced by varying the nucleotides introduced at any step of the synthesis to change the amino acid sequence encoded by the gene.

Preferably, however, KPI variants are made by site-directed mutagenesis of a gene encoding KPI. Methods of site-directed mutagenesis are well known in the art. See, for example, Ausubel et al., (eds.) CURRENT PROTOCOLS IN MOLECULAR BIOLOGY (Wiley Interscience, 1987); PROTEIN ENGINEERING (Oxender & Fox eds., A. Liss, Inc. 1987). These methods require the availability of a gene encoding KPI or a variant thereof, which can then be mutagenized by known methods to produce the desired KPI variants. In addition, linker-scanning and polymerase chain reaction ("PCR") mediated techniques can be used for purposes of mutagenesis. See PCR TECHNOLOGY (Erlich ed., Stockton Press 1989); CURRENT PROTOCOLS IN MOLECULAR BIOLOGY, vols. 1 & 2, loc. cit.

A gene encoding KPI can be obtained by cloning the naturally occurring gene, as described for example in U.S. Pat. Nos. 5,223,482 and 5,187,153, which are hereby incorporated by reference in their entireties. In particular, see columns 6–9 of U.S. Pat. No. 5,187,153. See also PCT application Ser. No. 93/09233. In a preferred embodiment of the invention a synthetic gene encoding KPI is produced by chemical synthesis, as described above. The gene may encode the 57-amino acid KPI domain shown in Table 1, or it may also encode additional N-terminal amino acids from the APPI protein sequence, such as the four amino acid sequence (SEQ ID NO:8) (Glu-Val-Val-Arg, designated residues –4 to –1) immediately preceding the KPI domain in APPI.

Production of the gene by synthesis allows the codon usage of the KPI gene to be altered to introduce convenient restriction endonuclease recognition sites, without altering the sequence of the encoded peptide. In a preferred embodiment of the invention, the synthetic KPI gene contains restriction endonuclease recognition sites that facilitate excision of DNA cassettes from the KPI gene. These cassettes can be replaced with small synthetic oligonucleotides encoding the desired changes in the KPI peptide sequence. See Ausubel, supra.

This method also allows the production of genes encoding KPI as a fusion peptide with one or more additional peptide or protein sequences. The DNA encoding these additional sequences is arranged in-frame with the sequence encoding KPI such that, upon translation of the gene, a fusion protein of KPI and the additional peptide or protein sequence is produced. Methods of making such fusion proteins are well known in the art. Examples of additional peptide sequences that can be encoded in the genes are secretory signal peptide sequences, such as bacterial leader sequences, for example ompA and phoA, that direct secretion of proteins to the bacterial periplasmic space. In a preferred embodiment of the invention, the additional peptide sequence is a yeast secretory signal sequence, such as α-mating factor, that directs secretion of the peptide when produced in yeast.

Additional genetic regulatory sequences can also be introduced into the synthetic gene that are operably linked to the coding sequence of the gene, thereby allowing synthesis of the protein encoded by the gene when the gene is introduced into a host cell. Examples of regulatory genetic sequences that can be introduced are: promoter and enhancer sequences and transcriptional and translational control sequences. Other regulatory sequences are well known in the art. See Ausubel et al., supra, and Sambrook et al., *supra*.

Sequences encoding other fusion proteins and genetic elements are well known to those of skill in the art. In a preferred embodiment of the invention, the KPI sequence is prepared by ligating together synthetic oligonucleotides to produce a gene encoding an in-frame fusion protein of yeast α-mating factor with either KPI (1→57) or KPI (-4→57).

The gene constructs prepared as described above are conveniently manipulated in host cells using methods of manipulating recombinant DNA techniques that are well known in the art. See, for example Sambrook et al., MOLECULAR CLONING: A LABORATORY MANUAL, Second Edition, (Cold Spring Harbor Laboratory Press, Cold Spring Harbor, N.Y. 1989), and Ausubel, supra. In a preferred embodiment of the invention the host cell used for manipulating the KPI constructs is E. coli. For example, the construct can be ligated into a cloning vector and propagated in E. coli by methods that are well known in the art. Suitable cloning vectors are described in Sambrook, supra, or are commercially available from suppliers such as Promega (Madison, Wis.), Stratagene (San Diego, Calif.) and Life Technologies (Gaithersburg, Md.).

Once a gene construct encoding KPI has been obtained, genes encoding KPI variants are obtained by manipulating the coding sequence of the construct by standard methods of site-directed mutagenesis, such as excision and replacement of small DNA cassettes, as described supra. See Ausubel, supra, and Sinha et al., supra. See also U.S. Pat. No. 5,373,090, which is herein incorporated by reference in its entirety. See particularly, columns 4–12 of U.S. Pat. No. 5,272,090. These genes are then used to produce the KPI variant peptides as described below.

Alternatively, KPI variants can be produced using phage display methods. See, for example, Dennis et al. supra, which is hereby incorporated by reference in its entirety. See also U.S. Pat. Nos. 5,223,409 and 5,403,484, which are hereby also incorporated by reference in their entireties. In these methods, libraries of genes encoding variants of KPI are fused in-frame to genes encoding surface proteins of filamentous phage, and the resulting peptides are expressed (displayed) on the surface of the phage. The phage are then screened for the ability to bind, under appropriate conditions, to serine proteases of interest immobilized on a solid support. Large libraries of phage can be used, allowing simultaneous screening of the binding properties of a large number of KPI variants. Phage that have desirable binding properties are isolated and the sequences of the genes encoding the corresponding KPI variants is determined. These genes are then used to produce the KPI variant peptides as described below.

(b) Expression of KPI variant peptides Once genes encoding KPI variants have been prepared, they are inserted into an expression vector and used to produce the recombinant peptide. Suitable expression vectors and corresponding methods of expressing recombinant proteins and peptides are well known in the art. Methods of expressing KPI peptides are described in U.S. Pat. No. 5,187,153, columns 9–11, U.S. Pat. No. 5,223,482, columns 9–11, and PCT application 93/09233, pp. 49–67. See also Ausubel et al., supra, and Sambrook et al., supra. The gene can be expressed in any number of different recombinant DNA expression systems to generate large amounts of the KPI variant, which can then be purified and tested for its ability to bind to and inhibit serine proteases of interest.

Examples of expression systems known to the skilled practitioner in the art include bacteria such as E. coli, yeast such as Saccharomyces cerevisiae and Pichia pastoris, baculovirus, and mammalian expression systems such as in Cos or CHO cells. In a preferred embodiment, KPI variants are expressed in S. cerevisiae. In another preferred embodiment the KPI variants are cloned into expression vectors to produce a chimeric gene encoding a fusion protein of the KPI variant with yeast α-mating factor. The mating factor acts as a signal sequence to direct secretion of the fusion protein from the yeast cell, and is then cleaved from the fusion protein by a membrane-bound protease during the secretion process. The expression vector is transformed into S. cerevisiae, the transformed yeast cells are cultured by standard methods, and the KPI variant is purified from the yeast growth medium.

Recombinant bacterial cells expressing the peptides of the present invention, for example, E. coli, are grown in any of a number of suitable media, for example LB, and the expression of the recombinant antigen induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate dense inclusion bodies and cell membranes from the soluble cell components. This centrifugation can be performed under conditions whereby dense inclusion bodies are selectively enriched by incorporation of sugars such as sucrose into the buffer and centrifugation at a selective speed. If the recombinant peptide is expressed in inclusion bodies, as is the case in many instances, these can be washed in any of several solutions to assist in the removal of any contaminating host proteins, then solubilized in solutions containing high concentrations of urea (e.g., 8M) or chaotropic agents such as guanidine hydrochloride in the presence of reducing agents such as β-mercaptoethanol or DTT (dithiothreitol).

At this stage it may be advantageous to incubate the peptides of the present invention for several hours under conditions suitable for the peptides to undergo a refolding process into a conformation which more closely resembles that of native KPI. Such conditions generally include low protein concentrations less than 500 µg/ml, low levels of reducing agent, concentrations of urea less than 2M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule (which can be obtained from animals vaccinated with the native molecule isolated from parasites). Following refolding, the peptide can then be purified further and separated from the refolding mixture by chromatography on any of several supports including ion exchange resins, gel permeation resins or on a variety of affinity columns.

Purification of KPI variants can be achieved by standard methods of protein purification, e.g., using various chromatographic methods including high performance liquid chromatography and adsorption chromatography. The purity and the quality of the peptides can be confirmed by amino acid analyses, molecular weight determination, sequence determination and mass spectrometry. See, for example, PROTEIN PURIFICATION METHODS—A PRACTICAL APPROACH, Harris et al., eds. (IRL Press, Oxford, 1989). In a preferred embodiment, the yeast cells are removed from the growth medium by filtration or centrifugation, and the KPI variant is purified by affinity chromatography on a column of trypsin-agarose, followed by reversed-phase HPLC.

C. Measurement of Protease Inhibitory Properties of KPI Variants

Once KPI variants have been purified, they are tested for their ability to bind to and inhibit serine proteases of interest in vitro. The peptides of the present invention preferably exhibit a more potent and specific inhibition of serine proteases of interest than known serine protease inhibitors, such as the natural KPI peptide domain. Such binding and inhibition can be assayed for by determining the inhibition constants for the peptides of the present invention toward serine proteases of interest and comparing those constants with constants determined for known serine protease inhibitors, e.g., the native KPI domain, toward those proteases. Methods for determining inhibition constants of protease inhibitors are well known in the art. See Fersht, ENZYME STRUCTURE AND MECHANISM, 2nd ed., W.H. Freeman and Co., New York, (1985).

In a preferred embodiment the inhibition experiments are carried out using a chromogenic synthetic protease substrate, as described, for example, in Bender et al., *J. Amer. Chem. Soc.* 88:5890 (1966). Measurements taken by this method can be used to calculate inhibition constants ($K_i$ values) of the peptides of the present invention toward serine proteases of interest. See Bieth in BAYER-SYMPOSIUM V "PROTEINASE INHIBITORS", Fritz et al., eds., pp. 463–69, Springer-Verlag, Berlin, Heidelberg, New York, (1974). KPI variants that exhibit potent and specific inhibition of one or more serine proteases of interest may subsequently be tested in vivo. In vitro testing, however, is not a prerequisite for in vivo studies of the peptides of the present invention.

D. Testing of KPI Variants in vivo

The peptides of the present invention may be tested, alone or in combination, for their therapeutic efficacy by various in vivo methodologies known to those skilled in the art, e.g., the ability of KPI variants to reduce postoperative bleeding can be tested in standard animal models. For example, cardiopulmonary bypass surgery can be carried out on animals such as pigs in the presence of KPI variants, or in control animals where the KPI variant is not used. The use of pigs as a model for studying the clinical effects associated with CPB has previously been described. See Redmond et al., *Ann. Thorac. Surg.* 56:474 (1993).

The KPI variant is supplied to the animals in a pharmaceutical sterile vehicle by methods known in the art, for example by continuous intravenous infusion. Chest tubes can be used to collect shed blood for a defined period of time. The shed blood, together with the residual intrathoracic blood found after sacrifice of the animal can be used to calculate hemoglobin (Hgb) loss. The postoperative blood and Hgb loss is then compared between the test and control animals to determine the effect of the KPI variants.

E. Therapeutic Use of KPI Variants

KPI variants of the present invention found to exhibit therapeutic efficacy (e.g., reduction of blood loss following surgery in animal models) may preferably be used and administered, alone or in combination or as a fusion protein, in a manner analogous to that currently used for aprotinin or other known serine protease inhibitors. See Butler et al., supra. Peptides of the present invention generally may be administered in the manner that natural peptides are administered. A therapeutically effective dose of the peptides of the present invention preferably affects the activity of the serine proteases of interest such that the clinical condition may be treated, ameliorated or prevented. Therapeutically effective dosages of the peptides of the present invention can be determined by those skilled in the art, e.g., through in vivo or in vitro models. Generally, the peptides of the present invention may be administered in total amounts of approximately 0.01 to approximately 500, specifically 0.1 to 100 mg/kg body weight, if desired in the form of one or more administrations, to achieve therapeutic effect. It may, however, be necessary to deviate from such administration amounts, in particular depending on the nature and body weight of the individual to be treated, the nature of the medical condition to be treated, the type of preparation and the administration of the peptide, and the time interval over which such administration occurs. Thus, it may in some cases be sufficient to use less than the above amount of the peptides of the present invention, while in other cases the above amount is preferably exceeded. The optimal dose required in each case and the type of administration of the peptides of the present invention can be determined by one skilled in the art in view of the circumstances surrounding such administration. Such peptides can be administered by intravenous injections, in situ injections, local applications, inhalation, oral administration using coated polymers, dermal patches or other appropriate means. Compositions comprising peptides of the present invention are advantageously administered in the form of injectable compositions. Such peptides may be preferably administered to patients via continuous intravenous infusion, but can also be administered by single or multiple injections. A typical composition for such purpose comprises a pharmaceutically acceptable carrier. Pharmaceutically acceptable carriers include aqueous solutions, non-toxic excipients, including salts, preservatives, buffers and the like, as described in REMINGTON'S PHARMACEUTICAL SCIENCES, pp. 1405–12 and 1461–87 (1975) and THE NATIONAL FORMULARY XIV., 14th Ed. Washington: American Pharmaceutical Association (1975). Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the composition are adjusted according to routine skills in the art. See GOODMAN AND GILMAN'S THE PHARMACOLOGICAL BASIS FOR THERAPEUTICS (7th ed.). The peptides of the present invention may be present in such pharmaceutical preparations in a concentration of approximately 0.1 to 99.5% by weight, specifically 0.5 to 95% by weight, relative to the total mixture. Such pharmaceutical preparations may also comprise other pharmaceutically active substances in addition to the peptides of the present invention. Other methods of delivering the peptides to patients will be readily apparent to the skilled artisan.

Examples of mammalian serine proteases that may exhibit inhibition by the peptides of the present invention include: kallikrein; chymotrypsins A and B; trypsin; elastase; subtilisin; coagulants and procoagulants, particularly those in active form, including coagulation factors such as thrombin and factors VIIa, IXa, Xa, XIa, and XIIa; plasmin; proteinase-3; enterokinase; acrosin; cathepsin; urokinase; and tissue plasminogen activator. Examples of conditions associated with increased serine protease activity include: CPB-induced inflammatory response; post-CPB pulmonary injury; pancreatitis; allergy-induced protease release; deep vein thrombosis; thrombocytopenia; rheumatoid arthritis; adult respiratory distress syndrome; chronic inflammatory bowel disease; psoriasis; hyperfibrinolytic hemorrhage; organ preservation; wound healing; and myocardial infarction. Other examples of the use of the peptides of the present invention are described in U.S. Pat. No. 5,187,153.

The inhibitors of the present invention may also be used for inhibition of serine protease activity in vitro, for example during the preparation of cellular extracts to prevent degradation of cellular proteins. For this purpose the inhibitors of the present invention may preferably be used in a manner analogous to the way that aprotinin, or other known serine protease inhibitors, are used. The use of aprotinin as a protease inhibitor for preparation of cellular extracts is well known in the art, and aprotinin is sold commercially for this purpose.

The present invention, thus generally described, will be understood more readily by reference to the following examples, which are provided by way of illustration and are not intended to be limiting of the present invention.

EXAMPLES

Example 1

Expression of Wild-type KPI (-4→57)

A. Construction of PTW10:KPI

Plasmid PTW10:KPI is a bacterial expression vector encoding the 57 amino acid form of KPI fused to the bacterial phoA signal sequence. The strategy for the construction of PTW10:KPI is shown in FIG. 1.

Plasmid pcDNAII (Invitrogen, San Diego, Calif.) was digested with PvuII and the larger of the two resulting PvuII fragments (3013 bp) was isolated. Bacterial expression plasmid pSP26 was digested with MluI and RsrII, and the 409 bp MluI-RsrII fragment containing the pTrp promoter element and transcription termination signals was isolated by electrophoresis in a 3% NuSieve Agarose gel (FMC Corp., Rockland, Me.). Plasmid pSP26, containing a heparin-binding EGF-like growth factor (HB-EGF) insert between the NdeI and HindIII sites, is described as pNA28 in Thompson et al., *J. Biol. Chem.* 269:2541 (1994). Plasmid pSP26 was deposited in host *E. coli* W3110, pSP26 with the American Type Culture Collection (ATCC), 12301 Parklawn Drive, Rockville, Md., 20852, USA under the conditions specified by the Budapest Treaty on the International Recognition of the Deposit of Microorganisms (Budapest Treaty). Host *E. coli* W3110, pSP26 was deposited on May 3, 1995 and given Accession No. 69800. Availability of the deposited plasmid is not to be construed as a license to practice the invention in contravention of the rights granted under the authority of any government in accordance with its patent laws.

The ends of the MluI-RsrII fragment were blunted using DNA polymerase Klenow fragment by standard techniques. The blunted fragment of pSP26 was then ligated into the large PvuII fragment of plasmid PCDNAII, and the ligation mixture was used to transform *E. coli* strain MC1061. Ampicillin-resistant colonies were selected and used to isolate plasmid pTW10 by standard techniques.

A synthetic gene was constructed encoding the bacterial phoA secretory signal sequence fused to the amino terminus of KPI (1→57). The synthetic gene contains cohesive ends for NdeI and HindIII, and also incorporates restriction endonuclease recognition sites for AgeI, RsrII, AatII and BamHI, as shown in FIG. 2. The synthetic phoA-KPI gene was constructed from 6 oligonucleotides of the following sequences (shown 5'→3'):

6167 (SEQ ID NO:9): TATGAAACAAAGCACTATTG-CACTGGCACTCTTACCGTTACTGTTTAC-CCCTGTGACAAAAGCCGAGGTGTGCTCTGAA 6169 (SEQ ID NO:10): CTCGGCTTTTGTCA-CAGGGGTAAACAGTAACGGTAAGAGTGC-CAGTGCAATAGTGCTTTGTTTCATA 6165 (SEQ ID NO:11): CAAGCTGAGACCGGTCCGT-GCCGTGCAATGATCTCCCGCTGGTACTTT-GACGTCACTGAAGGTAAGTGCGCTCCAT-TCTTT 6166 (SEQ ID NO:12): GCACTTACCTTCAGT-GACGTCAAAGTACCAGCGGGAGATCAT-TGCACGGCACGGACCGGTCTCAGCTTGT-TCAGAGCACAC 6168 (SEQ ID NO:13): TACGGCGGTTGCGGCG-GCAACCGTAACAACTTTGACACTGAA-GAGTACTGCATGGCAGTGTGCGGATC-CGCTATTTAAGCT 6164 (SEQ ID NO:14): AGCTTAAATAGCGGATCCG-CACACTGCCATGCAGTACTCTTCAGTGT-CAAAGTTGTTACGGTTGCCGCCGCAAC-CGCCGTAAAAGAATGGAGC

The oligonucleotides were phosphorylated and annealed in pairs: 6167+6169, 6165+6166, 6168+6164. In 20 μl T4 DNA Ligase Buffer (New England Biolabs, Beverley, Mass.), 1 μg of each oligonucleotide pair was incubated with 10 U T4 Polynucleotide Kinase (New England Biolabs) for 1 h at 37° C., then heated to 95° C. for 1 minute, and slow-cooled to room temperature to allow annealing. All three annealed oligo pairs were then mixed for ligation to one another in a total volume of 100 μl T4 DNA Ligase Buffer, and incubated with 400 U T4 DNA Ligase (New England Biolabs) overnight at 15° C. The ligation mixture was extracted with an equal volume of phenol:CHCl₃ (1:1), ethanol-precipitated, resuspended in 50 μl Restriction Endonuclease Buffer #4 (New England Biolabs) and digested with NdeI and HindIII. The annealed, ligated and digested oligos were then subjected to electrophoresis in a 3% NuSieve Agarose gel, and the 240 bp NdeI-HindIII fragment was excised. This gel-purified synthetic gene was ligated into plasmid pTW10 which had previously been digested with NdeI and HindIII, and the ligation mixture was used to transform *E. coli* strain MC1061. Ampicillin-resistant colonies were selected and used to prepare plasmid pTW10:KPI. This plasmid contains the phoA-KPI(1→57) fusion protein inserted between the pTrp promoter element and the transcription termination signals.

B. Construction of pKPI-61

Figure 3:
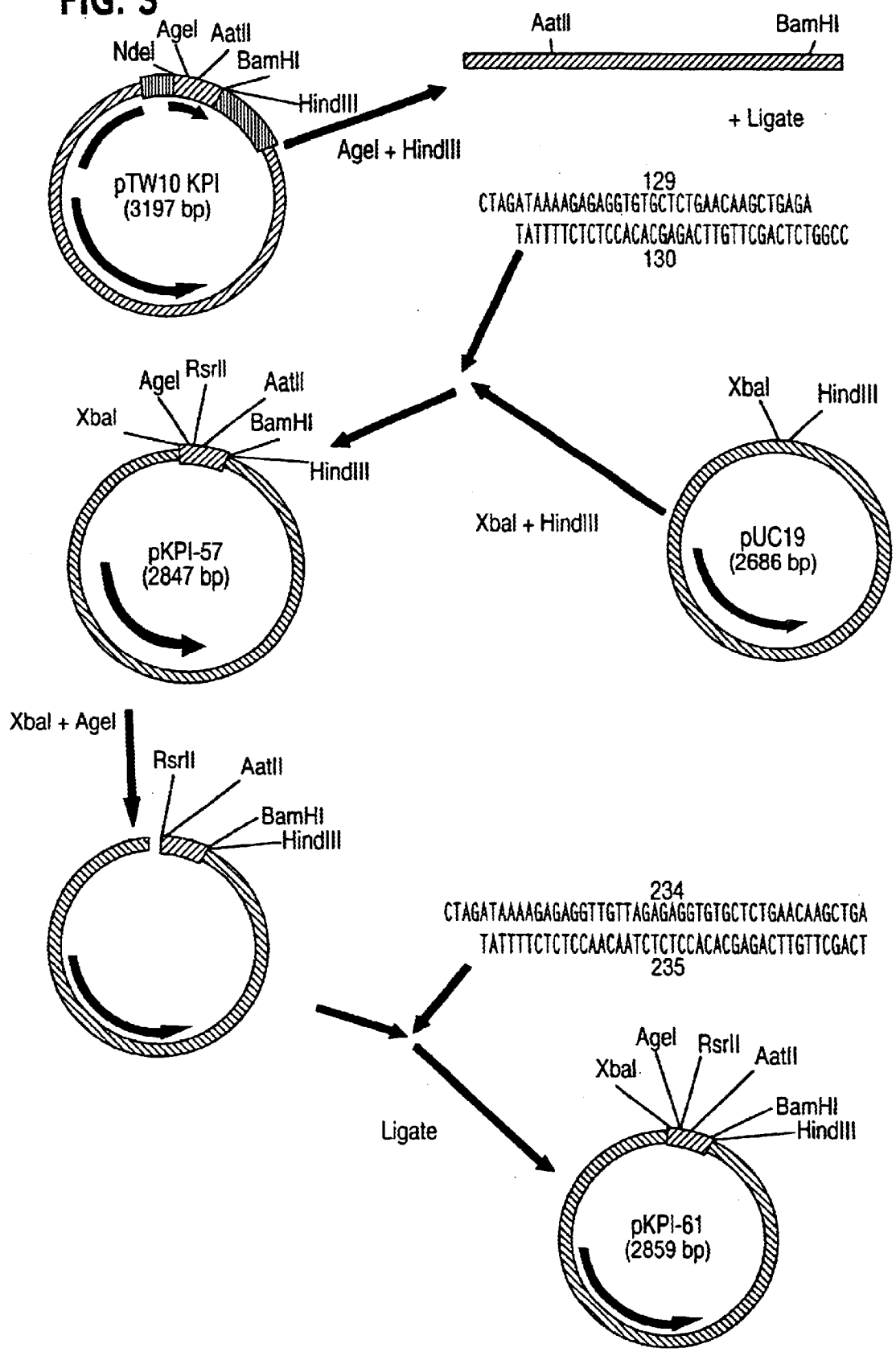
FIG. 3 (SEQ ID NOS 15–18) shows the strategy for construction of plasmid pKPI-61.

The strategy for constructing pKPI-61 is shown in FIG. 3. Plasmid pTW10:KPI was digested with AgeI and HindIII; the resulting 152 bp AgeI-HindIII fragment containing a portion of the KPI synthetic gene was isolated by preparative gel electrophoresis. An oligonucleotide pair (129+130) encoding the 9 amino-terminal residues of KPI(1→57) and 4 amino acids of yeast α-mating factor was phosphorylated and annealed as described above.

129 (SEQ ID NO:15): CTAGATAAAAGAGAGGTGT-GCTCTGAACAAGCTGAGA 130 (SEQ ID NO:16): CCGGTCTCAGCTTGTTCA-GAGCACACCTCTCTTTTAT

The annealed oligonucleotides were then ligated to the AgeI-HindIII fragment of the KPI (1→57) synthetic gene. The resulting 192 bp XbaI-HindIII synthetic gene (shown in FIG. 4) was purified by preparative gel electrophoresis, and ligated into plasmid pUC19 which had previously been digested with XbaI and HindIII. The ligation products were used to transform *E. coli* strain MC1061. Ampicillin-resistant colonies were picked and used to prepare plasmid PKPI-57 by standard methods. To create a synthetic gene encoding KPI(-4→57), PKPI-57 was digested with XbaI and AgeI and the smaller fragment replaced with annealed oligos 234+235, which encode 4 amino acid residues of yeast α-mating factor fused a 4 amino acid residue amino-terminal extension of KPI (1→57).

234 (SEQ ID NO:17): CTAGATAAAAGAGAGGTTGT-TAGAGAGGTGTGCTCTGAACAAGCTGAGA 235 (SEQ ID NO:18): CCGGTCTCAGCTTGTTCA-GAGCACACCTCTCTAACAACCTCTCTTTTAT

The 4 extra amino acids are encoded in the amyloid β-protein precursor/protease nexin-2 (APPI) which contains the KPI domain. The synthetic 201 bp XbaI-HindIII fragment encoding KPI(-4→57) in pKPI-61 is shown in FIG. 5.

C. Assembly of pTW113

Figure 6:
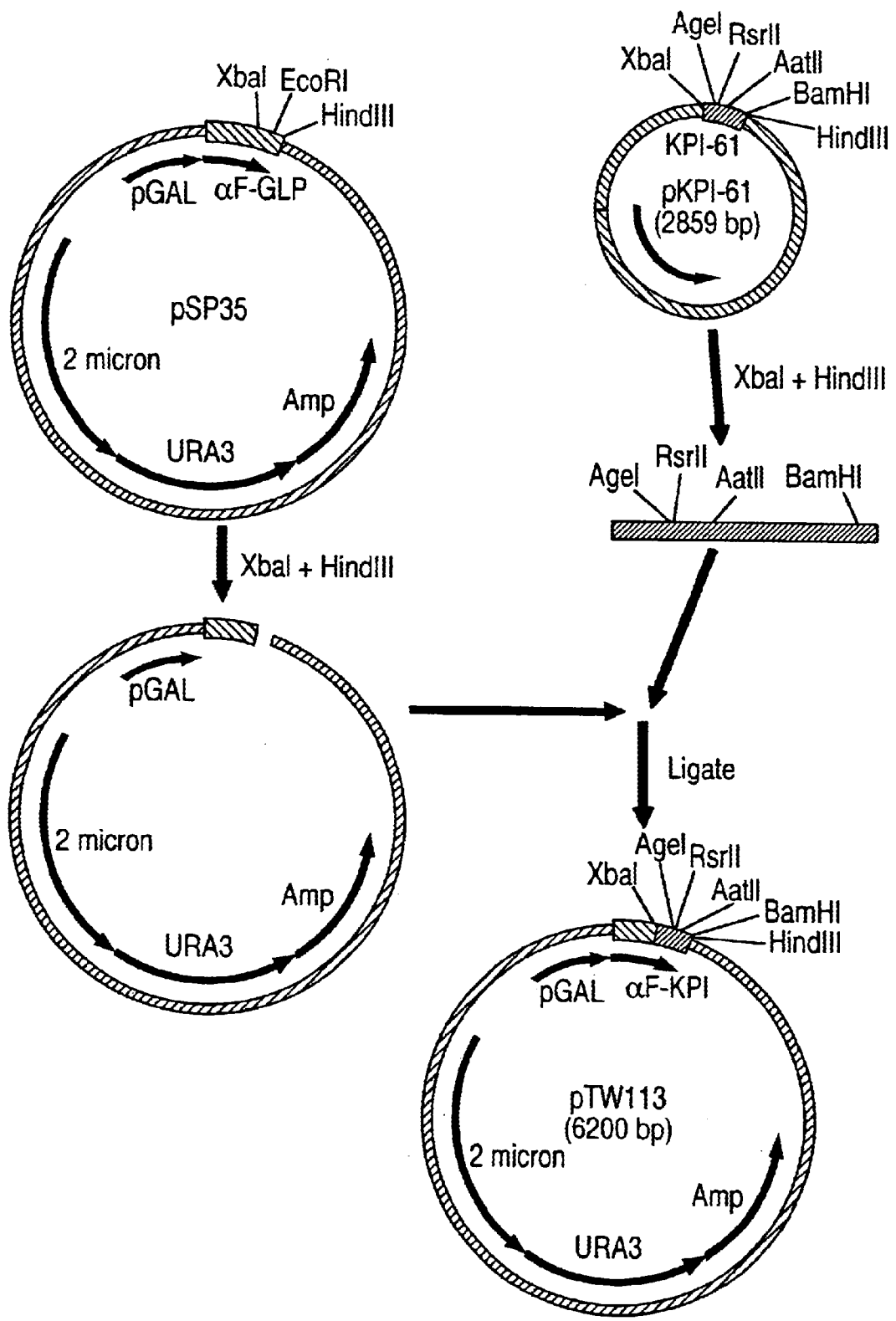
FIG. 6 shows the strategy for the construction of plasmid pTW113.

The strategy for the construction of PTW113 is shown in FIG. 6. Plasmid pSP35 was constructed from yeast expression plasmid pYES2 (Invitrogen, San Diego, Calif.) as follows. A 267 bp PvuII-XbaI fragment was generated by PCR from yeast α-mating factor DNA using oligos 6274 and 6273:

6274 (SEQ ID NO:19): GGGGGCAGCTGTATAAAC-GATTAAAA 6273 (SEQ ID NO:20): GGGGGTCTAGAGATAC-CCCTTCTTCTTTAG

This PCR fragment, encoding an 82 amino acid portion of yeast α-mating factor, including the secretory signal peptide and pro-region, was inserted into pYES2 that had been previously digested with PvuII and XbaI. The resulting plasmid is denoted pSP34.

Two oligonucleotide pairs, 6294+6292 were then ligated to 6290+6291, and the resulting 135 bp fragment was purified by gel electrophoresis.

6294 (SEQ ID NO:21): CTAGATAAAAGAGAGGCT-GAGGCTCACGCTGAAGGTACTTTCACTTC 6290 (SEQ ID NO:22): TGACGTCTCTTCTTACTT-GGAAGGTCAAGCTGCTAAGGAATTCATCGCTT-GGTTGGTCAAAGGTAGAGGTTAAGCTTA 6291 (SEQ ID NO:23): CTAGTAAGCTTAACCTCTAC-CTTTGACCAACCAAGCGATGAATTCCTTAGCA 6292 (SEQ ID NO:24): GCTTGACCTTCCAAGTAA-GAAGAGACGTCAGAAGTGAAAGTACCT-TCAGCGTGAGCCTCAGCCTCTCTTTTAT

The resulting synthetic fragment was ligated into the XbaI site of pSP34, resulting in plasmid pSP35. pSP35 was digested with XbaI and HindIII to remove the insert, and ligated with the 201 bp XbaI-HindIII fragment of pKPI-61, encoding KPI(-4→57). The resulting plasmid pTW113, encodes the 445 bp synthetic gene for the α-factor-KPI(-4→57) fusion. See FIG. 7.

D. Transformation of Yeast with pTW113

*Saccharomyces cerevisiae* strain ABL115 was transformed with plasmid pTW113 by electroporation by the method of Becker et al., *Methods Enzymol.* 194:182 (1991). An overnight culture of yeast strain ABL115 was used to inoculate 200 ml YPD medium. The inoculated culture was grown with vigorous shaking at 30° C. to an $OD_{600}$ of 1.3–1.5, at which time the cells were harvested by centrifugation at 5000 rpm for 5 minutes. The cell pellet was resuspended in 200 ml ice-cold water, respun, resuspended in 100 ml ice-cold water, then pelleted again. The washed cell pellet was resuspended in 10 ml ice-cold 1M sorbitol, recentrifuged, then resuspended in a final volume of 0.2 ml ice-cold 1M sorbitol. A 40 µl aliquot of cells was placed into the chamber of a cbld 0.2 cm electroporation cuvette (Invitrogen), along with 100 ng plasmid DNA for pTW113. The cuvette was placed into an Invitrogen Electroporator II and pulsed at 1500 V, 25 µF, 100 Ω. Electroporated cells were diluted with 0.5 ml 1M sorbitol, and 0.25 ml was spread on an SD agar plate containing 1M sorbitol. After 3 days' growth at 30° C., individual colonies were streaked on SD+CAA agar plates.

E. Induction of pTW113/ABL115, Purification of KPI(-4→57)

Yeast cultures were grown in a rich broth and the galactose promoter of the KPI expression vector induced with the addition of galactose as described by Sherman, *Methods Enzymol.* 194:3 (1991). A single well-isolated colony of pTW113/ABL115 was used to inoculate a 10 ml overnight culture in Yeast Batch Medium. The next day, 1L Yeast Batch Medium which had been made 0.2% glucose was inoculated to an $OD_{600}$ of 0.1 with the overnight culture. Following 24 hours at 30° C. with vigorous shaking, the 1L culture was induced by the addition of 20 ml Yeast Galactose Feed Medium. Following induction, the culture was fed every 12 hours with the addition of 20 ml Yeast Galactose Feed Medium. At 48 hours after induction, the yeast broth was harvested by centrifugation, then adjusted to pH 7.0 with 2M Tris, pH 10. The broth was subjected to trypsin-Sepharose affinity chromatography, and bound KPI(-4→57) was eluted with 20mM Tris pH 2.5. See Schilling et al., *Gene* 98:225 (1991). Final purification of KPI(-4→57) was accomplished by HPLC chromatography on a semi-prep Vydac C4 column in a gradient of 20% to 35% acetonitrile. The sample was dried and resuspended in PBS at 1–2 mg/ml. The amino acid sequence of KPI(-4→57) is shown in FIG. 8.

Example 2

Recombinant Expression of Site-directed KPI(-4→57) Variants

Expression vectors for the production of specific variants of KPI(-4→57) were all constructed using the pTW113 backbone as a starting point. For each KPI variant, an expression construct was created by replacing the 40 bp RsrII-AatII fragment of the synthetic KPI gene contained in pTW113 with a pair of annealed oligonucleotides which encode specific codons mutated from the wild-type KPI(-4→57) sequence. In the following Examples the convention used for designating the amino substituents in the KPI variants indicates first the single letter code for the amino acid found in wild-type KPI, followed by the position of the residue using the numbering convention described supra, followed by the code for the replacement amino acid. Thus, for example, M15R indicates that the methionine residue at position 15 is replaced by an arginine.

A. Construction of pTW6165

Figure 9:
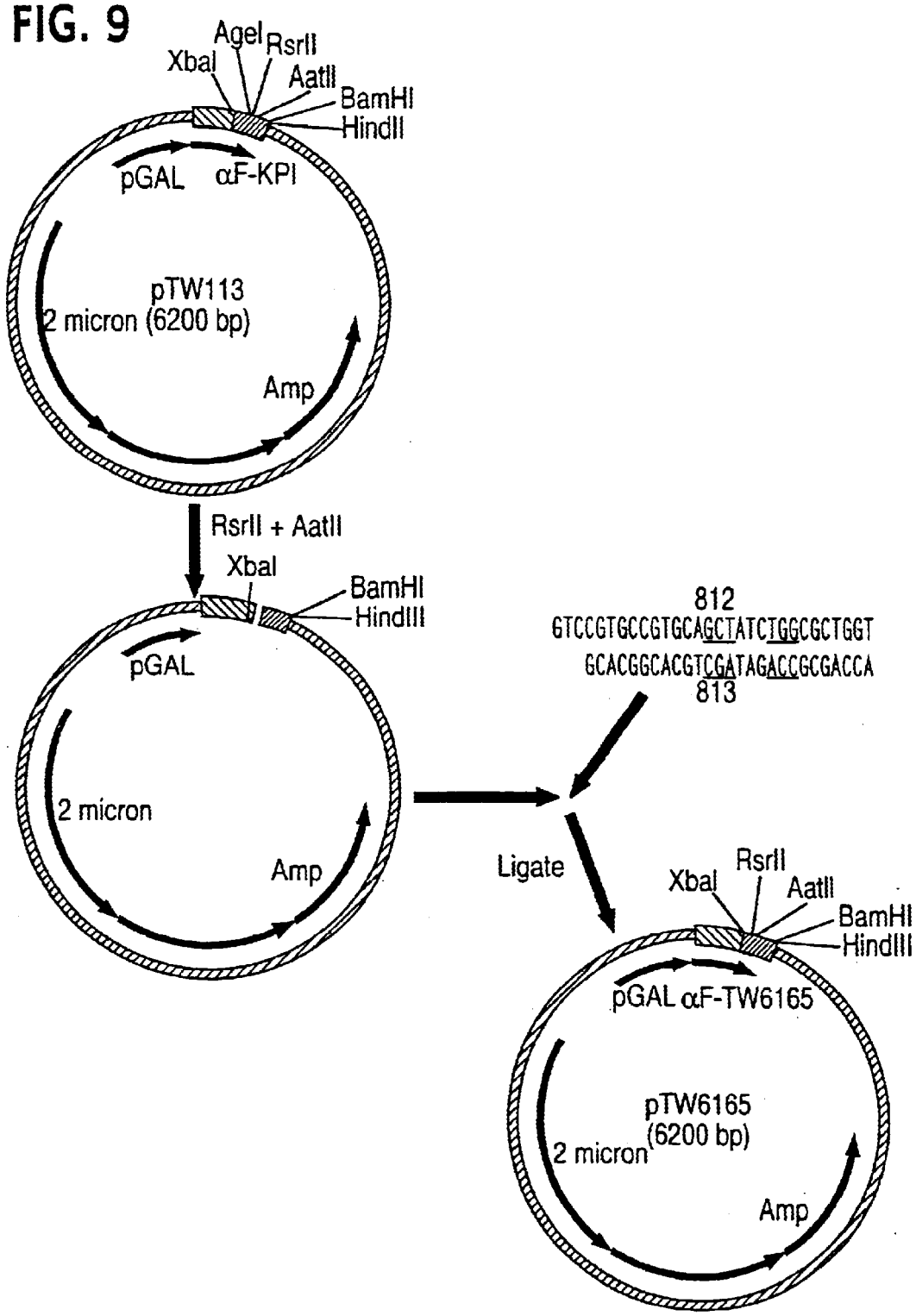
FIG. 9 (SEQ ID NOS 25 AND 26) shows the strategy for constructing plasmid pTW6165.

The strategy for constructing pTW6165 is shown in FIG. 9. Plasmid pTW113 was digested with RsrII and AatII, and the larger of the two resulting fragments was isolated. An oligonucleotide pair (812+813) was phosphorylated, annealed and gel-purified as described above.

812 (SEQ ID NO:25): GTCCGTGCCGTGCAGC-TATCTGGCGCTGGTACTTTGACGT 813 (SEQ ID NO:26): CAAAGTACCAGCGCCAGAT-AGCTGCACGGCACG

The annealed oligonucleotides were ligated into the RsrII and AatII-digested pTW113, and the ligation product was used to transform *E. coli* strain MC1061. Transformed colonies were selected by ampicillin resistance. The resulting plasmid, pTW6165, encodes the 445 bp synthetic gene for the α-factor-KPI(-4→57; M15A, S17W) fusion. See FIG. 10.

B. Construction of pTW6166, pTW6175, pBG028, pTW6183, pTW6184, pTW6185, pTW6173, pTW6174.

Construction of the following KPI (-4→57) variants was accomplished exactly as outlined for pTW6165. The oligonucleotides utilized for each construct are denoted below, and the sequences of annealed oligonucleotide pairs are shown in FIG. 11. FIGS. 12–19 show the synthetic genes for the α-factor fusions with each KPI(-4→57) variant.

pTW6166: KPI(-4→57; M15A, S17Y)—See FIG. 12

814 (SEQ ID NO:27): GTCCGTGCCGTGCAGCTATC-TACCGCTGGTACTTTGACGT 815 (SEQ ID NO:28): CAAAGTACCAGCGGTAGAT-
CAGCTGCACGGCACG pTW6175: KPI(-4→57; M15L, S17F)—See FIG. 13

867 (SEQ ID NO:29): GTCCGTGCCGTGCATTGATCT-
TCCGCTGGTACTTTGACGT 868 (SEQ ID NO:30): CAAAGTACCAGCGGAAGAT-
CAATGCACGGCACG pBG028: KPI(-4→57; M15L, S17Y)—See FIG. 14

1493 (SEQ ID NO:31): GTCCGTGCCGTGCTTTGATC-
TACCGCTGGTACTTTGACGT 1494 (SEQ ID NO:32): CAAAGTACCAGCGGTAGAT-
CAAAGCACGGCACG pTW6183: KPI(-4→57; I16H, S17F)—See FIG. 15

925 (SEQ ID NO:33): GTCCGTGCCGTGCAATG-
CACTTCCGCTGGTACTTTGACGT 926 (SEQ ID NO:34): CAAAGTACCAGCGGAAGTG-
CATTGCACGGCACG pTW6184: KPI(-4→57; I16H, S17Y)—See FIG. 16

927 (SEQ ID NO:35): GTCCGTGCCGTGCAATGCAC-
TACCGCTGGTACTTTGACGT 928 (SEQ ID NO:36): CAAAGTACCAGCGGTAGTG-
CATTGCACGGCACG pTW6185: KPI(-4→57; I16H, S17W)—See FIG. 17

929 (SEQ ID NO:37) GTCCGTGCCGTGCAATG-
CACTGGCGCTGGTACTTTGACGT 930 (SEQ ID NO:38): CAAAGTACCAGCGCCAGTG-
CATTGCACGGCACG pTW6173: KPI(-4→57; M15A, I16H)—See FIG. 18

863 (SEQ ID NO:39): GTCCGTGCCGTGCAGCT-
CACTCCCGCTGGTACTTTGACGT 864 (SEQ ID NO:40): CAAAGTACCAGCGGGAGT-
GAGCTGCACGGCACG pTW6174: KPI(-4→57; M15L, I16H)—See FIG. 19

865 (SEQ ID NO:41): GTCCGTGCCGTGCATTG-
CACTCCCGCTGGTACTTTGACGT 866 (SEQ ID NO:42): CAAAGTACCAGCGGGAGTG-
CAATGCACGGCACG

C. Transformation of Yeast with Expression Vectors

Yeast strain ABL115 was transformed by electroporation exactly according to the protocol described for transformation by pTW113.

D. Induction of Transformed Yeast Strains, Purification of KPI(-4→57) Variants.

Cultures of yeast strains were grown and induced, and recombinant secreted KPI(-4→57) variants were purified according to the procedure described for KPI(-4→57). The amino acid sequences of KPI(-4→57) variants are shown in FIGS. 20–29.

Example 3

Identification of KPI (-4→57; M15A, S17F) DD185 by Phage Display

A. Construction of Vector pSP26:Amp:F1

Figure 30:
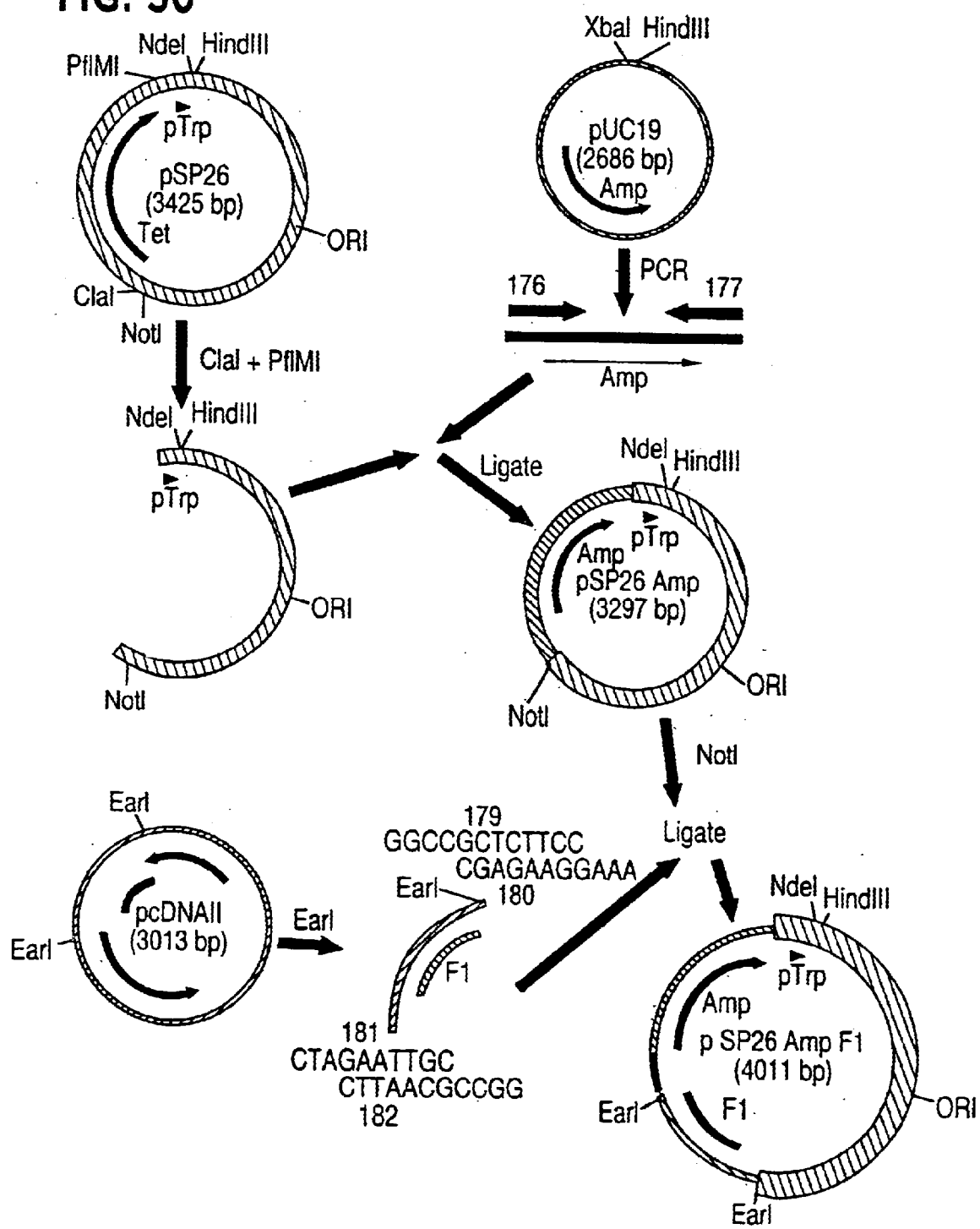
FIG. 30 (SEQ ID NOS 45–48, respectfully) shows the construction of plasmid pSP26:Amp:F1.

The construction of pSP26:Amp:F1 is outlined in FIG. 30. Vector pSP26:Amp:F1 contributes the basic plasmid backbone for the construction of the phage display vector for the phoA:KPI fusion, PDW1 #14. pSP26:Amp:F1 contains a low-copy number origin of replication, the ampicillin-resistance gene (Amp) and the F1 origin for production of single-stranded phagemid DNA.

The ampicillin-resistance gene (Amp) was generated through polymerase chain reaction (PCR) amplification from the plasmid genome of PUC19 using oligonucleotides 176 and 177.

176 (SEQ ID NO:43): GCCATCGATGGTTTCT-
TAAGCGTCAGGTGGCACTTTTC 177 (SEQ ID NO:44): GCGCCAATTCTTGGTC-
TACGGGGTCTGACGCTCAGTGGAACGAA

The PCR amplification of Amp was done according to standard techniques, using Taq polymerase (Perkin-Elmer Cetus, Norwalk, Conn.). Amplification from plasmid pUC19 with these oligonucleotides yielded a fragment of 1159 bp, containing PflMI and ClaI restriction sites. The PCR product was digested with PflMI and ClaI and purified by agarose gel electrophoresis in 3% NuSieve Agarose (FMC Corp.). Bacterial expression vector pSP26 (supra) was digested with PflMI and ClaI and the larger vector fragment was purified. The PflMI-ClaI PCR fragment was ligated into the previously digested pSP26 containing the Amp gene. The ligation product was used to transform E. coli strain MC1061 and colonies were selected by ampicillin resistance. The resulting plasmid is denoted pSP26:Amp.

The F1 origin of replication from the mammalian expression vector pcDNAII (Invitrogen) was isolated in a 692 bp EarI fragment. Plasmid pcDNAII was digested with EarI and the resulting 692 bp fragment purified by agarose gel electrophoresis. EarI-NotI adapters were added to the 692 bp EarI fragment by ligation of two annealed oligonucleotide pairs, 179+180 and 181+182. The oligo pairs were annealed as described above.

179 (SEQ ID NO:45): GGCCGCTCTTCC 180 (SEQ ID NO:46): AAAGGAAGAGC 181 (SEQ ID NO:47): CTAGAATTGC 182 (SEQ ID NO:48): GGCCGCAATTC

The oligonucleotide-ligated fragment was then ligated into the single NotI site of PSP26:Amp to yield the vector pSP26:Amp:F1.

B. Construction of Vector pgIII

Figure 31:
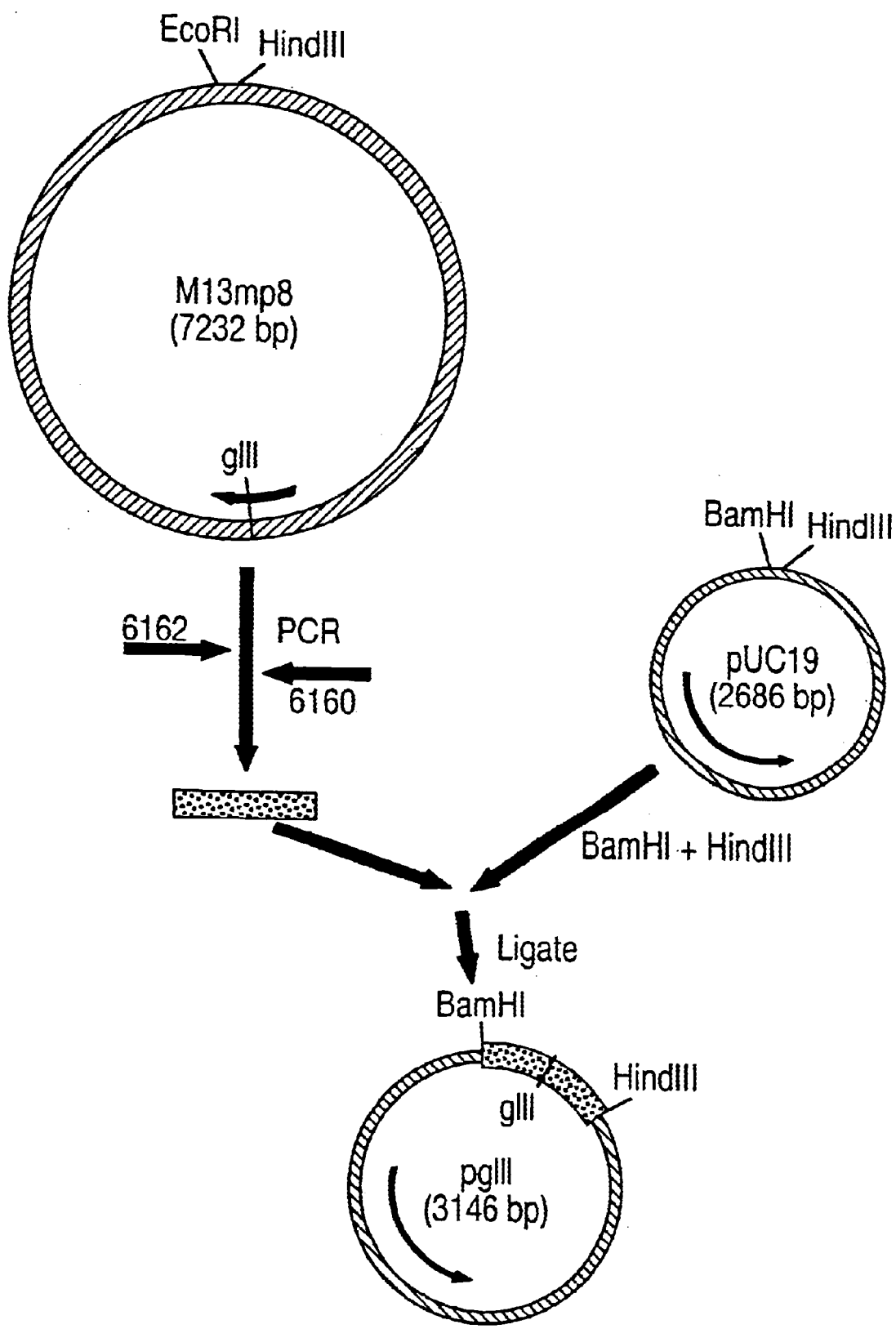
FIG. 31 shows the construction of plasmid pgIII.

The construction of pgIII is outlined in FIG. 31. The portion of the phage geneIII protein gene contained by the PDW1 #14 phagemid vector was originally obtained as a PCR amplification product from vector m13mp8. A portion of m13mp8 geneIII encoding the carboxyl-terminal 158 amino acid residues of the geneIII product was isolated by PCR amplification of m13mp8 nucleotide residues 2307–2781 using PCR oligos 6162 and 6160.

6162 (SEQ ID NO:49): GCCGGATCCGCTATTTCCG-
GTGGTGGCTCTGGTTCC 6160 (SEQ ID NO:50): GCCAAGCTTATTAAGACTC-
CTTATTACGCAG

The PCR oligos contain BamHI and HindIII restriction recognition sites such that PCR from m13mp8 plasmid DNA with the oligo pair yielded a 490 bp BamHI-HindIII fragment encoding the appropriate portion of geneIII. The PCR product was ligated between the BamHI and HindIII sites within the polylinker of PUC19 to yield plasmid pGIII.

C. Construction of pPhoA:KPI:gIII

Figure 32:
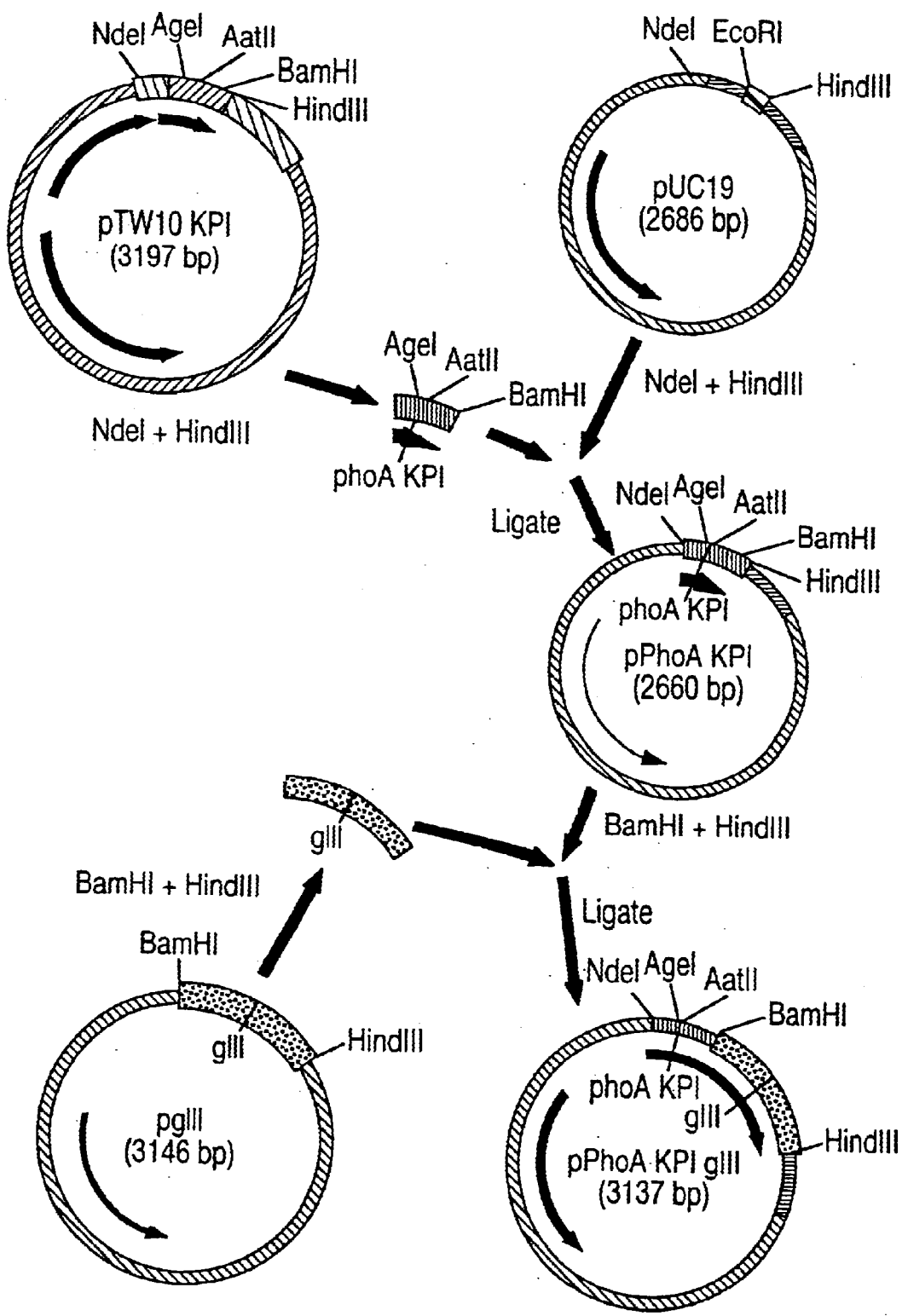
FIG. 32 shows the construction of plasmid pPhoA:KPI:gIII.

Construction of pPhoA:KPI:gIII is outlined in FIG. 32. A portion of the phoA signal sequence and KPI fusion encoded by the phage display vector PDW1 #14 originates with pPhoA:KPI:gIII. The 237 bp NdeI-HindIII fragment of pTW10:KPI encoding the entire phoA:KPI (1→57) fusion was isolated by preparative agarose gel electrophoresis, and inserted between the NdeI and HindIII sites of pUC19 to yield plasmid pPhoA:KPI. The 490 bp BamHI-HindIII fragment of pgIII encoding the C-terminal portion of the geneIII product was then isolated and ligated between the BamHI and HindIII sites of pPhoA:KPI to yield vector pPhoa:KPI:gIII. The pPhoA:KPI:gIII vector encodes a 236 amino acid residue fusion of the phoA signal peptide, KPI (1→57) and the carboxyl-terminal portion of the geneIII product.

D. Construction of pLG1

Figure 33:
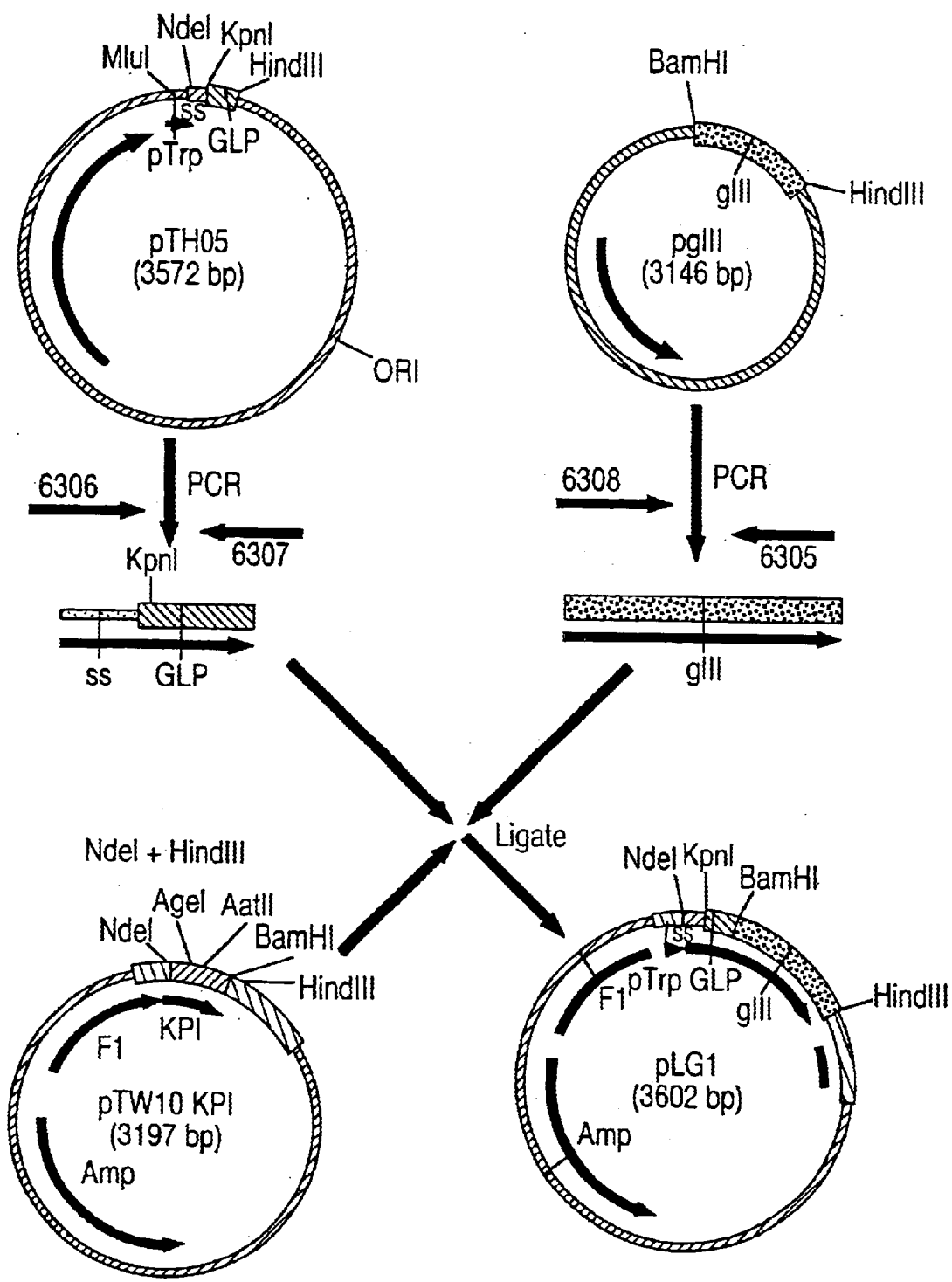
FIG. 33 shows the construction of plasmid pLG1.

Construction of pLG1 is illustrated in FIG. 33. The exact geneIII sequences contained in vector PDW1 #14 originate with phage display vector pLG1. A modified geneIII segment was generated by PCR amplification of the geneIII region from pgIII using PCR oligonucleotides 6308 and 6305.

6308 (SEQ ID NO:51): AGCTCCGATCTAGGATCCG-GTGGTGGCTCTGGTTCCGGT 6305 (SEQ ID NO:52): GCAGCGGCCGTTAAGCTTAT-TAAGACTCCT

PCR amplification from pgIII with these oligonucleotides yielded a 481 bp BamHI-HindIII fragment encoding a geneIII product shortened by 3 amino acid residues at the amino-terminal portion of the segment of the geneIII fragment encoded by pgIII. A 161 bp NdeI-BamHI fragment was generated by PCR amplification from bacterial expression plasmid pTHW05 using oligonucleotides 6306 and 6307.

6306 (SEQ ID NO:53): GATCCTTGTGTCCATAT-GAAACAAAGC 6307 (SEQ ID NO:54): CACGTCGGTCGAGGATC-CCTAACCACGGCCTTTAACCAG

The 161 bp NdeI-BamHI fragment and the 481 bp BamHI-HindIII fragment were gel-purified, and then ligated in a three-way ligation into PTW10 which had previously been digested with NdeI and HindIII. The resulting plasmid pLG1 encodes a phoA signal peptide-insert-geneIII fusion for phage display purposes.

E. Construction of pAL51

Figure 34:
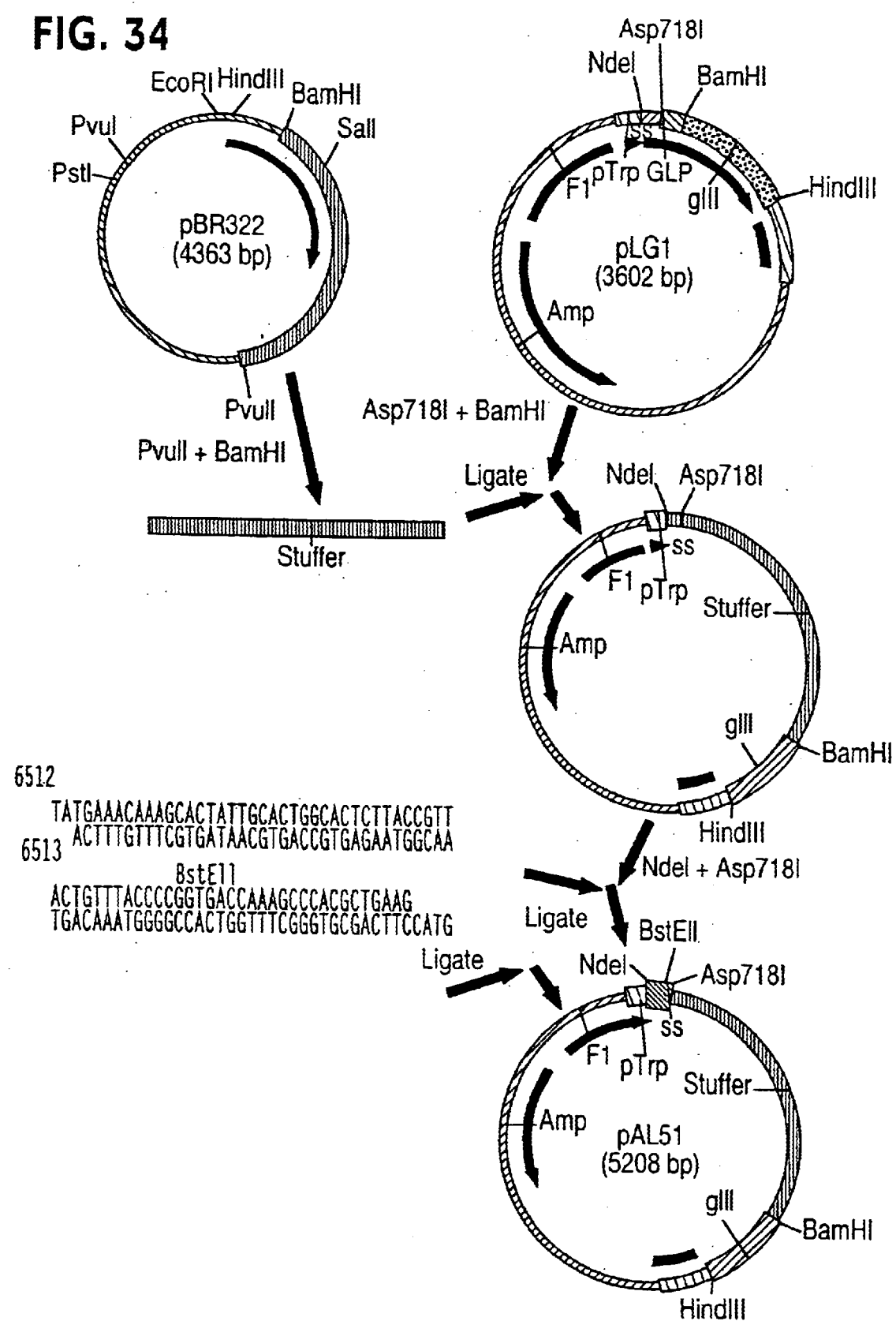
FIG. 34 (SEQ ID NOS 55 AND 56) shows the construction of plasmid pAL51.

Construction of pAL51 is illustrated in FIG. 34. Vector pAL51 contains the geneIII sequences of pLG1 which are to be incorporated in vector pDW1 #14.

A 1693 bp fragment of plasmid pBR322 was isolated, extending from the BamHI site at nucleotide 375 to the PvuII site at position 2064. Plasmid pLG1 was digested with Asp718I and BamHI, removing an 87 bp fragment. The overhanging Asp718I end was blunted by treatment with Klenow fragment, and the PvuII-BamHI fragment isolated from pBR322 was ligated into this vector, resulting in the insertion of a 1693 bp "stuffer" region between the Asp718I and BamHI sites. The 78 bp NdeI-Asp718I region of the resulting plasmid was removed and replaced with the annealed oligo pair 6512+6513.

6512 (SEQ ID NO:55): TATGAAACAAAGCACTAT-TGCACTGGCACT CTTACCGTTACTGTTTAC-CCCGGTGACCAAAGCCCACGCTGAAG 6513 (SEQ ID NO:56): GTACCTTCAGCG-TGGGCTTTGGTCACCGGG GTAAACAGT-AACGGTAAGAGTGCCAGTGCAATAGTGCTTT-GTTTCA

The newly created 74 bp NdeI-Asp718I fragment encodes the phoA signal peptide, and contains a BstEII cloning site. The resulting plasmid is denoted pAL51.

F. Construction of pAL53

Figure 35:
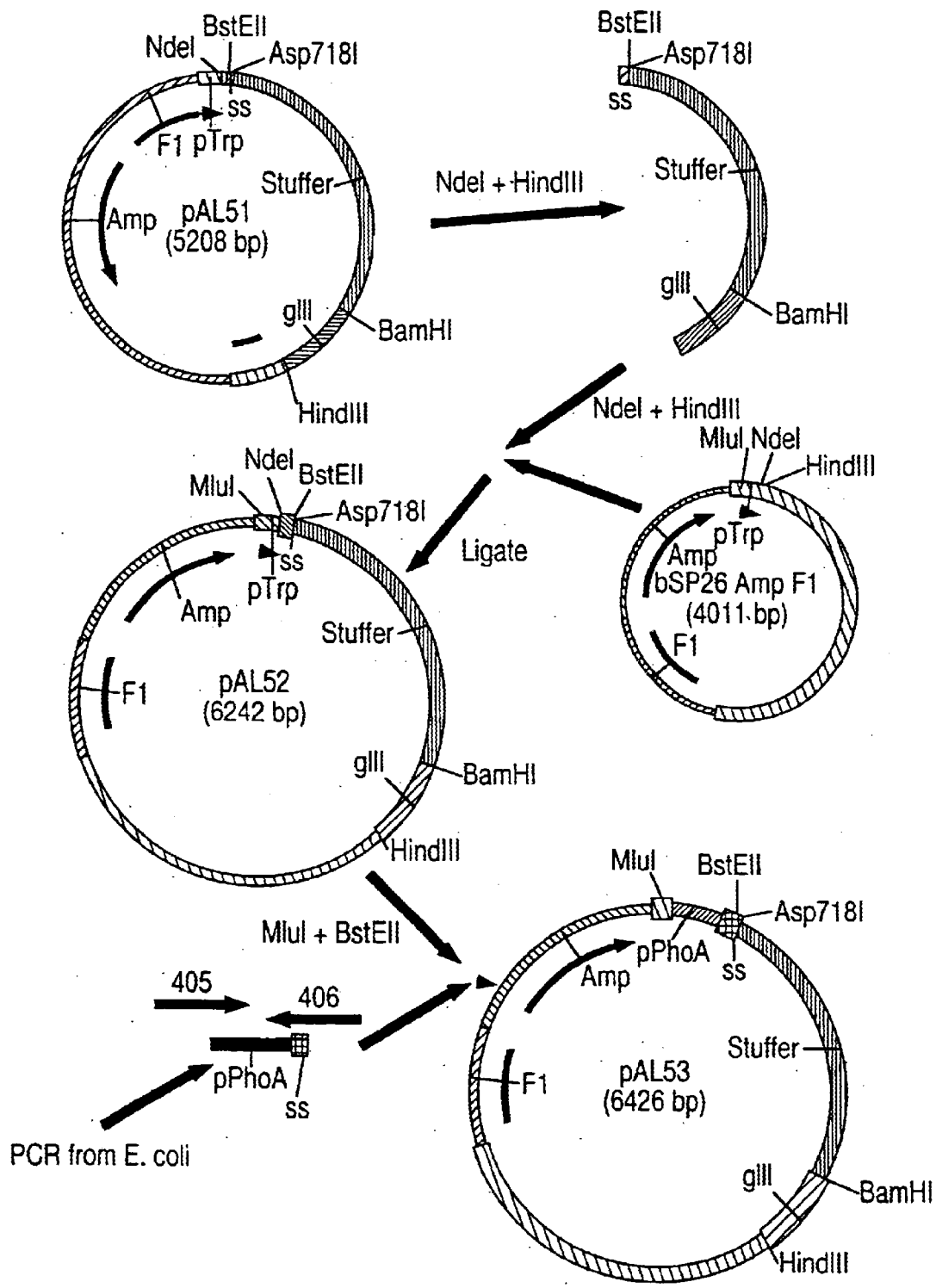
FIG. 35 shows the construction of plasmid pAL53.

Construction of pAL53 is outlined in FIG. 35. Plasmid pAL53 contributes most of the vector sequence of pDW1 #14, including the basic vector backbone with Amp gene, F1 origin, low copy number origin of replication, geneIII segment, phoA promotor and phoA signal sequence.

Plasmid pAL51 was digested with NdeI and HindIII and the resulting 2248 bp NdeI-HindIII fragment encoding the phoA signal peptide, stuffer region and geneIII region was isolated by preparative agarose gel electrophoresis. The NdeI-HindIII fragment was ligated into plasmid pSP26:Amp:F1 between the NdeI and HindIII sites, resulting in plasmid pAL52.

The phoA promoter region and signal peptide was generated by amplification of a portion of the *E. coli* genome by PCR, using oligonucleotide primers 405 and 406.

405 (SEQ ID NO:57): CCGGACGCGTGGAGAT-TATCGTCACTG 406 (SEQ ID NO:58): GCTTTGGTCACCGGGGTAAA-CAGTAACGG

The resulting PCR product is a 332 bp MluI-BstEII fragment which contains the phoA promoter region and signal peptide sequence. This fragment was used to replace the 148 bp MluI-BstEII segment of PAL52, resulting in vector pAL53.

G. Construction of pSP26:Amp:F1:PhoA:KPI:gIII

Figure 36:
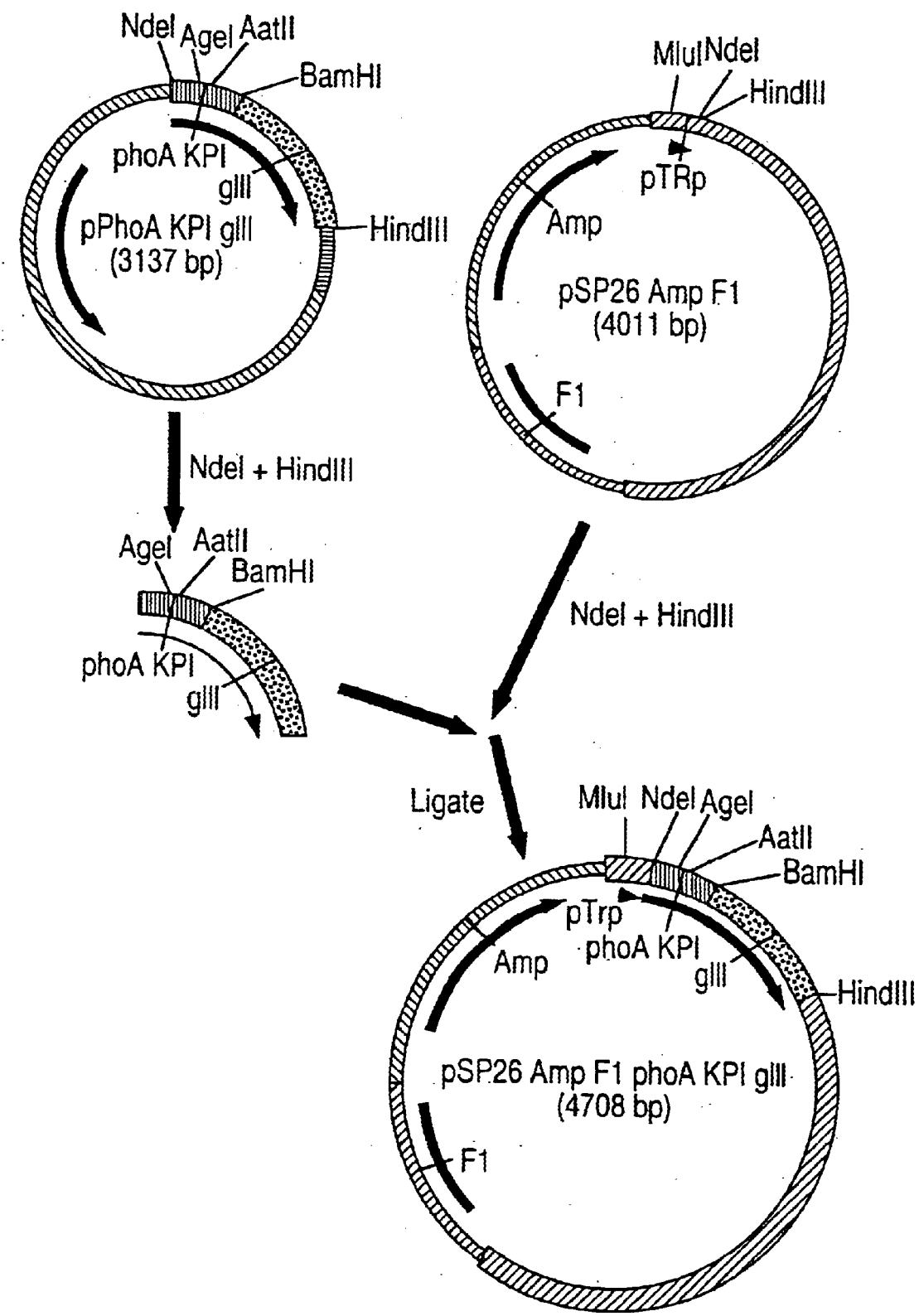
FIG. 36 shows the construction of plasmid PSP26:Amp:F1:PhoA:KPI:gIII.

Construction of pSP26:Amp:F1:PhoA:KPI:gIII is illustrated in FIG. 36. This particular vector is the source of the KPI coding sequence found in vector pDW1 #14. Plasmid pPhoa:KPI:gIII was digested with NdeI and HindIII, and the resulting 714 bp NdeI-HindIII fragment was purified, and then inserted into vector pSP26:Amp:F1 between the NdeI and HindIII sites. The resulting plasmid is denoted pSP26:Amp:F1:PhoA:KPI:gIII.

H. Construction of pDW1 #14

Figure 37:
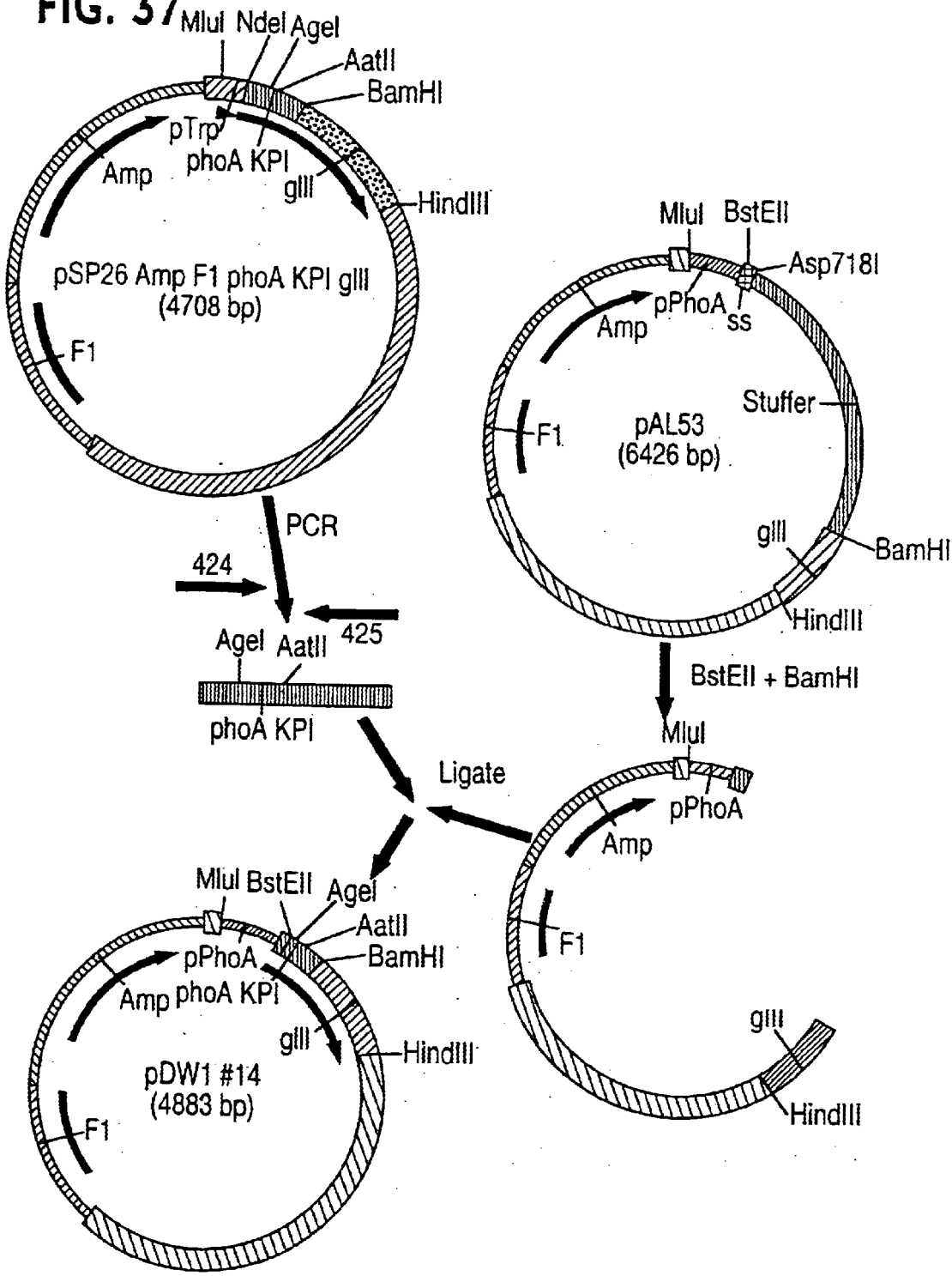
FIG. 37 shows the construction of plasmid pDW1 #14.

Construction of pDW1 #14 is illustrated in FIG. 37. The sequences encoding KPI were amplified from plasmid pSP26:Amp:F1:PhoA:KPI:gIII by PCR, using oligonucleotide primers 424 and 425.

424 (SEQ ID NO:54): CTGTTTACCCCGGTGAC-CAAAGCCGAGGTGTGCTCTGAACAA 425 (SEQ ID NO:55): AATAGCGGATCCGCACACT-GCCATGCAGTACTCTTC

The resulting 172 bp BstEII-BamHI fragment encodes most of KPI (1→55). This fragment was used to replace the stuffer region in pAL53 between the BstEII and BamHI sites. The resulting plasmid, PDW1 #14, is the parent KPI phage display vector for preparation of randomized KPI phage libraries. The coding region for the phoA-KPI (1→55)-geneIII fusion is shown in FIG. 38.

I. Construction of PDW1 14-2

Figure 39:
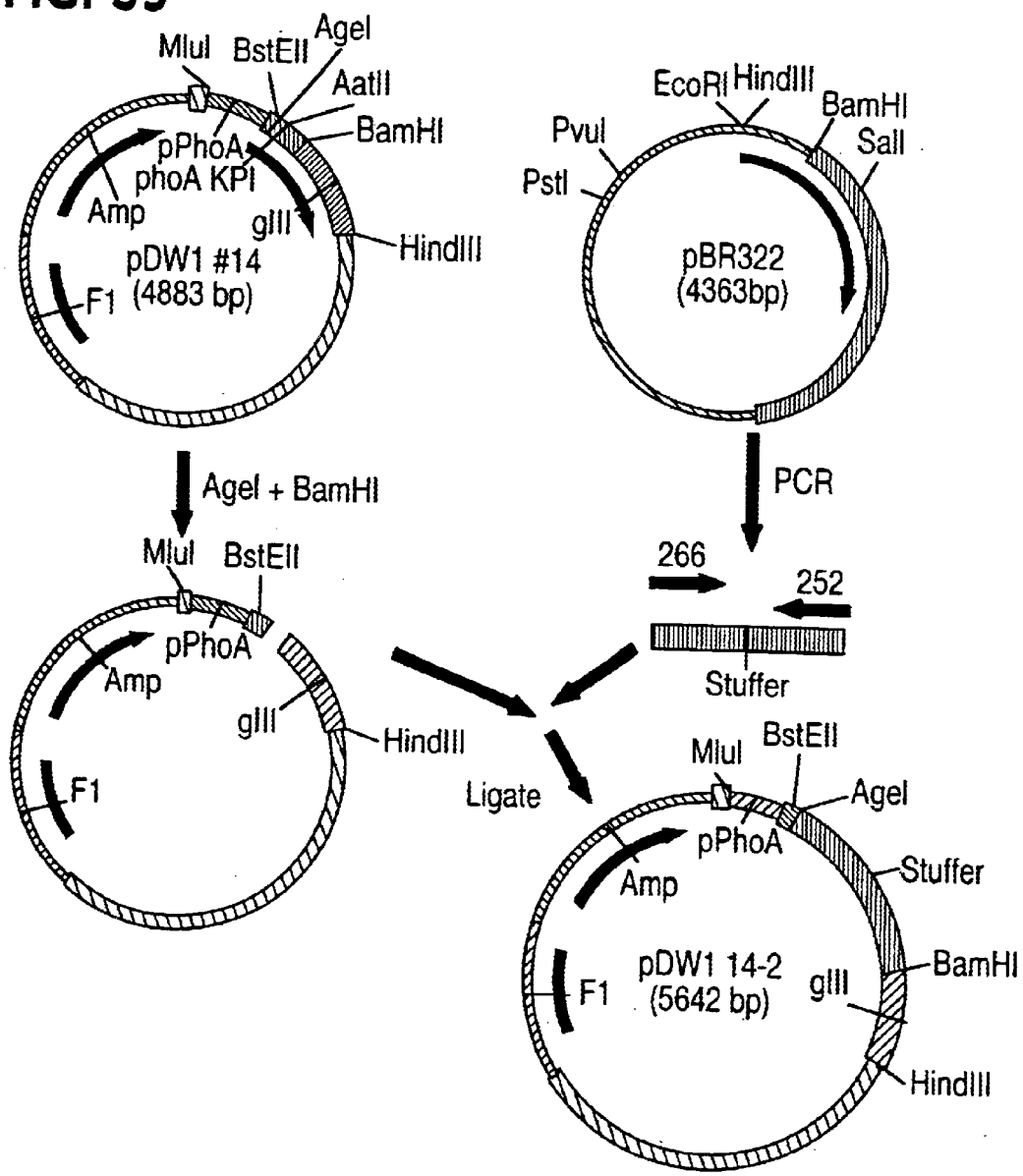
FIG. 39 shows the construction of plasmid PDW1 14-2.

Construction of pDW1 14-2 is illustrated in FIG. 39. The first step in the construction of the KPI phage libraries in pDW1 #14 was the replacement of the AgeI-BamHI fragment within the KPI coding sequence with a stuffer fragment. This greatly aids in preparation of randomized KPI libraries which are substantially free of contamination of phagemid genomes encoding wild-type KPI sequence.

Plasmid pDW1 #14 was digested with AgeI and BamHI, and the 135 bp AgeI-BamHI fragment encoding KPI was discarded. A stuffer fragment was created by PCR amplification of a portion of the PBR322 Tet gene, extending from the BamHI site at nucleotide 375 to nucleotide 1284, using oligo primers 266 and 252.

266 (SEQ ID NO:61): GCTTTAAACCGGTAGGTGGC-CCGGCTCCATGCACC 252 (SEQ ID NO:62): CGAATTCACCGGTGTCATC-CTCGGCACCGTCACCCT

The resulting 894 bp AgeI-BamHI stuffer fragment was then inserted into the AgeI/BamHI-digested pDW1 #14 to yield the phagemid vector pDW1 14-2. This vector was the starting point for construction of the randomized KPI libraries.

J. Construction of KPI Library 16–19

Figure 40:
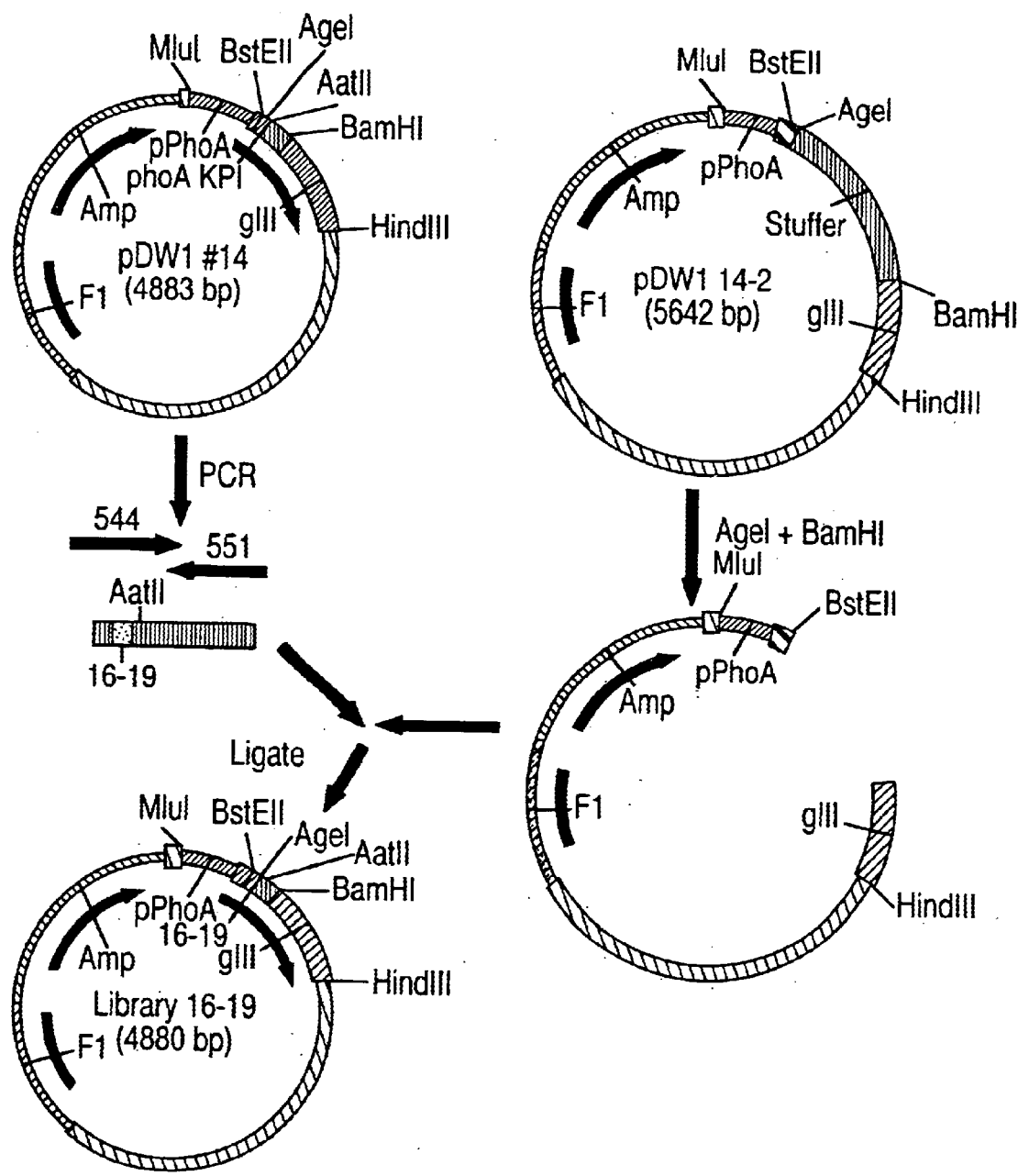
FIG. 40 shows the construction of KPI Library 16–19.

Construction of KPI Library 16–19 is outlined in FIG. 40. Library 16–19 was constructed to display KPI-geneIII fusions in which amino acid positions Ala$^{14}$, Met$^{15}$, Ile$^{16}$ and Ser$^{17}$ are randomized. For preparation of the library, plasmid pDW1 14-2 was digested with AgeI and BamHI to remove the stuffer region, and the resulting vector was purified by preparative agarose gel electrophoresis. Plasmid pDW1 #14 was used as template in a PCR amplification of the KPI region extending from the AgeI site to the BamHI site. The oligonucleotide primers used were 544 and 551.

544 (SEQ ID NO:63): GGGCTGAGACCGGTCCGT-GCCGT (NNS)$_4$CGCTGGTACTTTGACGTC 551 (SEQ ID NO:64): GGAATAGCGGATCCGCA-CACTGCCATGCAG

Oligonucleotide primer 544 contains four randomized codons of the sequence NNS, where N represents equal mixtures of A/G/C/T and S an equal mixture of G or C. Each NNS codon thus encodes all 20 amino acids plus a single possible stop codon, in 32 different DNA sequences. PCR amplification from the wild-type KPI gene resulted in the production of a mixture of 135 bp AgeI-BamHI fragments all containing different sequences in the randomized region. The PCR product was purified by preparative agarose gel electrophoresis and ligated into the AgeI/BamHI digested PDW1 14-2 vector. The ligation mixture was used to transform E. coli Top10F$^1$ cells (Invitrogen) by electroporation according to the manufacturer's directions. The resulting Library 16–19 contained approximately 400,000 independent clones. The potential size of the library, based upon the degeneracy of the priming PCR oligo #544 was 1,048,576 members. The expression unit encoded by the members of Library 16–19 is shown in FIG. 41.

K. Selection of Library 16–19 with Human Plasma Kallikrein

KPI phage were prepared and amplified by infecting transformed cells with M13KO7 helper phage as described by Matthews et al., Science 260:1113 (1993). Human plasma kallikrein (Enzyme Research Laboratories, South Bend, Ind.), was coupled to Sepharose 6B resin. Prior to phage binding, the immobilized kallikrein resin was washed three times with 0.5 ml assay buffer (AD=100 mM Tris-HCl, pH 7.5, 0.5M NaCl, 5 mM each of KCl, CaCl$_2$, MgCl$_2$, 0.1% gelatin, and 0.05% Triton X-100). Approximately 5×10$^9$ phage particles of the amplified Library 16–19 in PBS, pH 7.5, containing 300 mM NaCl and 0.1% gelatin, were bound to 50 µl kallikrein resin containing 15 pmoles of active human plasma kallikrein in a total volume of 250 µl. Phage were allowed to bind for 4 h at room temperature, with rocking. Unbound phage were removed by washing the kallikrein resin three times in 0.5 ml AB. Bound phage were eluted sequentially by successive 5 minute washes: 0.5 ml 0.5 mM sodium citrate, pH 6.0, 150mM NaCl; 0.5 ml 50 mM sodium citrate, pH 4.0, 150 mM NaCl; and 0.5 ml 50 mM glycine, pH 2.0, 150 mM NaCl. Eluted phage were neutralized immediately and phagemids from the pH 2.0 elution were titered and amplified for reselection. After three rounds of selection on kallikrein-Sepharose, phagemid DNA was isolated from 22 individual colonies and subjected to DNA sequence analysis.

The most frequently occurring randomized KPI region encoded (SEQ ID NO:65): Ala$^{14}$-Ala$^{15}$-Ile$^{16}$-Phe$^{17}$. The phoA-KPI-geneIII region encoded by this class of selected KPI phage is shown in FIG. 42. The KPI variant encoded by these phagemids is denoted KPI (1→55; M15A, S17F).

L. Construction of pDD185 KPI (-4→57; M15A, S17F)

Figure 43:
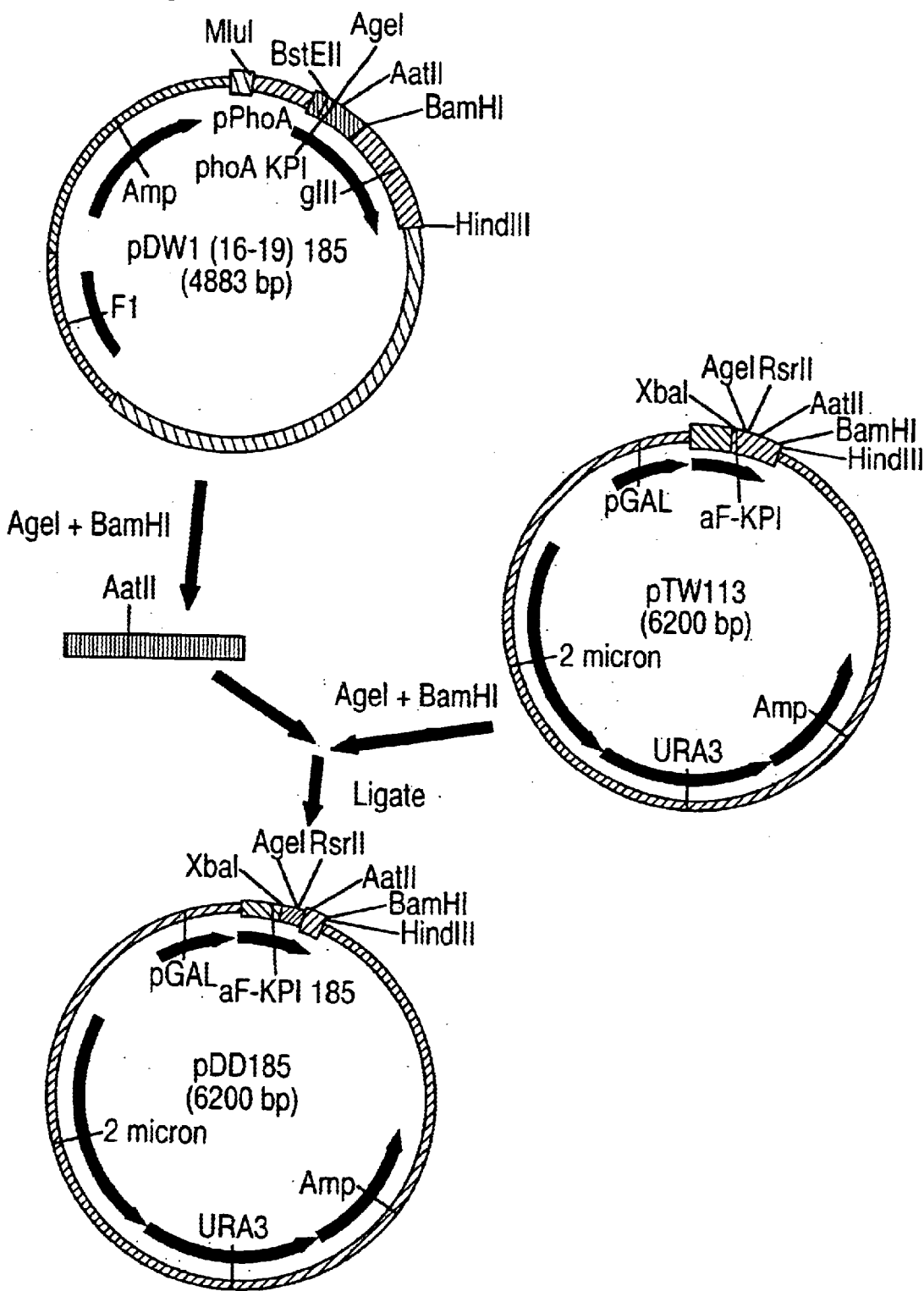
FIG. 43 shows the construction of pDD185 KPI (-4→57; M15A, S17F).
Figure 47:
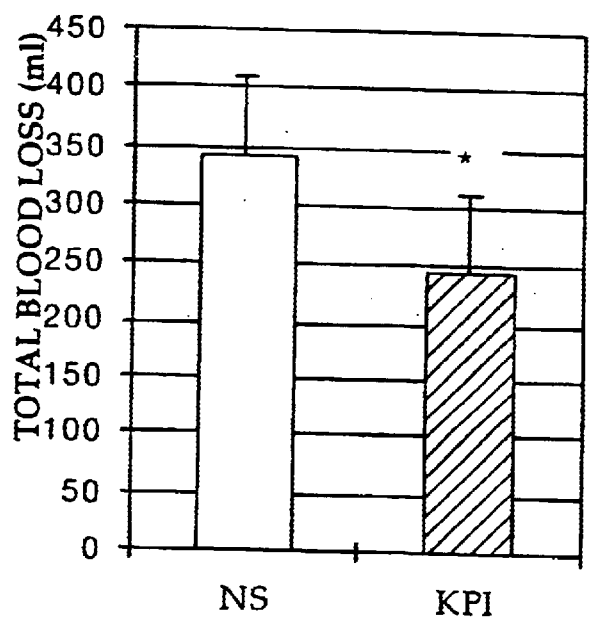
FIG. 47 shows the post-surgical blood loss in pigs in the presence (KPI) and absence (NS) of KPI 185-1 (M15A, S17F).
Figure 48:
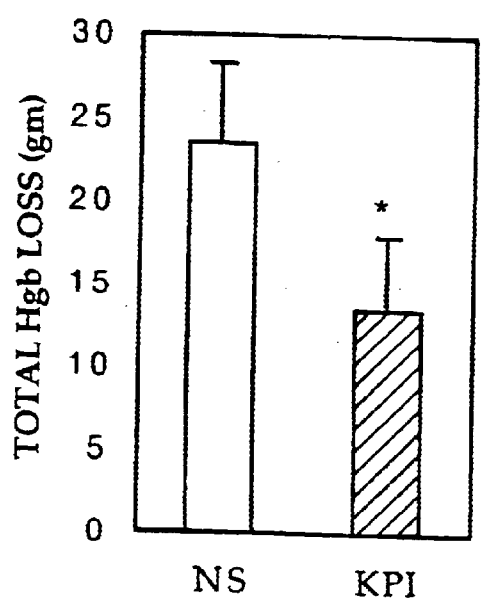
FIG. 48 shows the post-surgical hemoglobin loss in pigs in the presence (KPI) and absence (NS) of KPI 185-1 (M15A, S17F).

FIG. 43 outlines the construction of pDD185 KPI (-4→57; M15A, S17F). The sequences encoding KPI (1→55; M15A, S17F) were moved from one phagemid vector, pDW1 (16–19) 185, to the yeast expression vector so that the KPI variant could be purified and tested.

Plasmid pTW113 encoding wild-type KPI (-4→57) was digested with AgeI and BamHI and the 135 bp AgeI-BamHI fragment was discarded. The 135 bp AgeI-BamHI fragment of pDW1 (16–19) 185 was isolated and ligated into the yeast vector to yield plasmid pDD185, encoding α-factor fused to KPI (-4→57; M15A, S17F). See FIG. 44.

M. Purification of KPI (-4→57; M15A, S17F) pDD185

Transformation of yeast strain ABL115 with pDD185, induction of yeast cultures, and purification of KPI (-4→57; M15A, S17F) pDD185 was accomplished as described for the other KPI variants.

N. Construction of KPI Library 6—M15A, with Residues 14, 16–18 Random.

Library 6 was constructed to display KPI-geneIII fusions in which amino acid positions Ala$^{14}$, Ile$^{16}$, Ser$^{17}$ and Arg$^{18}$ are randomized, but position 15 was held constant as Ala. For preparation of the library, plasmid pDW1 #14 was used as template in a PCR amplification of the KPI region extending from the AgeI site to the BamHI site. The oligonucleotide primers used were 551 and 1003.

1003 (SEQ ID NO:66): GCTGAGACCGG-TCCGTGCCGTNNSGCA(NNS)$_3$TGGTACTTTGACGTC 551 (SEQ ID NO:64): GGAATAGCGGATCCGCA-CACTGCCATGCAG

Oligonucleotide primer 1003 contained four randomized codons of the sequence NNS, where N represents equal mixtures of A/G/C/T and S an equal mixture of G or C. Each NNS codon thus encodes all 20 amino acids plus a single possible stop, in 32 different DNA sequences. PCR amplification from the wild-type KPI gene resulted in the production of a mixture of 135 bp AgeI-BamHI fragments all containing different sequences in the randomized region. The PCR product was phenol extracted, ethanol precipitated, digested with BamHI and purified by preparative agarose gel electrophoresis. Plasmid pDW1 14-2 was digested with BamHI, phenol extracted and ethanol precipitated. The insert was ligated at high molar ratio to the vector which was then digested with AgeI to remove the stuffer region. The vector containing the insert was purified by agarose gel electrophoresis and recircularized. The resulting library contains approximately 5×10$^6$ independent clones.

O. Construction of KPI Library 7—Residues 14–18 Random.

Library 7 was constructed to display KPI-geneIII fusions in which amino acid positions Ala$^{14}$, Met$^{15}$, Ile$^{16}$, Ser$^{17}$ and Arg$^{18}$ are randomized. For preparation of the library, plasmid pDW1 #14 was used as template in a PCR amplification of the KPI region extending from the AgeI site to the BamHI site. The oligonucleotide primers used were 551 and 1179.

1179 (SEQ ID NO:67): GCTGAGACCGG-TCCGTGCCGT(NNS)$_5$TGGTACTTTGACGTC

551 SEQ ID NO:64): GGAATAGCGGATCCGCA-CACTGCCATGCAG

Oligonucleotide primer 1179 contains five randomized codons of the sequence NNS, where N represents equal mixtures of A/G/C/T and S an equal mixture of G or C. Each NNS codon thus encoded all 20 amino acids plus a single possible stop, in 32 different DNA sequences. PCR amplification from the wild-type KPI gene resulted in the production of a mixture of 135 bp AgeI-BamHI fragments all containing different sequences in the randomized region. The PCR product was phenol extracted, ethanol precipitated, digested with BamHI and purified by preparative agarose gel electrophoresis. Plasmid pDW1 14-2 was digested with BamHI, phenol extracted and ethanol precipitated. The insert was ligated at high molar ratio to the vector which was then digested with AgeI to remove the stuffer region. The vector containing the insert was purified by agarose gel electrophoresis and recircularized. The resulting library contains approximately 1×10$^7$ independent clones.

P. Selection of Libraries 6 & 7 with Human Factor XIIa

KPI phage were prepared and amplified by infecting transformed cells with M13K07 helper phage (Matthews and Wells, 1993). Human factor XIIa (Enzyme Research Laboratories, South Bend, Indo.), was biotinylated as follows. Factor XIIa (0.5 mg) in 5 mM sodium acetate pH 8.3 was incubated with Biotin Ester (Zymed) at room temperature for 1.5 h, then buffer-exchanged into assay buffer (AB). Approximately 1×10$^{10}$ phage particles of each amplified Library 6 or 7 in PBS, pH 7.5, containing 300 mM NaCl and 0.1% gelatin, were incubated with 50 pmoles of active biotinylated human factor XIIa in a total volume of 200 μl. Phage were allowed to bind for 2 h at room temperature, with rocking. Following the binding period, 100 μl Strepavidin Magnetic Particles (Boehringer Mannheim) were added to the mixture and incubated at room temperature for 30 minutes. Separation of magnetic particles from the supernatant and wash/elution buffers was carried out using MPC-E-1 Neodymium-iron-boron permanent magnets (Dynal). Unbound phage were removed by washing the magnetically bound biotinylated XIIa-phage complexes three times with 0.5 ml AB. Bound phage were eluted sequentially by successive 5 minute washes: 0.5 ml 50 mM sodium citrate, pH 6.0, 150 mM NaCl; 0.5 ml 50 mM sodium citrate, pH 4.0, 150 mM NaCl; and 0.5 ml 50 mM glycine, pH 2.0, 150 mM NaCl. Eluted phage were neutralized immediately and phagemids from the pH 2.0 elution were titered and amplified for reselection. After 3 or 4 rounds of selection with factor XIIa, phagemid DNA was isolated from individual colonies and subjected to DNA sequence analysis.

Sequences in the randomized regions were compared with one another to identify consensus sequences appearing more than once. From Library 6 a phagemid was identified which encoded M15L, S17Y, R18H. From Library 7 a phagemid was identified which encoded M15A, S17Y, R18H.

Q. Construction of pBG015 KPI (-4→57; M15L, S17Y, R18H), pBG022 (-4→57; M15A, S17Y, R18H)

The sequences encoding KPI (155; M15L, S17Y, R18H) and KPI (1→55; M17A, S17Y, R18H) were moved from the phagemid vectors to the yeast expression vector so that the KPI variant could be purified and tested.

Plasmid pTW113 encoding wild-type KPI (-4→57) was digested with AgeI and BamHI and the 135 bp AgeI-BamHI fragment was discarded. The 135 bp AgeI-BamHI fragment of the phagemid vectors were isolated and ligated into the yeast vector to yield plasmids pBG015 and pBG022, encoding alpha-factor fused to KPI (-4→57; M15L, S17Y, R18H), and KPI (-4→57; M15A, S17Y, R18H), respectively.

R. Construction of pBG029 KPI (-4→57, T9V, M15L, S17Y, R18H)

Plasmid pBG015 was digested with XbaI and RsrII, and the larger of the two resulting fragments was isolated. An oligonucleotide pair (1593+1642) was phosphorylated, annealed and gel-purified as described previously.

1593 (SEQ ID NO:68): CTAGATAAAAGAGAGGT-
   TGTTAGAGAGGTG TGCTCTGAACAAGCTGAG-
   GTTG 1642 (SEQ ID NO:69): GACCAACCTCAGC-
   TTGTTCAGAGCACACCTCTCTAACAACCTCTC-
   TTTTAT

The annealed oligonucleotides were ligated into the XbaI and RsrII-digested pBG015, and the ligation product was used to transform E. coli strain MC1061 to ampicillin resistance. The resulting plasmid pBG029, encodes the 445 bp synthetic gene for the alpha-factor-KPI (-4→57; T9V, M15L, S17F, R18H) fusion.

S. Construction of pBG033 KPI (-4→57; T9V, M15A, S17Y, R18H)

Plasmid pBG022 was digested with XbaI and RsrII, and the larger of the two resulting fragments was isolated. An oligonucleotide pair (1593+1642) was phosphorylated, annealed and gel-purified as described previously. The annealed oligonucleotides were ligated into the XbaI and RsrII-digested pBG022, and the ligation product was used to transform E. coli strain MC1061 to ampicillin resistance. The resulting plasmid pBG033, encodes the 445 bp synthetic gene for the alpha-factor-KPI (-4→57; T9V, M15A, S17F, R18H) fusion.

T. Selection of Library 16–19 with Human Factor Xa

KPI phage were prepared and amplified by infecting transformed cells with M13K07 helper phage (Matthews and Wells, 1993). Human factor Xa (Haematologic Technologies, Inc., Essex Junction, Vt.) was coupled to Sepharose 6B resin. Prior to phage binding, the immobilized Xa resin was washed three times with 0.5 ml assay buffer (AB=100 mM Tris-HCl, pH 7.5, 0.5M NaCl, 5 mM each of KCl, CaCl$_2$, MgCl$_2$, 0.1% gelatin, and 0.05% Triton X-100). Approximately 4×10$^{10}$ phage particles of the amplified Library 16–19 in PBS, pH 7.5, containing 300 mM NaCl and 0.1% gelatin, were bound to 50 μl Xa resin in a total volume of 250 μl. Phage were allowed to bind for 4 h at room temperature, with rocking. Unbound phage were removed by washing the Xa resin three times in 0.5 ml AB. Bound phage were eluted sequentially by successive 5 minute washes: 0.5 ml 50 mM sodium citrate, pH 6.0, 150 mM NaCl; 0.5 ml 50 mM sodium citrate, pH 4.0 150 mM NaCl; and 0.5 ml 50 mM glycine, pH 2.0, 150 mM NaCl. Eluted phage were neutralized immediately and phagemids from the pH 2.0 elution were titered and amplified for reselection. After three rounds of selection on Xa-Sepharose, phagemid DNA was isolated and subjected to DNA sequence analysis.

Sequences in the randomized Ala$^{14}$-Ser$^{17}$ region were compared with one another to identify consensus sequences appearing more than once. A phagemid was identified which encoded KPI (1→55; M15L, I16F, S17K).

U. Construction of pDD131 KPI (-4→57; M15L, I16F, S17K)

The sequences encoding KPI (1→55; M15L, I16F, S17K) were moved from the phagemid vector to the yeast expression vector so that the KPI variant could be purified and tested.

Plasmid pTW113 encoding wild-type KPI (-4→57) was digested with AgeI and BamHI and the 135 bp AgeI-BamHI fragment was discarded. The 135 bp AgeI-BamHI fragment of the phagemid vector was isolated and ligated into the yeast vector to yield plasmid pDD131, encoding alpha-factor fused to KPI (-4→57; M15L, I16F, S17K).

V. Construction of pDD134 KPI (-4→57; M15L, I16F, S17K, G37Y)

Plasmid pDD131 was digested with AatI and BamHI, and the larger of the two resulting fragments was isolated. An oligonucleotide pair (738+739) was phosphorylated, annealed and gel-purified as described previously.

738 (SEQ ID NO. 70): CACTGAAGGTAAGT-
   GCGCTCCATTCTTTTACGGCGGTTGC-
   TACGGCAA CCGTAACAACTTTGACACTGAA-
   GAGTACTGCATGGCAGTGTGCG 739 (SEQ ID NO:71): GATCCGCACACTGCC-
   ATGCAGTACTCTTCAGTGTCAAAGTTGTTAC-
   GGTTGC CGTAGCAACCGCCGTAAAAGAATG-
   GAGCGCACTTACCTTCAGTGACGT

The annealed oligonucleotides were ligated into the AatI and BamHI-digested pDD131, and the ligation product was used to transform *E. coli* strain MC1061 to ampicillin resistance. The resulting plasmid pDD134, encodes the 445 bp synthetic gene for the alpha-factor-KPI (-4→57; M15L, I16F, S17K, G37Y) fusion.

W. Construction of pDD135 KPI (-4→57; M15L, I16F, S17K, G37L)

Plasmid pDD131 was digested with AatII and BamHI, and the larger of the two resulting fragments was isolated. An oligonucleotide pair (724+725) was phosphorylated, annealed and gel-purified as described previously.

724 (SEQ ID NO:72): CACTGAAGGTAAGTGCGC-TCCATTCTTTTACGGCGGTTGCTTGGGCAACC-GTAAC AACTTTGACACTGAAGAGTACTG-CATGGCAGTGTGCG 725 (SEQ ID NO:73) GATCCGCACACTGCC-ATGCAGTACTCTTCAGTGTCAAAGTTGTTAC-GGTTGCCCA AGCAACCGCCGTAAAAGAATG-GAGCGCACTTACCTTCAGTGACGT

The annealed oligonucleotides were ligated into the AatII and BamHI-digested pDD131, and the ligation product was used to transform *E. coli* strain MC1061 to ampicillin resistance. The resulting plasmid pDD135, encodes the 445 bp synthetic gene for the alpha-factor-KPI (-4→57; M15L, I16F, S17K, G37L) fusion.

Example 4

Kinetic Analysis of KPI(-4→57) Variants

The concentrations of active human plasma kallikrein, factor XIIa, and trypsin were determined by titration with p-nitrophenyl p'-guanidinobenzoate as described by Bender et al., *supra*, and Chase et al., *Biochem. Biophys. Res. Commun.* 29:508 (1967). Accurate concentrations of active KPI (-4→57) inhibitors were determined by titration of the activity of a known amount of active-site-titrated trypsin. For testing against kallikrein and trypsin, each KPI(-4→57) variant (0.5 to 100 mM) was incubated with protease in low-binding 96-well microtiter plates at 30° C. for 15–25 min, in 100 mM Tris-HCl, pH 7.5, with 500 mM NaCl, 5 mM KCl, 5 mM CaCl2, 5 mM MgCl2, 0.1% Difco gelatin, and 0.05% Triton X-100. Chromogenic synthetic substrate was then be added, and initial rates at 30° C. recorded by the SOFTmax kinetics program via a THERMOmax microplate reader (Molecular Devices Corp., Menlo Park, Calif.). The substrates used were N-α-benzoyl-L-Arg p-nitroanilide nitroanilide (0.3 mM) for plasma kallikrein (1 nM). The Enzfitter (Elsevier) program was used both to plot fractional activity (i.e., activity with inhibitor, divided by activity without inhibitor), a, versus total concentration of inhibitor, $I_t$, and to calculate the dissociation constant of the inhibitor ($K_i$) by fitting the curve to the following equation:

$$a = 1 - \frac{[E]_t + [I]_t + K_i - \sqrt{([E]_t + [I]_t + K_i)^2 - 4[E]_t[I]_t}}{2[E]_t}$$

The $K_i$s determined for purified KPI variants are shown in FIG. 45. The most potent variant, KPI (-4→57; M15A, S17F) DD185 is 115-fold more potent as a human kallikrein inhibitor than wild-type KPI (-4→57). The least potent variant, KPI (-4→57; I16H, S17W) TW6185 is still 35-fold more potent than wild-type KPI.

For testing against factor XIIa, essentially the same reaction conditions were used, except that the substrate was N-benzoyl-Ile-Glu-Gly-Arg p-nitroaniline hydrochloride and its methyl ester (obtained from Pharmacia Hepar, Franklin, Ohio), and corn trypsin inhibitor (Enzyme Research Laboratories, South Bend, Ind.) was used as a control inhibitor. Factor XIIa was also obtained from Enzyme Research Laboratories.

Various data for inhibition of the serine proteases of interest kallikrein, plasmin, and factors Xa, XIa, and XIIa by a series of KPI variants are given in FIG. 46. The results indicate that KPI variants can be produced that can bind to and preferably inhibit the activity of serine proteases. The results also indicate that the peptides of the invention may exhibit the preferable more potent and specific inhibition of one or more serine proteases of interest.

Example 5

Effect of KPI Variant KPI185-1 on Postoperative Bleeding

A randomized, double-blinded study using an acute porcine cardiopulmonary bypass (CPB) model was used to investigate the effect of KPI185-1 on postoperative bleeding. Sixteen pigs (55–65 kg) underwent 60 minutes of hypothermic (28° C.) open-chest CPB with 30 minutes of cardioplegic cardiac arrest. Pigs were randomized against a control solution of physiological saline (NS; n=8) or KPI-185 (n=8) groups. During aortic cross-clamping, the tricuspid valve was inspected through an atriotomy which was subsequently repaired. Following reversal of heparin with protamine, dilateral thoracostomy tubes were placed and shed blood collected for 3 hours. Shed blood volume and hemoglobin (Hgb) loss were calculated from total chest tube output and residual intrathoracic blood at time of sacrifice.

Total blood loss was significantly reduced in the KPI185-1 group (245.75±66.24 ml vs. 344.25±63.97 ml, p=0.009). In addition, there was a marked reduction in total Hgb loss in the treatment group (13.59±4.26 gm vs. 23.61±4.69 gm, p=0.0005). Thoracostomy drainage Hgb was significantly increased at 30 and 60 minutes in the control group [6.89±1.44 vs. 4.41±1.45 gm/dl (p=0.004) and 7.6±1.03 vs. 5.26±1.04 gm/dl (p=0.0002), respectively]. Preoperative and post-CPB hematocrits were not statistically different between the groups. These results are shown in graphical form in FIGS. 47–50.

The invention has been disclosed broadly and illustrated in reference to representative embodiments described above. Those skilled in the art will recognize that various modifications can be made to the present invention without departing from the spirit and scope thereof.

What is claimed is:

1. An isolated DNA molecule comprising a DNA sequence encoding a polypeptide sequence selected from the group consisting of:

(DD189)
EVVREVCSEQAETGPCRAAIFRWYFD-VTEGKCAPFFYGGCGGNRNNFDTEEYC-MAVCGSAI SEQ ID NO:171);

(TW6165)
EVVREVCSEQAETGPCRAAIWRWYFD-VTEGKCAPFFYGGCGGNRNNFDTEEYC-MAVCGSAI (SEQ ID NO:172);

(TW6166)
EVVREVCSEQAETGPCRAAIYRWYFD-VTEGKCAPFFYGGCGGNRNNFDTEEYC-MAVCGSAI (SEQ ID NO:173);

(BG028)
EVVREVCSEQAETGPCRALIYRWYFD-VTEGKCAPFFYGGCGGNRNNFDTEEYC-MAVCGSAI (SEQ ID NO:174);

(TW6175)
EVVREVCSEQAETGPCRALIFRWYFD-VTEGKCAPFFYGGCGGNRNNFDTEEYC-MAVCGSAI (SEQ ID NO:177);

(DD114)
EVVREVCSEQAETGPCRAAISRWYFD-VTEGKCAPFFYGGCRGNRNNFDTEEYC-MAVCGSAI (SEQ ID NO:183);

(TW6183)
EVVREVCSEQAETGPCRAMHFRWYFD-VTEGKCAPFFYGGCGGNRNNFDTEEYC-MAVCGSAI (SEQ ID NO:185);

(TW6184)
EVVREVCSEQAETGPCRAMHYRWYFD-VTEGKCAPFFYGGCGGNRNNFDTEEYC-MAVCGSAI (SEQ ID NO:186);

(TW6185)
EVVREVCSEQAETGPCRAMHWRWYFD-VTEGKCAPFFYGGCGGNRNNFDTEEYC-MAVCGSAI (SEQ ID NO:187);

(TW61817)
EVVREVCSEQAETGPCRAMIFRWYFD-VTEGKCAPFFYGGCYGNRNNFDTEEYC-MAVCGSAI (SEQ ID NO:190);

(TW6188)
EVVREVCSEQAETGPCRAMIYRWYFD-VTEGKCAPFFYGGCYGNRNNFDTEEYC-MAVCGSAI (SEQ ID NO:191);

(BG006)
EVVREVCSEQAETGPCRAALFRWYFD-VTEGKCAPFFYGGCGGNRNNFDTEEYC-MAVCGSAI (SEQ ID NO:198);

(BG015)
EVVREVCSEQAETGPCRALIYHWYFD-VTEGKCAPFFYGGCGGNRNNFDTEEYC-MAVCGSAI (SEQ ID NO:206); and (BG020)
EVVREVCSEQAETGPCRAAIHKWYFD-VTEGKCAPFFYGGCGGNRNNFDTEEYC-MAVCGSAI (SEQ ID NO:207).

2. An isolated DNA molecule comprising a DNA sequence encoding a polypeptide sequence selected from the group consisting of:

(BG023)
EVVREVCSEQAETGPCRALIQHWYFD-VTEGKCAPFFYGGCGGNRNNFDTEEYC-MAVCGSAI (SEQ ID NO:209);

(BG029)
EVVREVCSEQAEVGPCRALIYHWYFD-VTEGKCAPFFYGGCGGNRNNFDTEEYC-MAVCGSAI (SEQ ID NO:215);

(BG030)
EVVREVCSEQAESGPCRALIYHWYFD-VTEGKCAPFFYGGCGGNRNNFDTEEYC-MAVCGSAI (SEQ ID NO:216);

(BG033)
EVVREVCSEQAEVGPCRAAIYHWYFD-VTEGKCAPFFYGGCGGNRNNFDTEEHC-MAVCGSAI (SEQ ID NO:217);

(BG034)
EVVREVCSEQAESGPCRAAIYHWYFD-VTEGKCAPFFYGGCGGNRNNFDTEEYC-MAVCGSAI (SEQ ID NO:218);

(BG040)
EVVREVCSEQAEIGPCRALIYHWYFD-VTEGKCAPFFYGGCGGNRNNFDTEEYC-MAVCGSAI (SEQ ID NO:219);

(BG016)
EVVREVCSEQAETGPCRGAIQHWYFD-VTEGKCAPFFYGGCGGNRNNFDTEEYC-MAVCGSAI (SEQ ID NO:220);

(BG017)
EVVREVCSEQAETGPCRGAIRHWYFD-VTEGKCAPFFYGGCGGNRNNFDTEEYC-MAVCGSAI (SEQ ID NO:221);

(BG021)
EVVREVCSEQAETGPCRGSIRHWYFD-VTEGKCAPFFYGGCGGNRNNFDTEEYC-MAVCGSAI (SEQ ID NO:222);

(BG025)
EVVREVCSEQAETGPCRGLIYHWYFD-VTEGKCAPFFYGGCGGNRNNFDTEEYC-MAVCGSAI (SEQ ID NO:223); and (BG026)
EVVREVCSEQAETGPCRGAIYHWYFD-VTEGKCAPFFYGGCGGNRNNFDTEEYC-MAVCGSAI (SEQ ID NO:224).

3. An isolated DNA molecule comprising a DNA sequence encoding a polypeptide sequence selected from the group consisting of:

(BG015)
EVVREVCSEQAETGPCRALIYHWYFD-VTEGKCAPFFYGGCGGNRNNFDTEEYC-MAVCGSAI (SEQ ID NO:206);

(BG022)
EVVREVCSEQAETGPCRAAIYHWYFD-VTEGKCAPFFYGGCGGNRNNFDTEEHC-MAVCGSAI (SEQ ID NO:208);

(BG027)
EVVREVCSEQAETGPCRAAIQHWYFD-VTEGKCAPFFYGGCGGNRNNFDTEEYC-MAVCGSAI (SEQ ID NO:211); and (BG029)
EVVREVCSEQAEVGPCRALIYHWYFD-VTEGKCAPFFYGGCGGNRNNFDTEEYC-MAVCGSAI (SEQ ID NO:215).

4. An isolated DNA molecule comprising a DNA sequence encoding a polypeptide sequence selected from the group consisting of:

(BG024)
EVVREVCSEQAETGPCRALIYKWYFD-VTEGKCAPFFYGGCGGNRNNFDTEEYC-MAVCGSAI (SEQ ID NO:210);

(BG023)
EVVREVCSEQAEVGPCRAAIYHWYFD-VTEGKCAPFFYGGCGGNRNNFDTEEHC-MAVCGSAI (SEQ ID NO:211);

(DD116)
EVVREVCSEQAETGPCRAAIFRWYFD-VTEGKCAPFFYGGCRGNRNNFDTEEYC-MAVCGSAI (SEQ ID NO:212);

(TW6191)
EVVREVCSEQAETGPCRAAIFRWYFD-VTEGKCAPFFYGGCYGNRNNFDTEEYC-MAVCGSAI (SEQ ID NO:213);

(DD118)
EVVREVCSEQAETGPCRALHNRWYFD-VTEGKCAPFFYGGCRGNRNNFDTEEYC-MAVCGSAI (SEQ ID NO:225);

(DD135)
EVVREVCSEQAETGPCRALFKRWYFD-VTEGKCAPFFYGGCLGNRNNFDTEEYC-MAVCGSAI (SEQ ID NO:227);

(DD136)
EVVREVCSEQAETGPCRALFKRWYFD-VTEGKCAPFFYGGCMGNRNNFDTEEYC-MAVCGSAI (SEQ ID NO:228); and (DD117)EVVREVCSEQAETGPCRALIPRWYFDV-TEGKCAPFFYGGCRGNRNNFDTEEYC-MAVCGSAI (SEQ ID NO:214).

5. An isolated DNA molecule comprising the DNA sequence encoding a polypeptide sequence of:

(TW6181)
EVVREVCSEQAETGPCRAMKSRWYFD-VTEGKCAPFFYGGCGGNRNNFDTEEYC-MAVCGSAI (SEQ ID NO:126).

6. An isolated DNA molecule comprising a DNA sequence encoding a polypeptide comprising a sequence selected from the group consisting of:

(i) Glu-Val-Val-Arg-Glu-Val-Cys-Ser-Glu-Gln-Ala-Glu-Thr-Gly-Pro-Cys-Arg-Ala-Ala-Ile-Phe-Arg-Trp-Tyr-Phe-Asp-Val-Thr-Glu-Gly-Lys-Cys-Ala-Pro-Phe-Phe-Tyr-Gly-Gly-Cys-Gly-Gly-Asn-Arg-Asn-Asn-Phe-Asp-Thr-Glu-Glu-Tyr-Cys-Met-Ala-Val-Cys-Gly-Ser-Ala-Ile (SEQ ID NO: 171);

(ii) Glu-Val-Val-Arg-Glu-Val-Cys-Ser-Glu-Gln-Ala-Glu-Thr-Gly-Pro-Cys-Arg-Ala-Ala-Ile-Tyr-His-Trp-Tyr-Phe-Asp-Val-Thr-Glu-Gly-Lys-Cys-Ala-Pro-Phe-Phe-Tyr-Gly-Gly-Cys-Gly-Gly-Asn-Arg-Asn-Asn-Phe-Asp-Thr-Glu-Glu-Tyr-Cys-Met-Ala-Val-Cys-Gly-Ser-Ala-Ile (SEQ ID. NO: 208);

(iii) Glu-Val-Val-Arg-Glu-Val-Cys-Ser-Glu-Gln-Ala-Glu-Val-Gly-Pro-Cys-Arg-Ala-Ala-Ile-Tyr-His-Trp-Tyr-Phe-Asp-Val-Thr-Glu-Gly-Lys-Cys-Ala-Pro-Phe-Phe-Tyr-Gly-Gly-Cys-Gly-Gly-Asn-Arg-Asn-Asn-Phe-Asp-Thr-Glu-Glu-Tyr-Cys-Met-Ala-Val-Cys-Gly-Ser-Ala-Ile (SEQ ID. NO: 217); and (iv) Glu-Val-Val-Arg-Glu-Val-Cys-Ser-Glu-Gln-Ala-Glu-Thr-Gly-Pro-Cys-Arg-Ala-Leu-Phe-Lys-Arg-Trp-Tyr-Phe-Asp-Val-Thr-Glu-Gly-Lys-Cys-Ala-Pro-Phe-Phe-Tyr-Gly-Gly-Cys-Leu-Gly-Asn-Arg-Asn-Asn-Phe-Asp-Thr-Glu-Glu-Tyr-Cys-Met-Ala-Val-Cys-Gly-Ser-Ala-Ile (SEQ ID. NO: 227).

7. An isolated DNA molecule according to claim 6, wherein said polypeptide comprises the sequence:

Glu-Val-Val-Arg-Glu-Val-Cys-Ser-Glu-Gln-Ala-Glu-Thr-Gly-Pro-Cys-Arg-Ala-Ala-Ile-Phe-Arg-Trp-Tyr-Phe-Asp-Val-Thr-Glu-Gly-Lys-Cys-Ala-Pro-Phe-Phe-Tyr-Gly-Gly-Cys-Gly-Gly-Asn-Arg-Asn-Asn-Phe-Asp-Thr-Glu-Glu-Tyr-Cys-Met-Ala-Val-Cys-Gly-Ser-Ala-Ile (SEQ ID NO: 171).

8. An isolated DNA molecule according to claim 6, wherein said polypeptide comprises the sequence:

Glu-Val-Val-Arg-Glu-Val-Cys-Ser-Glu-Gln-Ala-Glu-Thr-Gly-Pro-Cys-Arg-Ala-Ala-Ile-Tyr-His-Trp-Tyr-Phe-Asp-Val-Thr-Glu-Gly-Lys-Cys-Ala-Pro-Phe-Phe-Tyr-Gly-Gly-Cys-Gly-Gly-Asn-Arg-Asn-Asn-Phe-Asp-Thr-Glu-Glu-Tyr-Cys-Met-Ala-Val-Cys-Gly-Ser-Ala-Ile (SEQ ID NO 208).

9. An isolated DNA molecule according to claim 6, wherein said polypeptide comprises the sequence:

Glu-Val-Val-Arg-Glu-Val-Cys-Ser-Glu-Gln-Ala-Glu-Val-Gly-Pro-Cys-Arg-Ala-Ala-Ile-Tyr-His-Trp-Tyr-Phe-Asp-Val-Thr-Glu-Gly-Lys-Cys-Ala-Pro-Phe-Phe-Tyr-Gly-Gly-Cys-Gly-Gly-Asn-Arg-Asn-Asn-Phe-Asp-Thr-Glu-Glu-Tyr-Cys-Met-Ala-Val-Cys-Gly-Ser-Ala-Ile (SEQ ID NO: 217).

10. An isolated DNA molecule according to claim 6, wherein said polypeptide comprises the sequence:

Glu-Val-Val-Arg-Glu-Val-Cys-Ser-Glu-Gln-Ala-Glu-Thr-Gly-Pro-Cys-Arg-Ala-Leu-Phe-Lys-Arg-Trp-Tyr-Phe-Asp-Val-Thr-Glu-Gly-Lys-Cys-Ala-Pro-Phe-Phe-Tyr-Gly-Gly-Cys-Leu-Gly-Asn-Arg-Asn-Asn-Phe-Asp-Thr-Glu-Glu-Tyr-Cys-Met-Ala-Val-Cys-Gly-Ser-Ala-Ile (SEQ ID NO: 227).

* * * * *

SEQUENCE LISTING (1) GENERAL INFORMATION:

(iii) NUMBER OF SEQUENCES: 228

(2) INFORMATION FOR SEQ ID NO: 1:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 1:

```
Xaa Val Cys Ser Glu Gln Ala Glu Xaa Gly Xaa Cys Arg Ala Xaa Xaa
 1               5                  10                  15
Xaa Xaa Trp Tyr Phe Asp Val Thr Glu Gly Lys Cys Ala Pro Phe Xaa
                20                  25                  30
Tyr Gly Gly Cys Xaa Xaa Xaa Xaa Asn Asn Phe Asp Thr Glu Glu Tyr
            35                  40                  45
Cys Met Ala Val Cys Gly Ser Ala Ile
 50                  55
```

(2) INFORMATION FOR SEQ ID NO: 2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Glu Val Val Arg Glu
 1               5
```

(2) INFORMATION FOR SEQ ID NO: 3:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Xaa Val Cys Ser Glu Gln Ala Glu Thr Gly Pro Cys Arg Ala Xaa Xaa
 1               5                  10                  15
Xaa Arg Trp Tyr Phe Asp Val Thr Glu Gly Lys Cys Ala Pro Phe Phe
                20                  25                  30
Tyr Gly Gly Cys Xaa Gly Asn Arg Asn Asn Phe Asp Thr Glu Glu Tyr
            35                  40                  45
Cys Met Ala Val Cys Gly Ser Ala Ile
 50                  55
```

(2) INFORMATION FOR SEQ ID NO: 4:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Glu Val Val Arg Glu Val Cys Ser Glu Gln Ala Glu Thr Gly Pro Cys
1               5                   10                  15

Arg Ala Xaa Xaa Xaa Arg Trp Tyr Phe Asp Val Thr Glu Gly Lys Cys
                20                  25                  30

Ala Pro Phe Phe Tyr Gly Gly Cys Xaa Gly Asn Arg Asn Asn Phe Asp
            35                  40                  45

Thr Glu Glu Tyr Cys Met Ala Val Cys Gly Ser Ala Ile
50                  55                  60
```

(2) INFORMATION FOR SEQ ID NO: 5:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Xaa Val Cys Ser Glu Gln Ala Glu Xaa Gly Pro Cys Arg Ala Xaa Xaa
1               5                   10                  15

Xaa Xaa Trp Tyr Phe Asp Val Thr Glu Gly Lys Cys Ala Pro Phe Phe
                20                  25                  30

Tyr Gly Gly Cys Xaa Gly Asn Arg Asn Asn Phe Asp Thr Glu Glu Tyr
            35                  40                  45

Cys Met Ala Val Cys Gly Ser Ala Ile
50                  55
```

(2) INFORMATION FOR SEQ ID NO: 6:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Val Arg Glu Val Cys Ser Glu Gln Ala Glu Thr Gly Pro Cys Arg Ala
1               5                   10                  15

Met Ile Ser Arg Trp Tyr Phe Asp Val Thr Glu Gly Lys Cys Ala Pro
                20                  25                  30

Phe Phe Tyr Gly Gly Cys Gly Gly Asn Arg Asn Asn Phe Asp Thr Glu
            35                  40                  45

Glu Tyr Cys Met Ala Val Cys Gly Ser Ala Ile
50                  55
```

(2) INFORMATION FOR SEQ ID NO: 7:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Arg Pro Asp Phe Cys Leu Glu Pro Pro Tyr Thr Gly Pro Cys Lys Ala
1               5                   10                  15
```

```
Arg Ile Ile Arg Tyr Phe Tyr Asn Ala Lys Ala Gly Leu Cys Gln Thr
         20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
 50                  55
```

(2) INFORMATION FOR SEQ ID NO: 8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

```
Glu Val Val Arg
 1
```

(2) INFORMATION FOR SEQ ID NO: 9:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
TATGAAACAA AGCACTATTG CACTGGCACT CTTACCGTTA CTGTTTACCC CTGTGACAAA      60

AGCCGAGGTG TGCTCTGAA                                                   79
```

(2) INFORMATION FOR SEQ ID NO: 10:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
CTCGGCTTTT GTCACAGGGG TAAACAGTAA CGGTAAGAGT GCCAGTGCAA TAGTGCTTTG      60

TTTCATA                                                               67
```

(2) INFORMATION FOR SEQ ID NO: 11:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
CAAGCTGAGA CCGGTCCGTG CCGTGCAATG ATCTCCCGCT GGTACTTTGA CGTCACTGAA      60

GGTAAGTGCG CTCCATTCTT T                                               81
```

(2) INFORMATION FOR SEQ ID NO: 12:

```
    (i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GCACTTACCT TCAGTGACGT CAAAGTACCA GCGGGAGATC ATTGCACGGC ACGGACCGGT       60

CTCAGCTTGT TCAGAGCACA C                                               81

(2) INFORMATION FOR SEQ ID NO: 13:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

TACGGCGGTT GCGGCGGCAA CCGTAACAAC TTTGACACTG AAGAGTACTG CATGGCAGTG       60

TGCGGATCCG CTATTTAAGC T                                               81

(2) INFORMATION FOR SEQ ID NO: 14:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

AGCTTAAATA GCGGATCCGC ACACTGCCAT GCAGTACTCT TCAGTGTCAA AGTTGTTACG       60

GTTGCCGCCG CAACCGCCGT AAAAGAATGG AGC                                   93

(2) INFORMATION FOR SEQ ID NO: 15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CTAGATAAAA GAGAGGTGTG CTCTGAACAA GCTGAGA                               37

(2) INFORMATION FOR SEQ ID NO: 16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CCGGTCTCAG CTTGTTCAGA GCACACCTCT CTTTTAT                               37
```

(2) INFORMATION FOR SEQ ID NO: 17:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

CTAGATAAAA GAGAGGTTGT TAGAGAGGTG TGCTCTGAAC AAGCTGAGA           49

(2) INFORMATION FOR SEQ ID NO: 18:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

CCGGTCTCAG CTTGTTCAGA GCACACCTCT CTAACAACCT CTCTTTTAT           49

(2) INFORMATION FOR SEQ ID NO: 19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GGGGGCAGCT GTATAAACGA TTAAAA                                   26

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GGGGGTCTAG AGATACCCCT TCTTCTTTAG                               30

(2) INFORMATION FOR SEQ ID NO: 21:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

CTAGATAAAA GAGAGGCTGA GGCTCACGCT GAAGGTACTT TCACTTC             47

(2) INFORMATION FOR SEQ ID NO: 22:

(i) SEQUENCE CHARACTERISTICS:
        (A) LENGTH: 78 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

TGACGTCTCT TCTTACTTGG AAGGTCAAGC TGCTAAGGAA TTCATCGCTT GGTTGGTCAA    60

AGGTAGAGGT TAAGCTTA                                                 78

(2) INFORMATION FOR SEQ ID NO: 23:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

CTAGTAAGCT TAACCTCTAC CTTTGACCAA CCAAGCGATG AATTCCTTAG CA            52

(2) INFORMATION FOR SEQ ID NO: 24:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GCTTGACCTT CCAAGTAAGA AGAGACGTCA GAAGTGAAAG TACCTTCAGC GTGAGCCTCA    60

GCCTCTCTTT TAT                                                      73

(2) INFORMATION FOR SEQ ID NO: 25:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

GTCCGTGCCG TGCAGCTATC TGGCGCTGGT ACTTTGACGT                          40

(2) INFORMATION FOR SEQ ID NO: 26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

CAAAGTACCA GCGCCAGATA GCTGCACGGC ACG                                 33

(2) INFORMATION FOR SEQ ID NO: 27:

(i) SEQUENCE CHARACTERISTICS:
        (A) LENGTH: 40 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

GTCCGTGCCG TGCAGCTATC TACCGCTGGT ACTTTGACGT     40

(2) INFORMATION FOR SEQ ID NO: 28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

CAAAGTACCA GCGGTAGATA GCTGCACGGC ACG     33

(2) INFORMATION FOR SEQ ID NO: 29:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

GTCCGTGCCG TGCATTGATC TTCCGCTGGT ACTTTGACGT     40

(2) INFORMATION FOR SEQ ID NO: 30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

CAAAGTACCA GCGGAAGATC AATGCACGGC ACG     33

(2) INFORMATION FOR SEQ ID NO: 31:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

GTCCGTGCCG TGCTTTGATC TACCGCTGGT ACTTTGACGT     40

(2) INFORMATION FOR SEQ ID NO: 32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

CAAAGTACCA GCGGTAGATC AAAGCACGGC ACG                                      33

(2) INFORMATION FOR SEQ ID NO: 33:

(i) SEQUENCE CHARACTERISTICS:
           (A) LENGTH: 40 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 33:

GTCCGTGCCG TGCAATGCAC TTCCGCTGGT ACTTTGACGT                               40

(2) INFORMATION FOR SEQ ID NO: 34:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 34:

CAAAGTACCA GCGGAAGTGC ATTGCACGGC ACG                                      33

(2) INFORMATION FOR SEQ ID NO: 35:

(i) SEQUENCE CHARACTERISTICS:
           (A) LENGTH: 40 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 35:

GTCCGTGCCG TGCAATGCAC TACCGCTGGT ACTTTGACGT                               40

(2) INFORMATION FOR SEQ ID NO: 36:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 36:

CAAAGTACCA GCGGTAGTGC ATTGCACGGC ACG                                      33

(2) INFORMATION FOR SEQ ID NO: 37:

(i) SEQUENCE CHARACTERISTICS:
           (A) LENGTH: 40 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 37:

GTCCGTGCCG TGCAATGCAC TGGCGCTGGT ACTTTGACGT                                    40

(2) INFORMATION FOR SEQ ID NO: 38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

CAAAGTACCA GCGCCAGTGC ATTGCACGGC ACG                                           33

(2) INFORMATION FOR SEQ ID NO: 39:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

GTCCGTGCCG TGCAGCTCAC TCCCGCTGGT ACTTTGACGT                                    40

(2) INFORMATION FOR SEQ ID NO: 40:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

CAAAGTACCA GCGGGAGTGA GCTGCACGGC ACG                                           33

(2) INFORMATION FOR SEQ ID NO: 41:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

GTCCGTGCCG TGCATTGCAC TCCCGCTGGT ACTTTGACGT                                    40

(2) INFORMATION FOR SEQ ID NO: 42:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

CAAAGTACCA GCGGGAGTGC AATGCACGGC ACG                                           33

(2) INFORMATION FOR SEQ ID NO: 43:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

GCCATCGATG GTTTCTTAAG CGTCAGGTGG CACTTTTC                                38

(2) INFORMATION FOR SEQ ID NO: 44:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

GCGCCAATTC TTGGTCTACG GGGTCTGACG CTCAGTGGAA CGAA                         44

(2) INFORMATION FOR SEQ ID NO: 45:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

GGCCGCTCTT CC                                                           12

(2) INFORMATION FOR SEQ ID NO: 46:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

AAAGGAAGAG C                                                            11

(2) INFORMATION FOR SEQ ID NO: 47:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

CTAGAATTGC                                                              10

(2) INFORMATION FOR SEQ ID NO: 48:

(i) SEQUENCE CHARACTERISTICS:
        (A) LENGTH: 11 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 48:

GGCCGCAATT C                                                            11

(2) INFORMATION FOR SEQ ID NO: 49:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

GCCGGATCCG CTATTTCCGG TGGTGGCTCT GGTTCC                                  36

(2) INFORMATION FOR SEQ ID NO: 50:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

GCCAAGCTTA TTAAGACTCC TTATTACGCA G                                      31

(2) INFORMATION FOR SEQ ID NO: 51:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

AGCTCCGATC TAGGATCCGG TGGTGGCTCT GGTTCCGGT                               39

(2) INFORMATION FOR SEQ ID NO: 52:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

GCAGCGGCCG TTAAGCTTAT TAAGACTCCT                                         30

(2) INFORMATION FOR SEQ ID NO: 53:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

GATCCTTGTG TCCATATGAA ACAAAGC                                              27

(2) INFORMATION FOR SEQ ID NO: 54:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 54:

CACGTCGGTC GAGGATCCCT AACCACGGCC TTTAACCAG                                 39

(2) INFORMATION FOR SEQ ID NO: 55:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 55:

TATGAAACAA AGCACTATTG CACTGGCACT CTTACCGTTA CTGTTTACCC CGGTGACCAA          60

AGCCCACGCT GAAG                                                            74

(2) INFORMATION FOR SEQ ID NO: 56:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 56:

GTACCTTCAG CGTGGGCTTT GGTCACCGGG GTAAACAGTA ACGGTAAGAG TGCCAGTGCA          60

ATAGTGCTTT GTTTCA                                                          76

(2) INFORMATION FOR SEQ ID NO: 57:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 57:

CCGGACGCGT GGAGATTATC GTCACTG                                              27

(2) INFORMATION FOR SEQ ID NO: 58:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 58:

GCTTTGGTCA CCGGGGTAAA CAGTAACGG                    29

(2) INFORMATION FOR SEQ ID NO: 59:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

CTGTTTACCC CGGTGACCAA AGCCGAGGTG TGCTCTGAAC AA      42

(2) INFORMATION FOR SEQ ID NO: 60:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

AATAGCGGAT CCGCACACTG CCATGCAGTA CTCTTC            36

(2) INFORMATION FOR SEQ ID NO: 61:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

GCTTTAAACC GGTAGGTGGC CCGGCTCCAT GCACC             35

(2) INFORMATION FOR SEQ ID NO: 62:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

CGAATTCACC GGTGTCATCC TCGGCACCGT CACCCT            36

(2) INFORMATION FOR SEQ ID NO: 63:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

GGGCTGAGAC CGGTCCGTGC CGTNCGCTGG TACTTTGACG TC      42

(2) INFORMATION FOR SEQ ID NO: 64:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

GGAATAGCGG ATCCGCACAC TGCCATGCAG        30

(2) INFORMATION FOR SEQ ID NO: 65:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

Ala Ala Ile Phe
1

(2) INFORMATION FOR SEQ ID NO: 66:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

GCTGAGACCG GTCCGTGCCG TNGCANTGGT ACTTTGACGT C        41

(2) INFORMATION FOR SEQ ID NO: 67:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 67:

GCTGAGACCG GTCCGTGCCG TNTGGTACTT TGACGTC        37

(2) INFORMATION FOR SEQ ID NO: 68:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 68:

CTAGATAAAA GAGAGGTTGT TAGAGAGGTG TGCTCTGAAC AAGCTGAGGT TG        52

(2) INFORMATION FOR SEQ ID NO: 69:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 69:

GACCAACCTC AGCTTGTTCA GAGCACACCT CTCTAACAAC CTCTCTTTTA T         51

(2) INFORMATION FOR SEQ ID NO: 70:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

CACTGAAGGT AAGTGCGCTC CATTCTTTTA CGGCGGTTGC TACGGCAACC GTAACAACTT    60

TGACACTGAA GAGTACTGCA TGGCAGTGTG CG                                 92

(2) INFORMATION FOR SEQ ID NO: 71:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

GATCCGCACA CTGCCATGCA GTACTCTTCA GTGTCAAAGT TGTTACGGTT GCCGTAGCAA    60

CCGCCGTAAA AGAATGGAGC GCACTTACCT TCAGTGACGT                        100

(2) INFORMATION FOR SEQ ID NO: 72:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 72:

CACTGAAGGT AAGTGCGCTC CATTCTTTTA CGGCGGTTGC TTGGGCAACC GTAACAACTT    60

TGACACTGAA GAGTACTGCA TGGCAGTGTG CG                                 92

(2) INFORMATION FOR SEQ ID NO: 73:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

GATCCGCACA CTGCCATGCA GTACTCTTCA GTGTCAAAGT TGTTACGGTT GCCCAAGCAA    60

```
CCGCCGTAAA AGAATGGAGC GCACTTACCT TCAGTGACGT                    100
```

(2) INFORMATION FOR SEQ ID NO: 74:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..235

(xi) SEQUENCE DESCRIPTION: SEQ ID NO: 74:

```
T ATG AAA CAA AGC ACT ATT GCA CTG GCA CTC TTA CCG TTA CTG TTT    46
  Met Lys Gln Ser Thr Ile Ala Leu Ala Leu Leu Pro Leu Leu Phe
  1               5                  10                  15

ACC CCT GTG ACA AAA GCC GAG GTG TGC TCT GAA CAA GCT GAG ACC GGT  94
Thr Pro Val Thr Lys Ala Glu Val Cys Ser Glu Gln Ala Glu Thr Gly
                20                  25                  30

CCG TGC CGT GCA ATG ATC TCC CGC TGG TAC TTT GAC GTC ACT GAA GGT 142
Pro Cys Arg Ala Met Ile Ser Arg Trp Tyr Phe Asp Val Thr Glu Gly
            35                  40                  45

AAG TGC GCT CCA TTC TTT TAC GGC GGT TGC GGC GGC AAC CGT AAC AAC 190
Lys Cys Ala Pro Phe Phe Tyr Gly Gly Cys Gly Gly Asn Arg Asn Asn
        50                  55                  60

TTT GAC ACT GAA GAG TAC TGC ATG GCA GTG TGC GGA TCC GCT ATT     235
Phe Asp Thr Glu Glu Tyr Cys Met Ala Val Cys Gly Ser Ala Ile
    65                  70                  75

TA                                                              237
```

(2) INFORMATION FOR SEQ ID NO: 75:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO: 75:

```
Met Lys Gln Ser Thr Ile Ala Leu Ala Leu Leu Pro Leu Leu Phe Thr
1               5                  10                  15

Pro Val Thr Lys Ala Glu Val Cys Ser Glu Gln Ala Glu Thr Gly Pro
            20                  25                  30

Cys Arg Ala Met Ile Ser Arg Trp Tyr Phe Asp Val Thr Glu Gly Lys
        35                  40                  45

Cys Ala Pro Phe Phe Tyr Gly Gly Cys Gly Gly Asn Arg Asn Asn Phe
    50                  55                  60

Asp Thr Glu Glu Tyr Cys Met Ala Val Cys Gly Ser Ala Ile
65                  70                  75
```

(2) INFORMATION FOR SEQ ID NO: 76:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: DNA (genomic)

```
    (ix) FEATURE:
         (A) NAME/KEY: CDS
         (B) LOCATION: 1..183

(xi) SEQUENCE DESCRIPTION: SEQ ID NO: 76:

CTA GAT AAA AGA GAG GTG TGC TCT GAA CAA GCT GAG ACC GGT CCG TGC         48
Leu Asp Lys Arg Glu Val Cys Ser Glu Gln Ala Glu Thr Gly Pro Cys
 80                  85                  90

CGT GCA ATG ATC TCC CGC TGG TAC TTT GAC GTC ACT GAA GGT AAG TGC         96
Arg Ala Met Ile Ser Arg Trp Tyr Phe Asp Val Thr Glu Gly Lys Cys
 95                 100                 105                 110

GCT CCA TTC TTT TAC GGC GGT TGC GGC GGC AAC CGT AAC AAC TTT GAC        144
Ala Pro Phe Phe Tyr Gly Gly Cys Gly Gly Asn Arg Asn Asn Phe Asp
                115                 120                 125

ACT GAA GAG TAC TGC ATG GCA GTG TGC GGA TCC GCT ATT TA                 185
Thr Glu Glu Tyr Cys Met Ala Val Cys Gly Ser Ala Ile
                130                 135

(2) INFORMATION FOR SEQ ID NO: 77:

(i) SEQUENCE CHARACTERISTICS:
         (A) LENGTH: 61 amino acids
         (B) TYPE: amino acid
         (D) TOPOLOGY: linear (ii) MOLECULE TYPE: protein (xi) SEQUENCE DESCRIPTION: SEQ ID NO: 77:

Leu Asp Lys Arg Glu Val Cys Ser Glu Gln Ala Glu Thr Gly Pro Cys
  1               5                  10                  15

Arg Ala Met Ile Ser Arg Trp Tyr Phe Asp Val Thr Glu Gly Lys Cys
             20                  25                  30

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile
     50                  55                  60

(2) INFORMATION FOR SEQ ID NO: 78:

(i) SEQUENCE CHARACTERISTICS:
         (A) LENGTH: 197 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..195

(xi) SEQUENCE DESCRIPTION: SEQ ID NO: 78:

CTA GAT AAA AGA GAG GTT GTT AGA GAG GTG TGC TCT GAA CAA GCT GAG         48
Leu Asp Lys Arg Glu Val Val Arg Glu Val Cys Ser Glu Gln Ala Glu
                 65                  70                  75

ACC GGT CCG TGC CGT GCA ATG ATC TCC CGC TGG TAC TTT GAC GTC ACT         96
Thr Gly Pro Cys Arg Ala Met Ile Ser Arg Trp Tyr Phe Asp Val Thr
             80                  85                  90

GAA GGT AAG TGC GCT CCA TTC TTT TAC GGC GGT TGC GGC GGC AAC CGT        144
Glu Gly Lys Cys Ala Pro Phe Phe Tyr Gly Gly Cys Gly Gly Asn Arg
 95                 100                 105

AAC AAC TTT GAC ACT GAA GAG TAC TGC ATG GCA GTG TGC GGA TCC GCT        192
Asn Asn Phe Asp Thr Glu Glu Tyr Cys Met Ala Val Cys Gly Ser Ala
110                 115                 120                 125
```

```
ATT TA                                                                  197
Ile
```

(2) INFORMATION FOR SEQ ID NO: 79:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO: 79:

```
Leu Asp Lys Arg Glu Val Val Arg Glu Val Cys Ser Glu Gln Ala Glu
 1               5                  10                  15

Thr Gly Pro Cys Arg Ala Met Ile Ser Arg Trp Tyr Phe Asp Val Thr
             20                  25                  30

Glu Gly Lys Cys Ala Pro Phe Phe Tyr Gly Gly Cys Gly Gly Asn Arg
         35                  40                  45

Asn Asn Phe Asp Thr Glu Glu Tyr Cys Met Ala Val Cys Gly Ser Ala
     50                  55                  60

Ile
 65
```

(2) INFORMATION FOR SEQ ID NO: 80:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 80:

```
ATG AGA TTT CCT TCA ATT TTT ACT GCA GTT TTA TTC GCA GCA TCC TCC         48
Met Arg Phe Pro Ser Ile Phe Thr Ala Val Leu Phe Ala Ala Ser Ser
                     70                  75                  80

GCA TTA GCT GCT CCA GTC AAC ACT ACA ACA GAA GAT GAA ACG GCA CAA         96
Ala Leu Ala Ala Pro Val Asn Thr Thr Thr Glu Asp Glu Thr Ala Gln
             85                  90                  95

ATT CCG GCT GAA GCT GTC ATC GGT TAC TTA GAT TTA GAA GGG GAT TTC        144
Ile Pro Ala Glu Ala Val Ile Gly Tyr Leu Asp Leu Glu Gly Asp Phe
         100                 105                 110

GAT GTT GCT GTT TTG CCA TTT TCC AAC AGC ACA AAT AAC GGG TTA TTG        192
Asp Val Ala Val Leu Pro Phe Ser Asn Ser Thr Asn Asn Gly Leu Leu
115                 120                 125

TTT ATA AAT ACT ACT ATT GCC AGC ATT GCT GCT AAA GAA GAA GGG GTA        240
Phe Ile Asn Thr Thr Ile Ala Ser Ile Ala Ala Lys Glu Glu Gly Val
130                 135                 140                 145

TCT CTA GAT AAA AGA GAG GTT GTT AGA GAG GTG TGC TCT GAA CAA GCT        288
Ser Leu Asp Lys Arg Glu Val Val Arg Glu Val Cys Ser Glu Gln Ala
                 150                 155                 160

GAG ACC GGT CCG TGC CGT GCA ATG ATC TCC CGC TGG TAC TTT GAC GTC        336
Glu Thr Gly Pro Cys Arg Ala Met Ile Ser Arg Trp Tyr Phe Asp Val
             165                 170                 175

ACT GAA GGT AAG TGC GCT CCA TTC TTT TAC GGC GGT TGC GGC GGC AAC        384
Thr Glu Gly Lys Cys Ala Pro Phe Phe Tyr Gly Gly Cys Gly Gly Asn
         180                 185                 190
```

```
CGT AAC AAC TTT GAC ACT GAA GAG TAC TGC ATG GCA GTG TGC GGA TCC    432
Arg Asn Asn Phe Asp Thr Glu Glu Tyr Cys Met Ala Val Cys Gly Ser
    195                 200                 205

GCT ATT TAAGCTT                                                    445
Ala Ile
210
```

(2) INFORMATION FOR SEQ ID NO: 81:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 81:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                 70                  75                  80

Ser Leu Asp Lys Arg Glu Val Val Arg Glu Val Cys Ser Glu Gln Ala
                85                  90                  95

Glu Thr Gly Pro Cys Arg Ala Met Ile Ser Arg Trp Tyr Phe Asp Val
            100                 105                 110

Thr Glu Gly Lys Cys Ala Pro Phe Phe Tyr Gly Gly Cys Gly Gly Asn
        115                 120                 125

Arg Asn Asn Phe Asp Thr Glu Glu Tyr Cys Met Ala Val Cys Gly Ser
    130                 135                 140

Ala Ile
145
```

(2) INFORMATION FOR SEQ ID NO: 82:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 82:

```
ATG AGA TTT CCT TCA ATT TTT ACT GCA GTT TTA TTC GCA GCA TCC TCC    48
Met Arg Phe Pro Ser Ile Phe Thr Ala Val Leu Phe Ala Ala Ser Ser
    150                 155                 160

GCA TTA GCT GCT CCA GTC AAC ACT ACA ACA GAA GAT GAA ACG GCA CAA    96
Ala Leu Ala Ala Pro Val Asn Thr Thr Thr Glu Asp Glu Thr Ala Gln
            165                 170                 175

ATT CCG GCT GAA GCT GTC ATC GGT TAC TTA GAT TTA GAA GGG GAT TTC    144
Ile Pro Ala Glu Ala Val Ile Gly Tyr Leu Asp Leu Glu Gly Asp Phe
        180                 185                 190
```

```
GAT GTT GCT GTT TTG CCA TTT TCC AAC AGC ACA AAT AAC GGG TTA TTG      192
Asp Val Ala Val Leu Pro Phe Ser Asn Ser Thr Asn Asn Gly Leu Leu
195                 200                 205                 210

TTT ATA AAT ACT ACT ATT GCC AGC ATT GCT GCT AAA GAA GAA GGG GTA      240
Phe Ile Asn Thr Thr Ile Ala Ser Ile Ala Ala Lys Glu Glu Gly Val
            215                 220                 225

TCT CTA GAT AAA AGA GAG GTT GTT AGA GAG GTG TGC TCT GAA CAA GCT      288
Ser Leu Asp Lys Arg Glu Val Val Arg Glu Val Cys Ser Glu Gln Ala
        230                 235                 240

GAG ACC GGT CCG TGC CGT GCA GCT ATC TGG CGC TGG TAC TTT GAC GTC      336
Glu Thr Gly Pro Cys Arg Ala Ala Ile Trp Arg Trp Tyr Phe Asp Val
            245                 250                 255

ACT GAA GGT AAG TGC GCT CCA TTC TTT TAC GGC GGT TGC GGC GGC AAC      384
Thr Glu Gly Lys Cys Ala Pro Phe Phe Tyr Gly Gly Cys Gly Gly Asn
        260                 265                 270

CGT AAC AAC TTT GAC ACT GAA GAG TAC TGC ATG GCA GTG TGC GGA TCC      432
Arg Asn Asn Phe Asp Thr Glu Glu Tyr Cys Met Ala Val Cys Gly Ser
275                 280                 285                 290

GCT ATT TAAGCTT                                                      445
Ala Ile
```

(2) INFORMATION FOR SEQ ID NO: 83:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 83:

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Val Val Arg Glu Val Cys Ser Glu Gln Ala
                85                  90                  95

Glu Thr Gly Pro Cys Arg Ala Ala Ile Trp Arg Trp Tyr Phe Asp Val
            100                 105                 110

Thr Glu Gly Lys Cys Ala Pro Phe Phe Tyr Gly Gly Cys Gly Gly Asn
        115                 120                 125

Arg Asn Asn Phe Asp Thr Glu Glu Tyr Cys Met Ala Val Cys Gly Ser
    130                 135                 140

Ala Ile
145
```

(2) INFORMATION FOR SEQ ID NO: 84:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
    (A) NAME/KEY: CDS
    (B) LOCATION: 1..438

(xi) SEQUENCE DESCRIPTION: SEQ ID NO: 84:

```
ATG AGA TTT CCT TCA ATT TTT ACT GCA GTT TTA TTC GCA GCA TCC TCC      48
Met Arg Phe Pro Ser Ile Phe Thr Ala Val Leu Phe Ala Ala Ser Ser
            150                 155                 160

GCA TTA GCT GCT CCA GTC AAC ACT ACA ACA GAA GAT GAA ACG GCA CAA      96
Ala Leu Ala Ala Pro Val Asn Thr Thr Thr Glu Asp Glu Thr Ala Gln
                165                 170                 175

ATT CCG GCT GAA GCT GTC ATC GGT TAC TTA GAT TTA GAA GGG GAT TTC     144
Ile Pro Ala Glu Ala Val Ile Gly Tyr Leu Asp Leu Glu Gly Asp Phe
    180                 185                 190

GAT GTT GCT GTT TTG CCA TTT TCC AAC AGC ACA AAT AAC GGG TTA TTG     192
Asp Val Ala Val Leu Pro Phe Ser Asn Ser Thr Asn Asn Gly Leu Leu
195                 200                 205                 210

TTT ATA AAT ACT ACT ATT GCC AGC ATT GCT GCT AAA GAA GAA GGG GTA     240
Phe Ile Asn Thr Thr Ile Ala Ser Ile Ala Ala Lys Glu Glu Gly Val
                215                 220                 225

TCT CTA GAT AAA AGA GAG GTT GTT AGA GAG GTG TGC TCT GAA CAA GCT     288
Ser Leu Asp Lys Arg Glu Val Val Arg Glu Val Cys Ser Glu Gln Ala
            230                 235                 240

GAG ACC GGT CCG TGC CGT GCA GCT ATC TAC CGC TGG TAC TTT GAC GTC     336
Glu Thr Gly Pro Cys Arg Ala Ala Ile Tyr Arg Trp Tyr Phe Asp Val
                245                 250                 255

ACT GAA GGT AAG TGC GCT CCA TTC TTT TAC GGC GGT TGC GGC GGC AAC     384
Thr Glu Gly Lys Cys Ala Pro Phe Phe Tyr Gly Gly Cys Gly Gly Asn
    260                 265                 270

CGT AAC AAC TTT GAC ACT GAA GAG TAC TGC ATG GCA GTG TGC GGA TCC     432
Arg Asn Asn Phe Asp Thr Glu Glu Tyr Cys Met Ala Val Cys Gly Ser
275                 280                 285                 290

GCT ATT TAAGCTT                                                      445
Ala Ile
```

(2) INFORMATION FOR SEQ ID NO: 85:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 85:

```
Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
                 20                  25                  30

Ile Pro Ala Glu Ala Val Ile Gly Tyr Leu Asp Leu Glu Gly Asp Phe
         35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Asp Lys Arg Glu Val Val Arg Glu Val Cys Ser Glu Gln Ala
                 85                  90                  95

Glu Thr Gly Pro Cys Arg Ala Ala Ile Tyr Arg Trp Tyr Phe Asp Val
            100                 105                 110
```

```
Thr Glu Gly Lys Cys Ala Pro Phe Phe Tyr Gly Gly Cys Gly Gly Asn
        115                 120                 125

Arg Asn Asn Phe Asp Thr Glu Glu Tyr Cys Met Ala Val Cys Gly Ser
    130                 135                 140

Ala Ile
145
```

(2) INFORMATION FOR SEQ ID NO: 86:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 86:

```
ATG AGA TTT CCT TCA ATT TTT ACT GCA GTT TTA TTC GCA GCA TCC TCC      48
Met Arg Phe Pro Ser Ile Phe Thr Ala Val Leu Phe Ala Ala Ser Ser
        150                 155                 160

GCA TTA GCT GCT CCA GTC AAC ACT ACA ACA GAA GAT GAA ACG GCA CAA      96
Ala Leu Ala Ala Pro Val Asn Thr Thr Thr Glu Asp Glu Thr Ala Gln
        165                 170                 175

ATT CCG GCT GAA GCT GTC ATC GGT TAC TTA GAT TTA GAA GGG GAT TTC     144
Ile Pro Ala Glu Ala Val Ile Gly Tyr Leu Asp Leu Glu Gly Asp Phe
        180                 185                 190

GAT GTT GCT GTT TTG CCA TTT TCC AAC AGC ACA AAT AAC GGG TTA TTG     192
Asp Val Ala Val Leu Pro Phe Ser Asn Ser Thr Asn Asn Gly Leu Leu
195                 200                 205                 210

TTT ATA AAT ACT ACT ATT GCC AGC ATT GCT GCT AAA GAA GAA GGG GTA     240
Phe Ile Asn Thr Thr Ile Ala Ser Ile Ala Ala Lys Glu Glu Gly Val
            215                 220                 225

TCT CTA GAT AAA AGA GAG GTT GTT AGA GAG GTG TGC TCT GAA CAA GCT     288
Ser Leu Asp Lys Arg Glu Val Val Arg Glu Val Cys Ser Glu Gln Ala
        230                 235                 240

GAG ACC GGT CCG TGC CGT GCA TTG ATC TTC CGC TGG TAC TTT GAC GTC     336
Glu Thr Gly Pro Cys Arg Ala Leu Ile Phe Arg Trp Tyr Phe Asp Val
        245                 250                 255

ACT GAA GGT AAG TGC GCT CCA TTC TTT TAC GGC GGT TGC GGC GGC AAC     384
Thr Glu Gly Lys Cys Ala Pro Phe Phe Tyr Gly Gly Cys Gly Gly Asn
        260                 265                 270

CGT AAC AAC TTT GAC ACT GAA GAG TAC TGC ATG GCA GTG TGC GGA TCC     432
Arg Asn Asn Phe Asp Thr Glu Glu Tyr Cys Met Ala Val Cys Gly Ser
275                 280                 285                 290

GCT ATT TAAGCTT                                                     445
Ala Ile
```

(2) INFORMATION FOR SEQ ID NO: 87:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 87:

```
Met Arg Phe Pro Ser Ile Phe Thr Ala Val Leu Phe Ala Ala Ser Ser
  1               5                  10                  15
```

```
Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Val Val Arg Glu Val Cys Ser Glu Gln Ala
            85                  90                  95

Glu Thr Gly Pro Cys Arg Ala Leu Ile Phe Arg Trp Tyr Phe Asp Val
            100                 105                 110

Thr Glu Gly Lys Cys Ala Pro Phe Phe Tyr Gly Gly Cys Gly Gly Asn
            115                 120                 125

Arg Asn Asn Phe Asp Thr Glu Glu Tyr Cys Met Ala Val Cys Gly Ser
    130                 135                 140

Ala Ile
145

(2) INFORMATION FOR SEQ ID NO: 88:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 88:

ATG AGA TTT CCT TCA ATT TTT ACT GCA GTT TTA TTC GCA GCA TCC TCC      48
Met Arg Phe Pro Ser Ile Phe Thr Ala Val Leu Phe Ala Ala Ser Ser
            150                 155                 160

GCA TTA GCT GCT CCA GTC AAC ACT ACA ACA GAA GAT GAA ACG GCA CAA      96
Ala Leu Ala Ala Pro Val Asn Thr Thr Thr Glu Asp Glu Thr Ala Gln
            165                 170                 175

ATT CCG GCT GAA GCT GTC ATC GGT TAC TTA GAT TTA GAA GGG GAT TTC     144
Ile Pro Ala Glu Ala Val Ile Gly Tyr Leu Asp Leu Glu Gly Asp Phe
        180                 185                 190

GAT GTT GCT GTT TTG CCA TTT TCC AAC AGC ACA AAT AAC GGG TTA TTG     192
Asp Val Ala Val Leu Pro Phe Ser Asn Ser Thr Asn Asn Gly Leu Leu
195                 200                 205                 210

TTT ATA AAT ACT ACT ATT GCC AGC ATT GCT GCT AAA GAA GAA GGG GTA     240
Phe Ile Asn Thr Thr Ile Ala Ser Ile Ala Ala Lys Glu Glu Gly Val
            215                 220                 225

TCT CTA GAT AAA AGA GAG GTT GTT AGA GAG GTG TGC TCT GAA CAA GCT     288
Ser Leu Asp Lys Arg Glu Val Val Arg Glu Val Cys Ser Glu Gln Ala
            230                 235                 240

GAG ACC GGT CCG TGC CGT GCA TTG ATC TAC CGC TGG TAC TTT GAC GTC     336
Glu Thr Gly Pro Cys Arg Ala Leu Ile Tyr Arg Trp Tyr Phe Asp Val
            245                 250                 255

ACT GAA GGT AAG TGC GCT CCA TTC TTT TAC GGC GGT TGC GGC GGC AAC     384
Thr Glu Gly Lys Cys Ala Pro Phe Phe Tyr Gly Gly Cys Gly Gly Asn
            260                 265                 270

CGT AAC AAC TTT GAC ACT GAA GAG TAC TGC ATG GCA GTG TGC GGA TCC     432
Arg Asn Asn Phe Asp Thr Glu Glu Tyr Cys Met Ala Val Cys Gly Ser
```

|  | 275 |  |  | 280 |  |  | 285 |  |  | 290 |  |  |  |
|---|---|---|---|---|---|---|---|---|---|---|---|---|---|
| GCT | ATT | TAAGCTT |  |  |  |  |  |  |  |  |  |  | 445 |
| Ala | Ile |  |  |  |  |  |  |  |  |  |  |  |  |

(2) INFORMATION FOR SEQ ID NO: 89:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 89:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Val Val Arg Glu Val Cys Ser Glu Gln Ala
                85                  90                  95

Glu Thr Gly Pro Cys Arg Ala Leu Ile Tyr Arg Trp Tyr Phe Asp Val
            100                 105                 110

Thr Glu Gly Lys Cys Ala Pro Phe Phe Tyr Gly Gly Cys Gly Gly Asn
        115                 120                 125

Arg Asn Asn Phe Asp Thr Glu Glu Tyr Cys Met Ala Val Cys Gly Ser
    130                 135                 140

Ala Ile
145
```

(2) INFORMATION FOR SEQ ID NO: 90:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 90:

| ATG | AGA | TTT | CCT | TCA | ATT | TTT | ACT | GCA | GTT | TTA | TTC | GCA | GCA | TCC | TCC | 48 |
|---|---|---|---|---|---|---|---|---|---|---|---|---|---|---|---|---|
| Met | Arg | Phe | Pro | Ser | Ile | Phe | Thr | Ala | Val | Leu | Phe | Ala | Ala | Ser | Ser |  |
|  |  |  |  | 150 |  |  |  | 155 |  |  |  | 160 |  |  |  |  |
| GCA | TTA | GCT | GCT | CCA | GTC | AAC | ACT | ACA | ACA | GAA | GAT | GAA | ACG | GCA | CAA | 96 |
| Ala | Leu | Ala | Ala | Pro | Val | Asn | Thr | Thr | Thr | Glu | Asp | Glu | Thr | Ala | Gln |  |
|  |  | 165 |  |  |  | 170 |  |  |  | 175 |  |  |  |  |  |  |
| ATT | CCG | GCT | GAA | GCT | GTC | ATC | GGT | TAC | TTA | GAT | TTA | GAA | GGG | GAT | TTC | 144 |
| Ile | Pro | Ala | Glu | Ala | Val | Ile | Gly | Tyr | Leu | Asp | Leu | Glu | Gly | Asp | Phe |  |
|  | 180 |  |  |  | 185 |  |  |  | 190 |  |  |  |  |  |  |  |
| GAT | GTT | GCT | GTT | TTG | CCA | TTT | TCC | AAC | AGC | ACA | AAT | AAC | GGG | TTA | TTG | 192 |
| Asp | Val | Ala | Val | Leu | Pro | Phe | Ser | Asn | Ser | Thr | Asn | Asn | Gly | Leu | Leu |  |
| 195 |  |  |  | 200 |  |  |  | 205 |  |  |  | 210 |  |  |  |  |

```
TTT ATA AAT ACT ACT ATT GCC AGC ATT GCT GCT AAA GAA GAA GGG GTA        240
Phe Ile Asn Thr Thr Ile Ala Ser Ile Ala Ala Lys Glu Glu Gly Val
            215                 220                 225

TCT CTA GAT AAA AGA GAG GTT GTT AGA GAG GTG TGC TCT GAA CAA GCT        288
Ser Leu Asp Lys Arg Glu Val Val Arg Glu Val Cys Ser Glu Gln Ala
            230                 235                 240

GAG ACC GGT CCG TGC CGT GCA ATG CAC TTC CGC TGG TAC TTT GAC GTC        336
Glu Thr Gly Pro Cys Arg Ala Met His Phe Arg Trp Tyr Phe Asp Val
            245                 250                 255

ACT GAA GGT AAG TGC GCT CCA TTC TTT TAC GGC GGT TGC GGC GGC AAC        384
Thr Glu Gly Lys Cys Ala Pro Phe Phe Tyr Gly Gly Cys Gly Gly Asn
260                 265                 270

CGT AAC AAC TTT GAC ACT GAA GAG TAC TGC ATG GCA GTG TGC GGA TCC        432
Arg Asn Asn Phe Asp Thr Glu Glu Tyr Cys Met Ala Val Cys Gly Ser
275                 280                 285                 290

GCT ATT TAAGCTT                                                         445
Ala Ile
```

(2) INFORMATION FOR SEQ ID NO: 91:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 91:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Leu Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Asp Lys Arg Glu Val Val Arg Glu Val Cys Ser Glu Gln Ala
                 85                  90                  95

Glu Thr Gly Pro Cys Arg Ala Met His Phe Arg Trp Tyr Phe Asp Val
            100                 105                 110

Thr Glu Gly Lys Cys Ala Pro Phe Phe Tyr Gly Gly Cys Gly Gly Asn
        115                 120                 125

Arg Asn Asn Phe Asp Thr Glu Glu Tyr Cys Met Ala Val Cys Gly Ser
    130                 135                 140

Ala Ile
145
```

(2) INFORMATION FOR SEQ ID NO: 92:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS (B) LOCATION: 1..438

(xi) SEQUENCE DESCRIPTION: SEQ ID NO: 92:

```
ATG AGA TTT CCT TCA ATT TTT ACT GCA GTT TTA TTC GCA GCA TCC TCC      48
Met Arg Phe Pro Ser Ile Phe Thr Ala Val Leu Phe Ala Ala Ser Ser
            150                 155                 160

GCA TTA GCT GCT CCA GTC AAC ACT ACA ACA GAA GAT GAA ACG GCA CAA      96
Ala Leu Ala Ala Pro Val Asn Thr Thr Thr Glu Asp Glu Thr Ala Gln
        165                 170                 175

ATT CCG GCT GAA GCT GTC ATC GGT TAC TTA GAT TTA GAA GGG GAT TTC     144
Ile Pro Ala Glu Ala Val Ile Gly Tyr Leu Asp Leu Glu Gly Asp Phe
    180                 185                 190

GAT GTT GCT GTT TTG CCA TTT TCC AAC AGC ACA AAT AAC GGG TTA TTG     192
Asp Val Ala Val Leu Pro Phe Ser Asn Ser Thr Asn Asn Gly Leu Leu
195                 200                 205                 210

TTT ATA AAT ACT ACT ATT GCC AGC ATT GCT GCT AAA GAA GAA GGG GTA     240
Phe Ile Asn Thr Thr Ile Ala Ser Ile Ala Ala Lys Glu Glu Gly Val
                215                 220                 225

TCT CTA GAT AAA AGA GAG GTT GTT AGA GAG GTG TGC TCT GAA CAA GCT     288
Ser Leu Asp Lys Arg Glu Val Val Arg Glu Val Cys Ser Glu Gln Ala
            230                 235                 240

GAG ACC GGT CCG TGC CGT GCA ATG CAC TAC CGC TGG TAC TTT GAC GTC     336
Glu Thr Gly Pro Cys Arg Ala Met His Tyr Arg Trp Tyr Phe Asp Val
        245                 250                 255

ACT GAA GGT AAG TGC GCT CCA TTC TTT TAC GGC GGT TGC GGC GGC AAC     384
Thr Glu Gly Lys Cys Ala Pro Phe Phe Tyr Gly Gly Cys Gly Gly Asn
    260                 265                 270

CGT AAC AAC TTT GAC ACT GAA GAG TAC TGC ATG GCA GTG TGC GGA TCC     432
Arg Asn Asn Phe Asp Thr Glu Glu Tyr Cys Met Ala Val Cys Gly Ser
275                 280                 285                 290

GCT ATT TAAGCTT                                                     445
Ala Ile
```

(2) INFORMATION FOR SEQ ID NO: 93:

(i) SEQUENCE CHARACTERISTICS:
       (A) LENGTH: 146 amino acids
       (B) TYPE: amino acid
       (D) TOPOLOGY: linear (ii) MOLECULE TYPE: protein (xi) SEQUENCE DESCRIPTION: SEQ ID NO: 93:

```
Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Asp Lys Arg Glu Val Val Arg Glu Val Cys Ser Glu Gln Ala
                 85                  90                  95

Glu Thr Gly Pro Cys Arg Ala Met His Tyr Arg Trp Tyr Phe Asp Val
            100                 105                 110

Thr Glu Gly Lys Cys Ala Pro Phe Phe Tyr Gly Gly Cys Gly Gly Asn
        115                 120                 125
```

```
Arg Asn Asn Phe Asp Thr Glu Glu Tyr Cys Met Ala Val Cys Gly Ser
    130                 135                 140
Ala Ile
145
```

(2) INFORMATION FOR SEQ ID NO: 94:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 94:

```
ATG AGA TTT CCT TCA ATT TTT ACT GCA GTT TTA TTC GCA GCA TCC TCC      48
Met Arg Phe Pro Ser Ile Phe Thr Ala Val Leu Phe Ala Ala Ser Ser
            150                 155                 160

GCA TTA GCT GCT CCA GTC AAC ACT ACA ACA GAA GAT GAA ACG GCA CAA      96
Ala Leu Ala Ala Pro Val Asn Thr Thr Thr Glu Asp Glu Thr Ala Gln
            165                 170                 175

ATT CCG GCT GAA GCT GTC ATC GGT TAC TTA GAT TTA GAA GGG GAT TTC     144
Ile Pro Ala Glu Ala Val Ile Gly Tyr Leu Asp Leu Glu Gly Asp Phe
            180                 185                 190

GAT GTT GCT GTT TTG CCA TTT TCC AAC AGC ACA AAT AAC GGG TTA TTG     192
Asp Val Ala Val Leu Pro Phe Ser Asn Ser Thr Asn Asn Gly Leu Leu
195                 200                 205                 210

TTT ATA AAT ACT ACT ATT GCC AGC ATT GCT GCT AAA GAA GAA GGG GTA     240
Phe Ile Asn Thr Thr Ile Ala Ser Ile Ala Ala Lys Glu Glu Gly Val
            215                 220                 225

TCT CTA GAT AAA AGA GAG GTT GTT AGA GAG GTG TGC TCT GAA CAA GCT     288
Ser Leu Asp Lys Arg Glu Val Val Arg Glu Val Cys Ser Glu Gln Ala
            230                 235                 240

GAG ACC GGT CCG TGC CGT GCA ATG CAC TGG CGC TGG TAC TTT GAC GTC     336
Glu Thr Gly Pro Cys Arg Ala Met His Trp Arg Trp Tyr Phe Asp Val
            245                 250                 255

ACT GAA GGT AAG TGC GCT CCA TTC TTT TAC GGC GGT TGC GGC GGC AAC     384
Thr Glu Gly Lys Cys Ala Pro Phe Phe Tyr Gly Gly Cys Gly Gly Asn
            260                 265                 270

CGT AAC AAC TTT GAC ACT GAA GAG TAC TGC ATG GCA GTG TGC GGA TCC     432
Arg Asn Asn Phe Asp Thr Glu Glu Tyr Cys Met Ala Val Cys Gly Ser
275                 280                 285                 290

GCT ATT TAAGCTT                                                      445
Ala Ile
```

(2) INFORMATION FOR SEQ ID NO: 95:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 95:

```
Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
             20                  25                  30
```

```
Ile Pro Ala Glu Ala Val Ile Gly Tyr Leu Asp Leu Glu Gly Asp Phe
         35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Asp Lys Arg Glu Val Val Arg Glu Val Cys Ser Glu Gln Ala
             85                  90                  95

Glu Thr Gly Pro Cys Arg Ala Met His Trp Arg Trp Tyr Phe Asp Val
             100                 105                 110

Thr Glu Gly Lys Cys Ala Pro Phe Phe Tyr Gly Gly Cys Gly Gly Asn
             115                 120                 125

Arg Asn Asn Phe Asp Thr Glu Glu Tyr Cys Met Ala Val Cys Gly Ser
 130                 135                 140

Ala Ile
145
```

(2) INFORMATION FOR SEQ ID NO: 96:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 96:

```
ATG AGA TTT CCT TCA ATT TTT ACT GCA GTT TTA TTC GCA GCA TCC TCC      48
Met Arg Phe Pro Ser Ile Phe Thr Ala Val Leu Phe Ala Ala Ser Ser
         150                 155                 160

GCA TTA GCT GCT CCA GTC AAC ACT ACA ACA GAA GAT GAA ACG GCA CAA      96
Ala Leu Ala Ala Pro Val Asn Thr Thr Thr Glu Asp Glu Thr Ala Gln
         165                 170                 175

ATT CCG GCT GAA GCT GTC ATC GGT TAC TTA GAT TTA GAA GGG GAT TTC     144
Ile Pro Ala Glu Ala Val Ile Gly Tyr Leu Asp Leu Glu Gly Asp Phe
 180                 185                 190

GAT GTT GCT GTT TTG CCA TTT TCC AAC AGC ACA AAT AAC GGG TTA TTG     192
Asp Val Ala Val Leu Pro Phe Ser Asn Ser Thr Asn Asn Gly Leu Leu
 195                 200                 205                 210

TTT ATA AAT ACT ACT ATT GCC AGC ATT GCT GCT AAA GAA GAA GGG GTA     240
Phe Ile Asn Thr Thr Ile Ala Ser Ile Ala Ala Lys Glu Glu Gly Val
             215                 220                 225

TCT CTA GAT AAA AGA GAG GTT GTT AGA GAG GTG TGC TCT GAA CAA GCT     288
Ser Leu Asp Lys Arg Glu Val Val Arg Glu Val Cys Ser Glu Gln Ala
             230                 235                 240

GAG ACC GGT CCG TGC CGT GCA GCT CAC TCC CGC TGG TAC TTT GAC GTC     336
Glu Thr Gly Pro Cys Arg Ala Ala His Ser Arg Trp Tyr Phe Asp Val
             245                 250                 255

ACT GAA GGT AAG TGC GCT CCA TTC TTT TAC GGC GGT TGC GGC GGC AAC     384
Thr Glu Gly Lys Cys Ala Pro Phe Phe Tyr Gly Gly Cys Gly Gly Asn
             260                 265                 270

CGT AAC AAC TTT GAC ACT GAA GAG TAC TGC ATG GCA GTG TGC GGA TCC     432
Arg Asn Asn Phe Asp Thr Glu Glu Tyr Cys Met Ala Val Cys Gly Ser
 275                 280                 285                 290

GCT ATT TAAGCTT                                                     445
```

Ala Ile (2) INFORMATION FOR SEQ ID NO: 97:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 97:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
 65                  70                  75                  80

Ser Leu Asp Lys Arg Glu Val Val Arg Glu Val Cys Ser Glu Gln Ala
                85                  90                  95

Glu Thr Gly Pro Cys Arg Ala Ala His Ser Arg Trp Tyr Phe Asp Val
            100                 105                 110

Thr Glu Gly Lys Cys Ala Pro Phe Phe Tyr Gly Gly Cys Gly Gly Asn
        115                 120                 125

Arg Asn Asn Phe Asp Thr Glu Glu Tyr Cys Met Ala Val Cys Gly Ser
    130                 135                 140

Ala Ile
145
```

(2) INFORMATION FOR SEQ ID NO: 98:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..438

(xi) SEQUENCE DESCRIPTION: SEQ ID NO: 98:

```
ATG AGA TTT CCT TCA ATT TTT ACT GCA GTT TTA TTC GCA GCA TCC TCC      48
Met Arg Phe Pro Ser Ile Phe Thr Ala Val Leu Phe Ala Ala Ser Ser
            150                 155                 160

GCA TTA GCT GCT CCA GTC AAC ACT ACA ACA GAA GAT GAA ACG GCA CAA      96
Ala Leu Ala Ala Pro Val Asn Thr Thr Thr Glu Asp Glu Thr Ala Gln
        165                 170                 175

ATT CCG GCT GAA GCT GTC ATC GGT TAC TTA GAT TTA GAA GGG GAT TTC     144
Ile Pro Ala Glu Ala Val Ile Gly Tyr Leu Asp Leu Glu Gly Asp Phe
    180                 185                 190

GAT GTT GCT GTT TTG CCA TTT TCC AAC AGC ACA AAT AAC GGG TTA TTG     192
Asp Val Ala Val Leu Pro Phe Ser Asn Ser Thr Asn Asn Gly Leu Leu
195                 200                 205                 210

TTT ATA AAT ACT ACT ATT GCC AGC ATT GCT GCT AAA GAA GAA GGG GTA     240
Phe Ile Asn Thr Thr Ile Ala Ser Ile Ala Ala Lys Glu Glu Gly Val
```

```
                215                 220                 225
TCT CTA GAT AAA AGA GAG GTT GTT AGA GAG GTG TGC TCT GAA CAA GCT      288
Ser Leu Asp Lys Arg Glu Val Val Arg Glu Val Cys Ser Glu Gln Ala
            230                 235                 240

GAG ACC GGT CCG TGC CGT GCA TTG CAC TCC CGC TGG TAC TTT GAC GTC      336
Glu Thr Gly Pro Cys Arg Ala Leu His Ser Arg Trp Tyr Phe Asp Val
            245                 250                 255

ACT GAA GGT AAG TGC GCT CCA TTC TTT TAC GGC GGT TGC GGC GGC AAC      384
Thr Glu Gly Lys Cys Ala Pro Phe Phe Tyr Gly Gly Cys Gly Gly Asn
            260                 265                 270

CGT AAC AAC TTT GAC ACT GAA GAG TAC TGC ATG GCA GTG TGC GGA TCC      432
Arg Asn Asn Phe Asp Thr Glu Glu Tyr Cys Met Ala Val Cys Gly Ser
275                 280                 285                 290

GCT ATT TAAGCTT                                                      445
Ala Ile
```

(2) INFORMATION FOR SEQ ID NO: 99:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 99:

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg Glu Val Val Arg Glu Val Cys Ser Glu Gln Ala
                85                  90                  95

Glu Thr Gly Pro Cys Arg Ala Leu His Ser Arg Trp Tyr Phe Asp Val
                100                 105                 110

Thr Glu Gly Lys Cys Ala Pro Phe Phe Tyr Gly Gly Cys Gly Gly Asn
            115                 120                 125

Arg Asn Asn Phe Asp Thr Glu Glu Tyr Cys Met Ala Val Cys Gly Ser
        130                 135                 140

Ala Ile
145
```

(2) INFORMATION FOR SEQ ID NO: 100:

(i) SEQUENCE CHARACTERISTICS:
        (A) LENGTH: 704 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..699

(xi) SEQUENCE DESCRIPTION: SEQ ID NO: 100:

```
GTG AAA CAA AGC ACT ATT GCA CTG GCA CTC TTA CCG TTA CTG TTT ACC        48
Val Lys Gln Ser Thr Ile Ala Leu Ala Leu Leu Pro Leu Leu Phe Thr
            150                 155                 160

CCG GTG ACC AAA GCC GAG GTG TGC TCT GAA CAA GCT GAG ACC GGT CCG        96
Pro Val Thr Lys Ala Glu Val Cys Ser Glu Gln Ala Glu Thr Gly Pro
                165                 170                 175

TGC CGT GCA ATG ATC TCC CGC TGG TAC TTT GAC GTC ACT GAA GGT AAG       144
Cys Arg Ala Met Ile Ser Arg Trp Tyr Phe Asp Val Thr Glu Gly Lys
180                 185                 190

TGC GCT CCA TTC TTT TAC GGC GGT TGC GGC GGC AAC CGT AAC AAC TTT       192
Cys Ala Pro Phe Phe Tyr Gly Gly Cys Gly Gly Asn Arg Asn Asn Phe
195                 200                 205                 210

GAC ACT GAA GAG TAC TGC ATG GCA GTG TGC GGA TCC GGT GGT GGC TCT       240
Asp Thr Glu Glu Tyr Cys Met Ala Val Cys Gly Ser Gly Gly Gly Ser
                215                 220                 225

GGT TCC GGT GAT TTT GAT TAT GAA AAG ATG GCA AAC GCT AAT AAG GGG       288
Gly Ser Gly Asp Phe Asp Tyr Glu Lys Met Ala Asn Ala Asn Lys Gly
                230                 235                 240

GCT ATG ACC GAA AAT GCC GAT GAA AAC GCG CTA CAG TCT GAC GCT AAA       336
Ala Met Thr Glu Asn Ala Asp Glu Asn Ala Leu Gln Ser Asp Ala Lys
            245                 250                 255

GGC AAA CTT GAT TCT GTC GCT ACT GAT TAC GGT GCT GCT ATC GAT GGT       384
Gly Lys Leu Asp Ser Val Ala Thr Asp Tyr Gly Ala Ala Ile Asp Gly
260                 265                 270

TTC ATT GGT GAC GTT TCC GGC CTT GCT AAT GGT AAT GGT GCT ACT GGT       432
Phe Ile Gly Asp Val Ser Gly Leu Ala Asn Gly Asn Gly Ala Thr Gly
275                 280                 285                 290

GAT TTT GCT GGC TCT AAT TCC CAA ATG GCT CAA GTC GGT GAC GGT GAT       480
Asp Phe Ala Gly Ser Asn Ser Gln Met Ala Gln Val Gly Asp Gly Asp
                295                 300                 305

AAT TCA CCT TTA ATG AAT AAT TTC CGT CAA TAT TTA CCT TCC CTC CCT       528
Asn Ser Pro Leu Met Asn Asn Phe Arg Gln Tyr Leu Pro Ser Leu Pro
            310                 315                 320

CAA TCG GTT GAA TGT CGC CCT TTT GTC TTT GGC GCT GGT AAA CCA TAC       576
Gln Ser Val Glu Cys Arg Pro Phe Val Phe Gly Ala Gly Lys Pro Tyr
            325                 330                 335

GAA TTT TCT ATT GAT TGT GAC AAA ATA AAC TTA TTC CGT GGT GTC TTT       624
Glu Phe Ser Ile Asp Cys Asp Lys Ile Asn Leu Phe Arg Gly Val Phe
340                 345                 350

GCG TTT CTT TTA TAT GTT GCC ACC TTT ATG TAT GTA TTT TCT ACG TTT       672
Ala Phe Leu Leu Tyr Val Ala Thr Phe Met Tyr Val Phe Ser Thr Phe
355                 360                 365                 370

GCT AAC ATA CTG CGT AAT AAG GAG TCT TAATA                             704
Ala Asn Ile Leu Arg Asn Lys Glu Ser
                375
```

(2) INFORMATION FOR SEQ ID NO: 101:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO: 101:

```
Val Lys Gln Ser Thr Ile Ala Leu Ala Leu Leu Pro Leu Leu Phe Thr
 1               5                  10                  15

Pro Val Thr Lys Ala Glu Val Cys Ser Glu Gln Ala Glu Thr Gly Pro
                20                  25                  30
```

```
Cys Arg Ala Met Ile Ser Arg Trp Tyr Phe Asp Val Thr Glu Gly Lys
            35                  40                  45

Cys Ala Pro Phe Phe Tyr Gly Gly Cys Gly Gly Asn Arg Asn Asn Phe
     50                  55                  60

Asp Thr Glu Glu Tyr Cys Met Ala Val Cys Gly Ser Gly Gly Gly Ser
 65                  70                  75                  80

Gly Ser Gly Asp Phe Asp Tyr Glu Lys Met Ala Asn Ala Asn Lys Gly
                 85                  90                  95

Ala Met Thr Glu Asn Ala Asp Glu Asn Ala Leu Gln Ser Asp Ala Lys
                100                 105                 110

Gly Lys Leu Asp Ser Val Ala Thr Asp Tyr Gly Ala Ala Ile Asp Gly
            115                 120                 125

Phe Ile Gly Asp Val Ser Gly Leu Ala Asn Gly Asn Gly Ala Thr Gly
        130                 135                 140

Asp Phe Ala Gly Ser Asn Ser Gln Met Ala Gln Val Gly Asp Gly Asp
145                 150                 155                 160

Asn Ser Pro Leu Met Asn Asn Phe Arg Gln Tyr Leu Pro Ser Leu Pro
                165                 170                 175

Gln Ser Val Glu Cys Arg Pro Phe Val Phe Gly Ala Gly Lys Pro Tyr
                180                 185                 190

Glu Phe Ser Ile Asp Cys Asp Lys Ile Asn Leu Phe Arg Gly Val Phe
                195                 200                 205

Ala Phe Leu Leu Tyr Val Ala Thr Phe Met Tyr Val Phe Ser Thr Phe
            210                 215                 220

Ala Asn Ile Leu Arg Asn Lys Glu Ser
225                 230

(2) INFORMATION FOR SEQ ID NO: 102:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..696

(xi) SEQUENCE DESCRIPTION: SEQ ID NO: 102:

GTG AAA CAA AGC ACT ATT GCA CTG GCA CTC TTA CCG TTA CTG TTT ACC        48
Val Lys Gln Ser Thr Ile Ala Leu Ala Leu Leu Pro Leu Leu Phe Thr
     235                 240                 245

CCG GTG ACC AAA GCC GAG GTG TGC TCT GAA CAA GCT GAG ACC GGT CCG        96
Pro Val Thr Lys Ala Glu Val Cys Ser Glu Gln Ala Glu Thr Gly Pro
250                 255                 260                 265

TGC CGT NNS NNS NNS NNS TGG TAC TTT GAC GTC ACT GAA GGT AAG TGC       144
Cys Arg Xaa Xaa Xaa Xaa Trp Tyr Phe Asp Val Thr Glu Gly Lys Cys
            270                 275                 280

GCT CCA TTC TTT TAC GGC GGT TGC GGC GGC AAC CGT AAC AAC TTT GAC       192
Ala Pro Phe Phe Tyr Gly Gly Cys Gly Gly Asn Arg Asn Asn Phe Asp
        285                 290                 295

ACT GAA GAG TAC TGC ATG GCA GTG TGC GGA TCC GGT GGT GGC TCT GGT       240
Thr Glu Glu Tyr Cys Met Ala Val Cys Gly Ser Gly Gly Gly Ser Gly
    300                 305                 310

TCC GGT GAT TTT GAT TAT GAA AAG ATG GCA AAC GCT AAT AAG GGG GCT       288
Ser Gly Asp Phe Asp Tyr Glu Lys Met Ala Asn Ala Asn Lys Gly Ala
    315                 320                 325
```

```
ATG ACC GAA AAT GCC GAT GAA AAC GCG CTA CAG TCT GAC GCT AAA GGC    336
Met Thr Glu Asn Ala Asp Glu Asn Ala Leu Gln Ser Asp Ala Lys Gly
330                 335                 340                 345

AAA CTT GAT TCT GTC GCT ACT GAT TAC GGT GCT GCT ATC GAT GGT TTC    384
Lys Leu Asp Ser Val Ala Thr Asp Tyr Gly Ala Ala Ile Asp Gly Phe
                350                 355                 360

ATT GGT GAC GTT TCC GGC CTT GCT AAT GGT AAT GGT GCT ACT GGT GAT    432
Ile Gly Asp Val Ser Gly Leu Ala Asn Gly Asn Gly Ala Thr Gly Asp
            365                 370                 375

TTT GCT GGC TCT AAT TCC CAA ATG GCT CAA GTC GGT GAC GGT GAT AAT    480
Phe Ala Gly Ser Asn Ser Gln Met Ala Gln Val Gly Asp Gly Asp Asn
        380                 385                 390

TCA CCT TTA ATG AAT AAT TTC CGT CAA TAT TTA CCT TCC CTC CCT CAA    528
Ser Pro Leu Met Asn Asn Phe Arg Gln Tyr Leu Pro Ser Leu Pro Gln
    395                 400                 405

TCG GTT GAA TGT CGC CCT TTT GTC TTT GGC GCT GGT AAA CCA TAC GAA    576
Ser Val Glu Cys Arg Pro Phe Val Phe Gly Ala Gly Lys Pro Tyr Glu
410                 415                 420                 425

TTT TCT ATT GAT TGT GAC AAA ATA AAC TTA TTC CGT GGT GTC TTT GCG    624
Phe Ser Ile Asp Cys Asp Lys Ile Asn Leu Phe Arg Gly Val Phe Ala
                430                 435                 440

TTT CTT TTA TAT GTT GCC ACC TTT ATG TAT GTA TTT TCT ACG TTT GCT    672
Phe Leu Leu Tyr Val Ala Thr Phe Met Tyr Val Phe Ser Thr Phe Ala
            445                 450                 455

AAC ATA CTG CGT AAT AAG GAG TCT TAATA                              701
Asn Ile Leu Arg Asn Lys Glu Ser
        460                 465

(2) INFORMATION FOR SEQ ID NO: 103:

(i) SEQUENCE CHARACTERISTICS:
        (A) LENGTH: 232 amino acids
        (B) TYPE: amino acid
        (D) TOPOLOGY: linear (ii) MOLECULE TYPE: protein (xi) SEQUENCE DESCRIPTION: SEQ ID NO: 103:

Val Lys Gln Ser Thr Ile Ala Leu Ala Leu Leu Pro Leu Leu Phe Thr
1               5                   10                  15

Pro Val Thr Lys Ala Glu Val Cys Ser Glu Gln Ala Glu Thr Gly Pro
                20                  25                  30

Cys Arg Xaa Xaa Xaa Xaa Trp Tyr Phe Asp Val Thr Glu Gly Lys Cys
            35                  40                  45

Ala Pro Phe Phe Tyr Gly Gly Cys Gly Gly Asn Arg Asn Asn Phe Asp
        50                  55                  60

Thr Glu Glu Tyr Cys Met Ala Val Cys Gly Ser Gly Gly Ser Gly
65                  70                  75                  80

Ser Gly Asp Phe Asp Tyr Glu Lys Met Ala Asn Ala Asn Lys Gly Ala
                85                  90                  95

Met Thr Glu Asn Ala Asp Glu Asn Ala Leu Gln Ser Asp Ala Lys Gly
                100                 105                 110

Lys Leu Asp Ser Val Ala Thr Asp Tyr Gly Ala Ala Ile Asp Gly Phe
            115                 120                 125

Ile Gly Asp Val Ser Gly Leu Ala Asn Gly Asn Gly Ala Thr Gly Asp
        130                 135                 140

Phe Ala Gly Ser Asn Ser Gln Met Ala Gln Val Gly Asp Gly Asp Asn
145                 150                 155                 160
```

```
Ser Pro Leu Met Asn Asn Phe Arg Gln Tyr Leu Pro Ser Leu Pro Gln
            165                 170                 175

Ser Val Glu Cys Arg Pro Phe Val Phe Gly Ala Gly Lys Pro Tyr Glu
            180                 185                 190

Phe Ser Ile Asp Cys Asp Lys Ile Asn Leu Phe Arg Gly Val Phe Ala
            195                 200                 205

Phe Leu Leu Tyr Val Ala Thr Phe Met Tyr Val Phe Ser Thr Phe Ala
        210                 215                 220

Asn Ile Leu Arg Asn Lys Glu Ser
225                 230
```

(2) INFORMATION FOR SEQ ID NO: 104:

(i) SEQUENCE CHARACTERISTICS:
        (A) LENGTH: 704 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..699

(xi) SEQUENCE DESCRIPTION: SEQ ID NO: 104:

```
GTG AAA CAA AGC ACT ATT GCA CTG GCA CTC TTA CCG TTA CTG TTT ACC        48
Val Lys Gln Ser Thr Ile Ala Leu Ala Leu Leu Pro Leu Leu Phe Thr
            235                 240                 245

CCG GTG ACC AAA GCC GAG GTG TGC TCT GAA CAA GCT GAG ACC GGT CCG        96
Pro Val Thr Lys Ala Glu Val Cys Ser Glu Gln Ala Glu Thr Gly Pro
            250                 255                 260

TGC CGT GCA GCT ATC TTC CGC TGG TAC TTT GAC GTC ACT GAA GGT AAG       144
Cys Arg Ala Ala Ile Phe Arg Trp Tyr Phe Asp Val Thr Glu Gly Lys
265                 270                 275                 280

TGC GCT CCA TTC TTT TAC GGC GGT TGC GGC GGC AAC CGT AAC AAC TTT       192
Cys Ala Pro Phe Phe Tyr Gly Gly Cys Gly Gly Asn Arg Asn Asn Phe
                285                 290                 295

GAC ACT GAA GAG TAC TGC ATG GCA GTG TGC GGA TCC GGT GGT GGC TCT       240
Asp Thr Glu Glu Tyr Cys Met Ala Val Cys Gly Ser Gly Gly Gly Ser
            300                 305                 310

GGT TCC GGT GAT TTT GAT TAT GAA AAG ATG GCA AAC GCT AAT AAG GGG       288
Gly Ser Gly Asp Phe Asp Tyr Glu Lys Met Ala Asn Ala Asn Lys Gly
            315                 320                 325

GCT ATG ACC GAA AAT GCC GAT GAA AAC GCG CTA CAG TCT GAC GCT AAA       336
Ala Met Thr Glu Asn Ala Asp Glu Asn Ala Leu Gln Ser Asp Ala Lys
            330                 335                 340

GGC AAA CTT GAT TCT GTC GCT ACT GAT TAC GGT GCT GCT ATC GAT GGT       384
Gly Lys Leu Asp Ser Val Ala Thr Asp Tyr Gly Ala Ala Ile Asp Gly
345                 350                 355                 360

TTC ATT GGT GAC GTT TCC GGC CTT GCT AAT GGT AAT GGT GCT ACT GGT       432
Phe Ile Gly Asp Val Ser Gly Leu Ala Asn Gly Asn Gly Ala Thr Gly
                365                 370                 375

GAT TTT GCT GGC TCT AAT TCC CAA ATG GCT CAA GTC GGT GAC GGT GAT       480
Asp Phe Ala Gly Ser Asn Ser Gln Met Ala Gln Val Gly Asp Gly Asp
            380                 385                 390

AAT TCA CCT TTA ATG AAT AAT TTC CGT CAA TAT TTA CCT TCC CTC CCT       528
Asn Ser Pro Leu Met Asn Asn Phe Arg Gln Tyr Leu Pro Ser Leu Pro
            395                 400                 405

CAA TCG GTT GAA TGT CGC CCT TTT GTC TTT GGC GCT GGT AAA CCA TAC       576
Gln Ser Val Glu Cys Arg Pro Phe Val Phe Gly Ala Gly Lys Pro Tyr
        410                 415                 420
```

-continued

```
GAA TTT TCT ATT GAT TGT GAC AAA ATA AAC TTA TTC CGT GGT GTC TTT       624
Glu Phe Ser Ile Asp Cys Asp Lys Ile Asn Leu Phe Arg Gly Val Phe
425                 430                 435                 440

GCG TTT CTT TTA TAT GTT GCC ACC TTT ATG TAT GTA TTT TCT ACG TTT       672
Ala Phe Leu Leu Tyr Val Ala Thr Phe Met Tyr Val Phe Ser Thr Phe
                445                 450                 455

GCT AAC ATA CTG CGT AAT AAG GAG TCT TAATA                             704
Ala Asn Ile Leu Arg Asn Lys Glu Ser
460                 465
```

(2) INFORMATION FOR SEQ ID NO: 105:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO: 105:

```
Val Lys Gln Ser Thr Ile Ala Leu Ala Leu Leu Pro Leu Leu Phe Thr
1               5                   10                  15

Pro Val Thr Lys Ala Glu Val Cys Ser Glu Gln Ala Glu Thr Gly Pro
                20                  25                  30

Cys Arg Ala Ala Ile Phe Arg Trp Tyr Phe Asp Val Thr Glu Gly Lys
                35                  40                  45

Cys Ala Pro Phe Phe Tyr Gly Gly Cys Gly Gly Asn Arg Asn Asn Phe
            50                  55                  60

Asp Thr Glu Glu Tyr Cys Met Ala Val Cys Gly Ser Gly Gly Gly Ser
65                  70                  75                  80

Gly Ser Gly Asp Phe Asp Tyr Glu Lys Met Ala Asn Ala Asn Lys Gly
                85                  90                  95

Ala Met Thr Glu Asn Ala Asp Glu Asn Ala Leu Gln Ser Asp Ala Lys
                    100                 105                 110

Gly Lys Leu Asp Ser Val Ala Thr Asp Tyr Gly Ala Ala Ile Asp Gly
            115                 120                 125

Phe Ile Gly Asp Val Ser Gly Leu Ala Asn Gly Asn Gly Ala Thr Gly
130                 135                 140

Asp Phe Ala Gly Ser Asn Ser Gln Met Ala Gln Val Gly Asp Gly Asp
145                 150                 155                 160

Asn Ser Pro Leu Met Asn Asn Phe Arg Gln Tyr Leu Pro Ser Leu Pro
                165                 170                 175

Gln Ser Val Glu Cys Arg Pro Val Phe Gly Ala Gly Lys Pro Tyr
            180                 185                 190

Glu Phe Ser Ile Asp Cys Asp Lys Ile Asn Leu Phe Arg Gly Val Phe
                195                 200                 205

Ala Phe Leu Leu Tyr Val Ala Thr Phe Met Tyr Val Phe Ser Thr Phe
            210                 215                 220

Ala Asn Ile Leu Arg Asn Lys Glu Ser
225                 230
```

(2) INFORMATION FOR SEQ ID NO: 106:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
    (A) NAME/KEY: CDS
    (B) LOCATION: 1..438

(xi) SEQUENCE DESCRIPTION: SEQ ID NO: 106:

```
ATG AGA TTT CCT TCA ATT TTT ACT GCA GTT TTA TTC GCA GCA TCC TCC        48
Met Arg Phe Pro Ser Ile Phe Thr Ala Val Leu Phe Ala Ala Ser Ser
235                 240                 245

GCA TTA GCT GCT CCA GTC AAC ACT ACA GAA GAT GAA ACG GCA CAA            96
Ala Leu Ala Ala Pro Val Asn Thr Thr Thr Glu Asp Glu Thr Ala Gln
250                 255                 260                 265

ATT CCG GCT GAA GCT GTC ATC GGT TAC TTA GAT TTA GAA GGG GAT TTC       144
Ile Pro Ala Glu Ala Val Ile Gly Tyr Leu Asp Leu Glu Gly Asp Phe
                270                 275                 280

GAT GTT GCT GTT TTG CCA TTT TCC AAC AGC ACA AAT AAC GGG TTA TTG       192
Asp Val Ala Val Leu Pro Phe Ser Asn Ser Thr Asn Asn Gly Leu Leu
                285                 290                 295

TTT ATA AAT ACT ACT ATT GCC AGC ATT GCT GCT AAA GAA GAA GGG GTA       240
Phe Ile Asn Thr Thr Ile Ala Ser Ile Ala Ala Lys Glu Glu Gly Val
                300                 305                 310

TCT CTA GAT AAA AGA GAG GTT GTT AGA GAG GTG TGC TCT GAA CAA GCT       288
Ser Leu Asp Lys Arg Glu Val Val Arg Glu Val Cys Ser Glu Gln Ala
315                 320                 325

GAG ACC GGT CCG TGC CGT GCA GCT ATC TTC CGC TGG TAC TTT GAC GTC       336
Glu Thr Gly Pro Cys Arg Ala Ala Ile Phe Arg Trp Tyr Phe Asp Val
330                 335                 340                 345

ACT GAA GGT AAG TGC GCT CCA TTC TTT TAC GGC GGT TGC GGC GGC AAC       384
Thr Glu Gly Lys Cys Ala Pro Phe Phe Tyr Gly Gly Cys Gly Gly Asn
                350                 355                 360

CGT AAC AAC TTT GAC ACT GAA GAG TAC TGC ATG GCA GTG TGC GGA TCC       432
Arg Asn Asn Phe Asp Thr Glu Glu Tyr Cys Met Ala Val Cys Gly Ser
                365                 370                 375

GCT ATT TAAGCTT                                                       445
Ala Ile
```

(2) INFORMATION FOR SEQ ID NO: 107:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 107:

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65              70                  75                  80

Ser Leu Asp Lys Arg Glu Val Val Arg Glu Val Cys Ser Glu Gln Ala
                85                  90                  95

Glu Thr Gly Pro Cys Arg Ala Ala Ile Phe Arg Trp Tyr Phe Asp Val
            100                 105                 110
```

```
Thr Glu Gly Lys Cys Ala Pro Phe Phe Tyr Gly Cys Gly Gly Asn
        115                 120                 125

Arg Asn Asn Phe Asp Thr Glu Glu Tyr Cys Met Ala Val Cys Gly Ser
        130                 135                 140

Ala Ile
145
```

(2) INFORMATION FOR SEQ ID NO: 108:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 108:

```
Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
                35                  40                  45

Glu Asp Cys Met Arg Thr Cys Gly Gly Ala
        50                  55
```

(2) INFORMATION FOR SEQ ID NO: 109:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 109:

```
Asp Phe Cys Leu Glu Pro Pro Tyr Thr Gly Pro Cys Arg Ala Arg Ile
1               5                   10                  15

Ile Arg Tyr Phe Tyr Asn Ala Lys Ala Gly Leu Cys Gln Thr Phe Val
            20                  25                  30

Tyr Gly Gly Cys Arg Ala Lys Ser Asn Asn Phe Lys Ser Ala Glu Asp
                35                  40                  45

Cys Met Arg Thr Cys Gly Gly Ala
        50                  55
```

(2) INFORMATION FOR SEQ ID NO: 110:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 110:

```
Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30
```

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile
         50                  55                  60

(2) INFORMATION FOR SEQ ID NO: 111:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 111:

Glu Val Val Arg Glu Val Cys Ser Glu Gln Ala Glu Pro Gly Pro Cys
1               5                  10                  15

Arg Ala Met Ile Ser Arg Trp Tyr Phe Asp Val Thr Glu Gly Lys Cys
         20                  25                  30

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile
         50                  55                  60

(2) INFORMATION FOR SEQ ID NO: 112:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 112:

Glu Val Val Arg Glu Val Cys Ser Glu Gln Ala Glu Val Gly Pro Cys
1               5                  10                  15

Arg Ala Met Ile Ser Arg Trp Tyr Phe Asp Val Thr Glu Gly Lys Cys
         20                  25                  30

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile
         50                  55                  60

(2) INFORMATION FOR SEQ ID NO: 113:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 113:

Glu Val Val Arg Glu Val Cys Ser Glu Gln Ala Glu Ser Gly Pro Cys
1               5                  10                  15

Arg Ala Met Ile Ser Arg Trp Tyr Phe Asp Val Thr Glu Gly Lys Cys
         20                  25                  30

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile

```
        50              55              60
```

(2) INFORMATION FOR SEQ ID NO: 114:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 114:

```
Glu Val Cys Ser Glu Gln Ala Glu Thr Gly Pro Cys Lys Ala Met Ile
1               5                   10                  15

Ser Arg Trp Tyr Phe Asp Val Thr Glu Gly Lys Cys Ala Pro Phe Phe
            20                  25                  30

Tyr Gly Gly Cys Gly Gly Asn Arg Asn Asn Phe Asp Thr Glu Glu Tyr
        35                  40                  45

Cys Met Ala Val Cys Gly Ser Ala Ile
    50                  55
```

(2) INFORMATION FOR SEQ ID NO: 115:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 115:

```
Glu Val Val Arg Glu Val Cys Ser Glu Gln Ala Glu Thr Gly Pro Cys
1               5                   10                  15

Arg Gly Met Ile Ser Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60
```

(2) INFORMATION FOR SEQ ID NO: 116:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 116:

```
Glu Val Cys Ser Glu Gln Ala Glu Thr Gly Pro Cys Arg Ala Arg Ile
1               5                   10                  15

Ser Arg Trp Tyr Phe Asp Val Thr Glu Gly Lys Cys Ala Pro Phe Phe
            20                  25                  30

Tyr Gly Gly Cys Gly Gly Asn Arg Asn Asn Phe Asp Thr Glu Glu Tyr
        35                  40                  45

Cys Met Ala Val Cys Gly Ser Ala Ile
    50                  55
```

(2) INFORMATION FOR SEQ ID NO: 117:

(i) SEQUENCE CHARACTERISTICS:
    (A) LENGTH: 61 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 117:

```
Glu Val Val Arg Glu Val Cys Ser Glu Gln Ala Glu Thr Gly Pro Cys
1               5                  10                  15

Arg Ala Ala Ile Ser Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 118:

(i) SEQUENCE CHARACTERISTICS:
    (A) LENGTH: 61 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 118:

```
Glu Val Val Arg Glu Val Cys Ser Glu Gln Ala Glu Thr Gly Pro Cys
1               5                  10                  15

Arg Ala Ile Ile Ser Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 119:

(i) SEQUENCE CHARACTERISTICS:
    (A) LENGTH: 61 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 119:

```
Glu Val Val Arg Glu Val Cys Ser Glu Gln Ala Glu Thr Gly Pro Cys
1               5                  10                  15

Arg Ala Leu Ile Ser Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 120:

(i) SEQUENCE CHARACTERISTICS:
    (A) LENGTH: 61 amino acids
    (B) TYPE: amino acid (C) STRANDEDNESS: single
        (D) TOPOLOGY: linear (ii) MOLECULE TYPE: protein (xi) SEQUENCE DESCRIPTION: SEQ ID NO: 120:

Glu Val Val Arg Glu Val Cys Ser Glu Gln Ala Glu Thr Gly Pro Cys
1               5                   10                  15

Arg Ala Ser Ile Ser Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 121:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 121:

Glu Val Val Arg Glu Val Cys Ser Glu Gln Ala Glu Thr Gly Pro Cys
1               5                   10                  15

Arg Ala Val Ile Ser Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 122:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 122:

Glu Val Val Arg Glu Val Cys Ser Glu Gln Ala Glu Thr Gly Pro Cys
1               5                   10                  15

Arg Ala Gly Ile Ser Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 123:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 123:

Glu Val Val Arg Glu Val Cys Ser Glu Gln Ala Glu Thr Gly Pro Cys
1               5                   10                  15

Arg Ala Met His Ser Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35              40                  45

Thr Glu Glu Tyr Cys Met Ala Val Cys Gly Ser Ala Ile
50                  55                  60

(2) INFORMATION FOR SEQ ID NO: 124:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 124:

Glu Val Val Arg Glu Val Cys Ser Glu Gln Ala Glu Thr Gly Pro Cys
1               5                   10                  15

Arg Ala Met Ala Ser Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35              40                  45

Thr Glu Glu Tyr Cys Met Ala Val Cys Gly Ser Ala Ile
50                  55                  60

(2) INFORMATION FOR SEQ ID NO: 125:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 125:

Glu Val Val Arg Glu Val Cys Ser Glu Gln Ala Glu Thr Gly Pro Cys
1               5                   10                  15

Arg Ala Met Phe Ser Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35              40                  45

Thr Glu Glu Tyr Cys Met Ala Val Cys Gly Ser Ala Ile
50                  55                  60

(2) INFORMATION FOR SEQ ID NO: 126:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 126:

Glu Val Val Arg Glu Val Cys Ser Glu Gln Ala Glu Thr Gly Pro Cys

```
                   1               5                  10                 15
Arg Ala Met Lys Ser Arg Trp Tyr Phe Asp Val Thr Glu Gly Lys Cys
                   20                 25                30

Ala Pro Phe Phe Tyr Gly Gly Cys Gly Gly Asn Arg Asn Asn Phe Asp
                   35                 40                45

Thr Glu Glu Tyr Cys Met Ala Val Cys Gly Ser Ala Ile
                   50                 55                60

(2) INFORMATION FOR SEQ ID NO: 127:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 127:

Glu Val Val Arg Glu Val Cys Ser Gln Ala Glu Thr Gly Pro Cys
1                  5                  10                 15

Arg Ala Met Leu Ser Arg Trp Tyr Phe Asp Val Thr Glu Gly Lys Cys
                   20                 25                30

Ala Pro Phe Phe Tyr Gly Gly Cys Gly Gly Asn Arg Asn Asn Phe Asp
                   35                 40                45

Thr Glu Glu Tyr Cys Met Ala Val Cys Gly Ser Ala Ile
                   50                 55                60

(2) INFORMATION FOR SEQ ID NO: 128:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 128:

Glu Val Cys Ser Glu Gln Ala Glu Thr Gly Pro Cys Arg Ala Met Ile
1                  5                  10                 15

Ile Arg Trp Tyr Phe Asp Val Thr Glu Gly Lys Cys Ala Pro Phe Phe
                   20                 25                30

Tyr Gly Gly Cys Gly Gly Asn Arg Asn Asn Phe Asp Thr Glu Glu Tyr
                   35                 40                45

Cys Met Ala Val Cys Gly Ser Ala Ile
                   50                 55

(2) INFORMATION FOR SEQ ID NO: 129:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 129:

Glu Val Val Arg Glu Val Cys Ser Gln Ala Glu Thr Gly Pro Cys
1                  5                  10                 15

Arg Ala Met Ile Pro Arg Trp Tyr Phe Asp Val Thr Glu Gly Lys Cys
                   20                 25                30
```

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
 50                  55                  60

(2) INFORMATION FOR SEQ ID NO: 130:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 130:

Glu Val Val Arg Glu Val Cys Ser Gln Ala Glu Thr Gly Pro Cys
 1               5                  10                  15

Arg Ala Met Ile Phe Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
 50                  55                  60

(2) INFORMATION FOR SEQ ID NO: 131:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 131:

Glu Val Val Arg Glu Val Cys Ser Gln Ala Glu Thr Gly Pro Cys
 1               5                  10                  15

Arg Ala Met Ile Tyr Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
 50                  55                  60

(2) INFORMATION FOR SEQ ID NO: 132:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 132:

Glu Val Val Arg Glu Val Cys Ser Gln Ala Glu Thr Gly Pro Cys
 1               5                  10                  15

Arg Ala Met Ile Trp Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
        35                  40                  45

```
Thr Glu Glu Tyr Cys Met Ala Val Cys Gly Ser Ala Ile
    50                  55                  60
```

(2) INFORMATION FOR SEQ ID NO: 133:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 133:

```
Glu Val Val Arg Glu Val Cys Ser Gln Ala Glu Thr Gly Pro Cys
1               5                   10                  15

Arg Ala Met Ile Leu Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 134:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 134:

```
Glu Val Val Arg Glu Val Cys Ser Gln Ala Glu Thr Gly Pro Cys
1               5                   10                  15

Arg Ala Met Ile His Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 135:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 135:

```
Glu Val Val Arg Glu Val Cys Ser Gln Ala Glu Thr Gly Pro Cys
1               5                   10                  15

Arg Ala Met Ile Glu Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 136:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 136:

```
Glu Val Val Arg Glu Val Cys Ser Gln Ala Glu Thr Gly Pro Cys
1               5                  10                  15

Arg Ala Met Ile Gln Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
50                  55                  60
```

(2) INFORMATION FOR SEQ ID NO: 137:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 137:

```
Glu Val Val Arg Glu Val Cys Ser Gln Ala Glu Thr Gly Pro Cys
1               5                  10                  15

Arg Ala Met Ile Ser Ala Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
50                  55                  60
```

(2) INFORMATION FOR SEQ ID NO: 138:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 138:

```
Glu Val Val Arg Glu Val Cys Ser Gln Ala Glu Thr Gly Pro Cys
1               5                  10                  15

Arg Ala Met Ile Ser Thr Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
50                  55                  60
```

(2) INFORMATION FOR SEQ ID NO: 139:

(i) SEQUENCE CHARACTERISTICS:
        (A) LENGTH: 61 amino acids (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 139:

Glu Val Val Arg Glu Val Cys Ser Gln Ala Glu Thr Gly Pro Cys
1               5                   10                  15

Arg Ala Met Ile Ser His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60

(2) INFORMATION FOR SEQ ID NO: 140:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 140:

Glu Val Val Arg Glu Val Cys Ser Gln Ala Glu Thr Gly Pro Cys
1               5                   10                  15

Arg Ala Met Ile Ser Lys Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60

(2) INFORMATION FOR SEQ ID NO: 141:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 141:

Glu Val Val Arg Glu Val Cys Ser Gln Ala Glu Thr Gly Pro Cys
1               5                   10                  15

Arg Ala Met Ile Ser Leu Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
    50                  55                  60

(2) INFORMATION FOR SEQ ID NO: 142:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 142:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Val Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 143:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 143:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Leu Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 144:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 144:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Gly Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 145:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 145:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
                20                  25                  30

Ala Pro Phe Phe Tyr Gly Gly Cys Ala Gly Asn Arg Asn Asn Phe Asp
                35                  40                  45

Thr Glu Glu Tyr Cys Met Ala Val Cys Gly Ser Ala Ile
50                  55                  60

(2) INFORMATION FOR SEQ ID NO: 146:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 146:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
                20                  25                  30

Ala Pro Phe Phe Tyr Gly Gly Cys Lys Gly Asn Arg Asn Asn Phe Asp
                35                  40                  45

Thr Glu Glu Tyr Cys Met Ala Val Cys Gly Ser Ala Ile
50                  55                  60

(2) INFORMATION FOR SEQ ID NO: 147:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 147:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
                20                  25                  30

Ala Pro Phe Phe Tyr Gly Gly Cys Leu Gly Asn Arg Asn Asn Phe Asp
                35                  40                  45

Thr Glu Glu Tyr Cys Met Ala Val Cys Gly Ser Ala Ile
50                  55                  60

(2) INFORMATION FOR SEQ ID NO: 148:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 148:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys

```
            20                  25                  30
Ala Pro Phe Phe Tyr Gly Gly Cys Met Gly Asn Arg Asn Asn Phe Asp
            35                  40                  45

Thr Glu Glu Tyr Cys Met Ala Val Cys Gly Ser Ala Ile
 50                  55                  60
```

(2) INFORMATION FOR SEQ ID NO: 149:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 149:

```
Glu Val Val Arg Glu Val Cys Ser Gln Ala Glu Thr Gly Pro Cys
 1                   5                  10                  15

Arg Ala Met Ile Ser Arg Trp Tyr Phe Asp Val Thr Glu Gly Lys Cys
            20                  25                  30

Ala Pro Phe Phe Tyr Gly Gly Cys Asn Gly Asn Arg Asn Asn Phe Asp
            35                  40                  45

Thr Glu Glu Tyr Cys Met Ala Val Cys Gly Ser Ala Ile
 50                  55                  60
```

(2) INFORMATION FOR SEQ ID NO: 150:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 150:

```
Glu Val Val Arg Glu Val Cys Ser Gln Ala Glu Thr Gly Pro Cys
 1                   5                  10                  15

Arg Ala Met Ile Ser Arg Trp Tyr Phe Asp Val Thr Glu Gly Lys Cys
            20                  25                  30

Ala Pro Phe Phe Tyr Gly Gly Cys Pro Gly Asn Arg Asn Asn Phe Asp
            35                  40                  45

Thr Glu Glu Tyr Cys Met Ala Val Cys Gly Ser Ala Ile
 50                  55                  60
```

(2) INFORMATION FOR SEQ ID NO: 151:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 151:

```
Glu Val Val Arg Glu Val Cys Ser Gln Ala Glu Thr Gly Pro Cys
 1                   5                  10                  15

Arg Ala Met Ile Ser Arg Trp Tyr Phe Asp Val Thr Glu Gly Lys Cys
            20                  25                  30

Ala Pro Phe Phe Tyr Gly Gly Cys Gln Gly Asn Arg Asn Asn Phe Asp
            35                  40                  45
```

Thr Glu Glu Tyr Cys Met Ala Val Cys Gly Ser Ala Ile
            50                  55                  60

(2) INFORMATION FOR SEQ ID NO: 152:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 152:

Glu Val Cys Ser Glu Gln Ala Glu Thr Gly Pro Cys Arg Ala Met Ile
1               5                  10                  15

Ser Arg Trp Tyr Phe Asp Val Thr Glu Gly Lys Cys Ala Pro Phe Phe
            20                  25                  30

Tyr Gly Gly Cys Arg Gly Asn Arg Asn Asn Phe Asp Thr Glu Glu Tyr
        35                  40                  45

Cys Met Ala Val Cys Gly Ser Ala Ile
    50                  55

(2) INFORMATION FOR SEQ ID NO: 153:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 153:

Glu Val Val Arg Glu Val Cys Ser Glu Gln Ala Glu Thr Gly Pro Cys
1               5                  10                  15

Arg Ala Met Ile Ser Arg Trp Tyr Phe Asp Val Thr Glu Gly Lys Cys
            20                  25                  30

Ala Pro Phe Phe Tyr Gly Gly Cys Cys Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 154:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 154:

Glu Val Val Arg Glu Val Cys Ser Glu Gln Ala Glu Thr Gly Pro Cys
1               5                  10                  15

Arg Ala Met Ile Ser Arg Trp Tyr Phe Asp Val Thr Glu Gly Lys Cys
            20                  25                  30

Ala Pro Phe Phe Tyr Gly Gly Cys Ser Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 155:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 155:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Thr Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 156:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 156:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Val Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 157:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 157:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Tyr Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 158:

(i) SEQUENCE CHARACTERISTICS:

(A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 158:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Asp Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 159:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 159:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Glu Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 160:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 160:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys His Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 161:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 161:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Ile Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 162:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 162:

Glu Val Cys Ser Glu Gln Ala Glu Thr Gly Pro Cys Arg Ala Met Ile
1               5                   10                  15

Ser Arg Trp Tyr Phe Asp Val Thr Glu Gly Lys Cys Ala Pro Phe Phe
            20                  25                  30

Tyr Gly Gly Cys Gly Ala Asn Arg Asn Asn Phe Asp Thr Glu Glu Tyr
        35                  40                  45

Cys Met Ala Val Cys Gly Ser Ala Ile
50                  55

(2) INFORMATION FOR SEQ ID NO: 163:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 163:

Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Gly Arg Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 164:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 164:

```
Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Gly Gly Ala Arg Asn Asn Phe Asp
            35                  40                  45

Thr Glu Glu Tyr Cys Met Ala Val Cys Gly Ser Ala Ile
50                  55                  60
```

(2) INFORMATION FOR SEQ ID NO: 165:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 165:

```
Glu Val Cys Ser Glu Gln Ala Glu Thr Gly Pro Cys Arg Ala Met Ile
1               5                   10                  15

Ser Arg Trp Tyr Phe Asp Val Thr Glu Gly Lys Cys Ala Pro Phe Phe
            20                  25                  30

Tyr Gly Gly Cys Gly Gly Asn Ser Asn Asn Phe Asp Thr Glu Glu Tyr
            35                  40                  45

Cys Met Ala Val Cys Gly Ser Ala Ile
50                  55
```

(2) INFORMATION FOR SEQ ID NO: 166:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 166:

```
Glu Val Val Arg Glu Val Cys Ser Glu Gln Ala Glu Thr Gly Pro Cys
1               5                   10                  15

Arg Ala Met Ile Ser Arg Trp Tyr Phe Asp Val Thr Glu Gly Lys Cys
            20                  25                  30

Ala Pro Phe Phe Tyr Gly Gly Cys Gly Gly Asn Ala Asn Asn Phe Asp
            35                  40                  45

Thr Glu Glu Tyr Cys Met Ala Val Cys Gly Ser Ala Ile
50                  55                  60
```

(2) INFORMATION FOR SEQ ID NO: 167:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 167:

```
Glu Val Val Arg Glu Val Cys Ser Glu Gln Ala Glu Thr Gly Pro Cys
1               5                   10                  15
```

```
Arg Ala Ala His Ser Arg Trp Tyr Phe Asp Val Thr Glu Gly Lys Cys
        20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
 50                  55                  60

(2) INFORMATION FOR SEQ ID NO: 168:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 168:

Glu Val Val Arg Glu Val Cys Ser Glu Gln Ala Glu Thr Gly Pro Cys
 1               5                  10                  15

Arg Ala Leu His Ser Arg Trp Tyr Phe Asp Val Thr Glu Gly Lys Cys
        20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
 50                  55                  60

(2) INFORMATION FOR SEQ ID NO: 169:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 169:

Glu Val Val Arg Glu Val Cys Ser Glu Gln Ala Glu Thr Gly Pro Cys
 1               5                  10                  15

Arg Ala Leu Leu Ser Arg Trp Tyr Phe Asp Val Thr Glu Gly Lys Cys
        20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
 50                  55                  60

(2) INFORMATION FOR SEQ ID NO: 170:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 170:

Glu Val Val Arg Glu Val Cys Ser Glu Gln Ala Glu Thr Gly Pro Cys
 1               5                  10                  15

Arg Ala Leu Phe Ser Arg Trp Tyr Phe Asp Val Thr Glu Gly Lys Cys
        20                  25                  30

Ala Pro Phe Phe Tyr Gly Gly Cys Gly Gly Asn Arg Asn Asn Phe Asp
```

```
                    35                  40                  45
Thr Glu Glu Tyr Cys Met Ala Val Cys Gly Ser Ala Ile
 50                  55                  60
```

(2) INFORMATION FOR SEQ ID NO: 171:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 171:

```
Glu Val Val Arg Glu Val Cys Ser Glu Gln Ala Glu Thr Gly Pro Cys
 1               5                  10                  15
Arg Ala Ala Ile Phe Arg Trp Tyr Phe Asp Val Thr Glu Gly Lys Cys
                20                  25                  30
Ala Pro Phe Phe Tyr Gly Gly Cys Gly Gly Asn Arg Asn Asn Phe Asp
                35                  40                  45
Thr Glu Glu Tyr Cys Met Ala Val Cys Gly Ser Ala Ile
 50                  55                  60
```

(2) INFORMATION FOR SEQ ID NO: 172:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 172:

```
Glu Val Val Arg Glu Val Cys Ser Glu Gln Ala Glu Thr Gly Pro Cys
 1               5                  10                  15
Arg Ala Ala Ile Trp Arg Trp Tyr Phe Asp Val Thr Glu Gly Lys Cys
                20                  25                  30
Ala Pro Phe Phe Tyr Gly Gly Cys Gly Gly Asn Arg Asn Asn Phe Asp
                35                  40                  45
Thr Glu Glu Tyr Cys Met Ala Val Cys Gly Ser Ala Ile
 50                  55                  60
```

(2) INFORMATION FOR SEQ ID NO: 173:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 173:

```
Glu Val Val Arg Glu Val Cys Ser Glu Gln Ala Glu Thr Gly Pro Cys
 1               5                  10                  15
Arg Ala Ala Ile Tyr Arg Trp Tyr Phe Asp Val Thr Glu Gly Lys Cys
                20                  25                  30
Ala Pro Phe Phe Tyr Gly Gly Cys Gly Gly Asn Arg Asn Asn Phe Asp
                35                  40                  45
Thr Glu Glu Tyr Cys Met Ala Val Cys Gly Ser Ala Ile
 50                  55                  60
```

(2) INFORMATION FOR SEQ ID NO: 174:

(i) SEQUENCE CHARACTERISTICS:
       (A) LENGTH: 61 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 174:

Glu Val Val Arg Glu Val Cys Ser Glu Gln Ala Glu Thr Gly Pro Cys
1               5                   10                  15

Arg Ala Leu Ile Tyr Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 175:

(i) SEQUENCE CHARACTERISTICS:
       (A) LENGTH: 61 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 175:

Glu Val Val Arg Glu Val Cys Ser Glu Gln Ala Glu Thr Gly Pro Cys
1               5                   10                  15

Arg Ala Leu Ile Leu Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 176:

(i) SEQUENCE CHARACTERISTICS:
       (A) LENGTH: 61 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 176:

Glu Val Val Arg Glu Val Cys Ser Glu Gln Ala Glu Thr Gly Pro Cys
1               5                   10                  15

Arg Ala Leu Ile Pro Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 177:

(i) SEQUENCE CHARACTERISTICS:
      (A) LENGTH: 61 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 177:

Glu Val Val Arg Glu Val Cys Ser Glu Gln Ala Glu Thr Gly Pro Cys
1               5                  10                  15

Arg Ala Leu Ile Phe Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 178:

(i) SEQUENCE CHARACTERISTICS:
      (A) LENGTH: 61 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 178:

Glu Val Val Arg Glu Val Cys Ser Glu Gln Ala Glu Thr Gly Pro Cys
1               5                  10                  15

Arg Ala Gly Ile Tyr Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 179:

(i) SEQUENCE CHARACTERISTICS:
      (A) LENGTH: 61 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 179:

Glu Val Val Arg Glu Val Cys Ser Glu Gln Ala Glu Thr Gly Pro Cys
1               5                  10                  15

Arg Ala Gly Ile Trp Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 180:

(i) SEQUENCE CHARACTERISTICS:
      (A) LENGTH: 61 amino acids
      (B) TYPE: amino acid
      (C) STRANDEDNESS: single (D) TOPOLOGY: linear (ii) MOLECULE TYPE: protein (xi) SEQUENCE DESCRIPTION: SEQ ID NO: 180:

Glu Val Val Arg Glu Val Cys Ser Glu Gln Ala Glu Thr Gly Pro Cys
1               5                   10                  15

Arg Ala Gly Ile Pro Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 181:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 181:

Glu Val Val Arg Glu Val Cys Ser Glu Gln Ala Glu Thr Gly Pro Cys
1               5                   10                  15

Arg Ala Ala Ile Ser Ala Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 182:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 182:

Glu Val Val Arg Glu Val Cys Ser Glu Gln Ala Glu Thr Gly Pro Cys
1               5                   10                  15

Arg Ala Leu Ile Ser Ala Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
    50                  55                  60

(2) INFORMATION FOR SEQ ID NO: 183:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 183:

Glu Val Val Arg Glu Val Cys Ser Glu Gln Ala Glu Thr Gly Pro Cys
1               5                   10                  15

Arg Ala Ala Ile Ser Arg Trp Tyr Phe Asp Val Thr Glu Gly Lys Cys
                20                  25                  30

Ala Pro Phe Phe Tyr Gly Gly Cys Arg Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 184:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 184:

Glu Val Val Arg Glu Val Cys Ser Glu Gln Ala Glu Thr Gly Pro Cys
1               5                   10                  15

Arg Ala Ala Ile Ser Arg Trp Tyr Phe Asp Val Thr Glu Gly Lys Cys
                20                  25                  30

Ala Pro Phe Phe Tyr Gly Gly Cys Tyr Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 185:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 185:

Glu Val Val Arg Glu Val Cys Ser Glu Gln Ala Glu Thr Gly Pro Cys
1               5                   10                  15

Arg Ala Met His Phe Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 186:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 186:

Glu Val Val Arg Glu Val Cys Ser Glu Gln Ala Glu Thr Gly Pro Cys
1               5                   10                  15

```
Arg Ala Met His Tyr Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
            50                  55                  60

(2) INFORMATION FOR SEQ ID NO: 187:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 187:

Glu Val Val Arg Glu Val Cys Ser Glu Gln Ala Glu Thr Gly Pro Cys
1               5                   10                  15

Arg Ala Met His Trp Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
            50                  55                  60

(2) INFORMATION FOR SEQ ID NO: 188:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 188:

Glu Val Val Arg Glu Val Cys Ser Glu Gln Ala Glu Thr Gly Pro Cys
1               5                   10                  15

Arg Ala Met Leu His Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
            50                  55                  60

(2) INFORMATION FOR SEQ ID NO: 189:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 189:

Glu Val Val Arg Glu Val Cys Ser Glu Gln Ala Glu Thr Gly Pro Cys
1               5                   10                  15

Arg Ala Met His Ser Arg Trp Tyr Phe Asp Val Thr Glu Gly Lys Cys
            20                  25                  30
```

```
Ala Pro Phe Phe Tyr Gly Gly Cys Tyr Gly Asn Arg Asn Asn Phe Asp
            35                  40                  45

Thr Glu Glu Tyr Cys Met Ala Val Cys Gly Ser Ala Ile
            50                  55                  60
```

(2) INFORMATION FOR SEQ ID NO: 190:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 190:

```
Glu Val Val Arg Glu Val Cys Ser Glu Gln Ala Glu Thr Gly Pro Cys
1               5                   10                  15

Arg Ala Met Ile Phe Arg Trp Tyr Phe Asp Val Thr Glu Gly Lys Cys
            20                  25                  30

Ala Pro Phe Phe Tyr Gly Gly Cys Tyr Gly Asn Arg Asn Asn Phe Asp
            35                  40                  45

Thr Glu Glu Tyr Cys Met Ala Val Cys Gly Ser Ala Ile
            50                  55                  60
```

(2) INFORMATION FOR SEQ ID NO: 191:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 191:

```
Glu Val Val Arg Glu Val Cys Ser Glu Gln Ala Glu Thr Gly Pro Cys
1               5                   10                  15

Arg Ala Met Ile Tyr Arg Trp Tyr Phe Asp Val Thr Glu Gly Lys Cys
            20                  25                  30

Ala Pro Phe Phe Tyr Gly Gly Cys Tyr Gly Asn Arg Asn Asn Phe Asp
            35                  40                  45

Thr Glu Glu Tyr Cys Met Ala Val Cys Gly Ser Ala Ile
            50                  55                  60
```

(2) INFORMATION FOR SEQ ID NO: 192:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 192:

```
Glu Val Val Arg Glu Val Cys Ser Glu Gln Ala Glu Thr Gly Pro Cys
1               5                   10                  15

Arg Ala Met Ile Trp Arg Trp Tyr Phe Asp Val Thr Glu Gly Lys Cys
            20                  25                  30

Ala Pro Phe Phe Tyr Gly Gly Cys Tyr Gly Asn Arg Asn Asn Phe Asp
            35                  40                  45

Thr Glu Glu Tyr Cys Met Ala Val Cys Gly Ser Ala Ile
```

(2) INFORMATION FOR SEQ ID NO: 193:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 193:

Glu Val Val Arg Glu Val Cys Ser Glu Gln Ala Glu Pro Gly Pro Cys
1               5                   10                  15

Arg Ala Leu Ile Leu Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 194:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 194:

Glu Val Val Arg Glu Val Cys Ser Glu Gln Ala Glu Thr Gly Pro Cys
1               5                   10                  15

Arg Gly Tyr Ile Thr Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 195:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 195:

Glu Val Val Arg Glu Val Cys Ser Glu Gln Ala Glu Thr Gly Pro Cys
1               5                   10                  15

Arg Ala Leu His Asn Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 196:

(i) SEQUENCE CHARACTERISTICS:
    (A) LENGTH: 61 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 196:

```
Glu Val Val Arg Glu Val Cys Ser Glu Gln Ala Glu Thr Gly Pro Cys
1               5                   10                  15

Arg Ala Ala His Phe Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60
```

(2) INFORMATION FOR SEQ ID NO: 197:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 197:

```
Glu Val Val Arg Glu Val Cys Ser Glu Gln Ala Glu Thr Gly Pro Cys
1               5                   10                  15

Arg Ala Leu His Phe Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60
```

(2) INFORMATION FOR SEQ ID NO: 198:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 198:

```
Glu Val Val Arg Glu Val Cys Ser Glu Gln Ala Glu Thr Gly Pro Cys
1               5                   10                  15

Arg Ala Ala Leu Phe Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60
```

(2) INFORMATION FOR SEQ ID NO: 199:

(i) SEQUENCE CHARACTERISTICS:
        (A) LENGTH: 61 amino acids
        (B) TYPE: amino acid (C) STRANDEDNESS: single
            (D) TOPOLOGY: linear (ii) MOLECULE TYPE: protein (xi) SEQUENCE DESCRIPTION: SEQ ID NO: 199:

Glu Val Val Arg Glu Val Cys Ser Glu Gln Ala Glu Thr Gly Pro Cys
1               5                   10                  15

Arg Ala Leu Phe Thr Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 200:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 200:

Glu Val Val Arg Glu Val Cys Ser Glu Gln Ala Glu Thr Gly Pro Cys
1               5                   10                  15

Arg Ala Leu Phe Lys Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 201:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 201:

Glu Val Val Arg Glu Val Cys Ser Glu Gln Ala Glu Thr Gly Pro Cys
1               5                   10                  15

Arg Ala Phe Phe Lys Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 202:

(i) SEQUENCE CHARACTERISTICS:
            (A) LENGTH: 61 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 202:

Glu Val Val Arg Glu Val Cys Ser Glu Gln Ala Glu Thr Gly Pro Cys
1               5                   10                  15

Arg Ala Ala Phe Ser Ala Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 203:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 203:

Glu Val Val Arg Glu Val Cys Ser Glu Gln Ala Glu Thr Gly Pro Cys
1               5                   10                  15

Arg Ala Leu Leu Ser Ala Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 204:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 204:

Glu Val Val Arg Glu Val Cys Ser Glu Gln Ala Glu Thr Gly Pro Cys
1               5                   10                  15

Arg Ala Leu Ile Trp His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
        50                  55                  60

(2) INFORMATION FOR SEQ ID NO: 205:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 205:

Glu Val Val Arg Glu Val Cys Ser Glu Gln Ala Glu Thr Gly Pro Cys

```
            1               5                  10                 15
Arg Ala Leu Ile Phe Ala Trp Tyr Phe Asp Val Thr Glu Gly Lys Cys
                    20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
                50                  55                  60

(2) INFORMATION FOR SEQ ID NO: 206:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 206:

Glu Val Val Arg Glu Val Cys Ser Glu Gln Ala Glu Thr Gly Pro Cys
1               5                  10                 15

Arg Ala Leu Ile Tyr His Trp Tyr Phe Asp Val Thr Glu Gly Lys Cys
                    20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
                50                  55                  60

(2) INFORMATION FOR SEQ ID NO: 207:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 207:

Glu Val Val Arg Glu Val Cys Ser Glu Gln Ala Glu Thr Gly Pro Cys
1               5                  10                 15

Arg Ala Ala Ile His Lys Trp Tyr Phe Asp Val Thr Glu Gly Lys Cys
                    20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala Ile
                50                  55                  60

(2) INFORMATION FOR SEQ ID NO: 208:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 208:

Glu Val Val Arg Glu Val Cys Ser Glu Gln Ala Glu Thr Gly Pro Cys
1               5                  10                 15

Arg Ala Ala Ile Tyr His Trp Tyr Phe Asp Val Thr Glu Gly Lys Cys
                    20                  25                  30
```

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile
         50                  55                  60

(2) INFORMATION FOR SEQ ID NO: 209:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 209:

Glu Val Val Arg Glu Val Cys Ser Gly Gln Ala Glu Thr Gly Pro Cys
1               5                   10                  15

Arg Ala Leu Ile Gln His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile
         50                  55                  60

(2) INFORMATION FOR SEQ ID NO: 210:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 210:

Glu Val Val Arg Glu Val Cys Ser Gly Gln Ala Glu Thr Gly Pro Cys
1               5                   10                  15

Arg Ala Leu Ile Tyr Lys Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
         35                  40                  45

Thr Glu Glu Tyr Cys Met Ala Val Cys Gly Ser Ala Ile
         50                  55                  60

(2) INFORMATION FOR SEQ ID NO: 211:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 211:

Glu Val Val Arg Glu Val Cys Ser Gly Gln Ala Glu Thr Gly Pro Cys
1               5                   10                  15

Arg Ala Ala Ile Gln His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
         35                  40                  45

```
Thr Glu Glu Tyr Cys Met Ala Val Cys Gly Ser Ala Ile
    50                  55                  60
```

(2) INFORMATION FOR SEQ ID NO: 212:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 212:

```
Glu Val Val Arg Glu Val Cys Ser Gln Ala Glu Thr Gly Pro Cys
1               5                   10                  15

Arg Ala Ala Ile Phe Arg Trp Tyr Phe Asp Val Thr Glu Gly Lys Cys
                20                  25                  30

Ala Pro Phe Phe Tyr Gly Gly Cys Arg Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 213:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 213:

```
Glu Val Val Arg Glu Val Cys Ser Gln Ala Glu Thr Gly Pro Cys
1               5                   10                  15

Arg Ala Ala Ile Phe Arg Trp Tyr Phe Asp Val Thr Glu Gly Lys Cys
                20                  25                  30

Ala Pro Phe Phe Tyr Gly Gly Cys Tyr Gly Asn Arg Asn Asn Phe Asp
                35                  40                  45

Thr Glu Glu Tyr Cys Met Ala Val Cys Gly Ser Ala Ile
    50                  55                  60
```

(2) INFORMATION FOR SEQ ID NO: 214:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 214:

```
Glu Val Val Arg Glu Val Cys Ser Gln Ala Glu Thr Gly Pro Cys
1               5                   10                  15

Arg Ala Leu Ile Pro Arg Trp Tyr Phe Asp Val Thr Glu Gly Lys Cys
                20                  25                  30

Ala Pro Phe Phe Tyr Gly Gly Cys Arg Gly Asn Arg Asn Asn Phe Asp
                35                  40                  45

Thr Glu Glu Tyr Cys Met Ala Val Cys Gly Ser Ala Ile
    50                  55                  60
```

```
(2) INFORMATION FOR SEQ ID NO: 215:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 215:

Glu Val Val Arg Glu Val Cys Ser Gln Ala Glu Val Gly Pro Cys
1               5                  10                  15

Arg Ala Leu Ile Tyr His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 216:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 216:

Glu Val Val Arg Glu Val Cys Ser Gln Ala Glu Ser Gly Pro Cys
1               5                  10                  15

Arg Ala Leu Ile Tyr His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 217:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 217:

Glu Val Val Arg Glu Val Cys Ser Gln Ala Glu Val Gly Pro Cys
1               5                  10                  15

Arg Ala Ala Ile Tyr His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 218:

(i) SEQUENCE CHARACTERISTICS:
        (A) LENGTH: 61 amino acids
```

(B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 218:

Glu Val Val Arg Glu Val Cys Ser Glu Gln Ala Glu Ser Gly Pro Cys
1               5                   10                  15

Arg Ala Ala Ile Tyr His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 219:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 219:

Glu Val Val Arg Glu Val Cys Ser Glu Gln Ala Glu Ile Gly Pro Cys
1               5                   10                  15

Arg Ala Leu Ile Tyr His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 220:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 220:

Glu Val Val Arg Glu Val Cys Ser Glu Gln Ala Glu Thr Gly Pro Cys
1               5                   10                  15

Arg Gly Ala Ile Gln His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

Thr Glu Glu Tyr Cys Met Ala Val Cys Gly Ser Ala Ile
50                  55                  60

(2) INFORMATION FOR SEQ ID NO: 221:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 221:

Glu Val Val Arg Glu Val Cys Ser Glu Gln Ala Glu Thr Gly Pro Cys
1               5                   10                  15

Arg Gly Ala Ile Arg His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 222:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 222:

Glu Val Val Arg Glu Val Cys Ser Glu Gln Ala Glu Thr Gly Pro Cys
1               5                   10                  15

Arg Gly Ser Ile Arg His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 223:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 223:

Glu Val Val Arg Glu Val Cys Ser Glu Gln Ala Glu Thr Gly Pro Cys
1               5                   10                  15

Arg Gly Leu Ile Tyr His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
50                  55                  60

(2) INFORMATION FOR SEQ ID NO: 224:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 224:

-continued

Glu Val Val Arg Glu Val Cys Ser Glu Gln Ala Glu Thr Gly Pro Cys
1               5                   10                  15

Arg Gly Ala Ile Tyr His Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 225:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 225:

Glu Val Val Arg Glu Val Cys Ser Glu Gln Ala Glu Thr Gly Pro Cys
1               5                   10                  15

Arg Ala Leu His Asn Arg Trp Tyr Phe Asp Val Thr Glu Gly Lys Cys
            20                  25                  30

Ala Pro Phe Phe Tyr Gly Gly Cys Arg Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 226:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 226:

Glu Val Val Arg Glu Val Cys Ser Glu Gln Ala Glu Thr Gly Pro Cys
1               5                   10                  15

Arg Ala Leu Phe Lys Arg Trp Tyr Phe Asp Val Thr Glu Gly Lys Cys
            20                  25                  30

Ala Pro Phe Phe Tyr Gly Gly Cys Tyr Gly Asn Arg Asn Asn Phe Asp
            35                  40                  45

Thr Glu Glu Tyr Cys Met Ala Val Cys Gly Ser Ala Ile
    50                  55                  60

(2) INFORMATION FOR SEQ ID NO: 227:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 227:

Glu Val Val Arg Glu Val Cys Ser Glu Gln Ala Glu Thr Gly Pro Cys
1               5                   10                  15

Arg Ala Leu Phe Lys Arg Trp Tyr Phe Asp Val Thr Glu Gly Lys Cys

-continued

```
                20              25              30
Ala Pro Phe Phe Tyr Gly Gly Cys Leu Gly Asn Arg Asn Asn Phe Asp
            35              40              45

Thr Glu Glu Tyr Cys Met Ala Val Cys Gly Ser Ala Ile
 50              55              60
```

(2) INFORMATION FOR SEQ ID NO: 228:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 228:

```
Glu Val Val Arg Glu Val Cys Ser Glu Gln Ala Glu Thr Gly Pro Cys
 1               5              10              15

Arg Ala Leu Phe Lys Arg Trp Tyr Phe Asp Val Thr Glu Gly Lys Cys
            20              25              30

Ala Pro Phe Phe Tyr Gly Gly Cys Met Gly Asn Arg Asn Asn Phe Asp
            35              40              45

Thr Glu Glu Tyr Cys Met Ala Val Cys Gly Ser Ala Ile
 50              55              60
```